United States Patent
Hohn et al.

(10) Patent No.: US 7,166,770 B2
(45) Date of Patent: Jan. 23, 2007

(54) CESTRUM YELLOW LEAF CURLING VIRUS PROMOTERS

(75) Inventors: Thomas Hohn, Arlesheim (CH); Livia Stavolone, Zürich (CH); Petrus Theodorus De Haan, Oegstgeest (NL); Hope Thompson Ligon, Apex, NC (US); Maria Kononova, Raleigh, NC (US)

(73) Assignee: Syngenta Participations AG, Basel (CH)

( * ) Notice: Subject to any disclaimer, the term of this patent is extended or adjusted under 35 U.S.C. 154(b) by 295 days.

(21) Appl. No.: 10/239,907

(22) PCT Filed: Mar. 26, 2001

(86) PCT No.: PCT/EP01/03408

§ 371 (c)(1),
(2), (4) Date: Mar. 25, 2003

(87) PCT Pub. No.: WO01/73087

PCT Pub. Date: Oct. 4, 2001

(65) Prior Publication Data

US 2004/0086847 A1     May 6, 2004

Related U.S. Application Data

(60) Provisional application No. 60/272,076, filed on Feb. 28, 2001.

(30) Foreign Application Priority Data

Mar. 27, 2000  (GB) ................................. 0007427.8
Apr. 28, 2000  (GB) ................................. 0010486.9
Jan. 26, 2001  (EP) ................................. 01101802

(51) Int. Cl.
*C12N 15/00*     (2006.01)

(52) U.S. Cl. .................. 800/298; 435/320.1; 435/410; 536/24.1

(58) Field of Classification Search ..................... None
See application file for complete search history.

(56) References Cited

U.S. PATENT DOCUMENTS 5,824,857 A   10/1998   Beachy et al.

FOREIGN PATENT DOCUMENTS

EP         0 426 641        5/1991
WO         WO8402913        8/1984

OTHER PUBLICATIONS

Abstract in the abstract book of the International Conference: "Molecular mechanisms of genetic processes and biotechnology". Authors: Maria Kononova, Livia Stavolone and Thomas Hohn. Title: Cestrum Yellow Leaf—Curling Virus Promoter (CmYLCV) is a new strong constitutive promoter for broad variety of plants. Nov. 20, 2001. p. 220.

Abstract S22 in the abstract book of 10th IAPTC&B Congress "Plant Biotechnology 2002 and beyond." Authors: Masha Kononova, Livia Stavolone and Thomas Hohn. Title: Cestrum Yellow Leaf - Curling Virus Promoter (CmYLCV) is a new strong constitutive promoter for broad variety of plants. Jun. 24, 2002. p. 10-A.

Extended abstract in the proceedings of 10th IAPTC&B Congress "Plant Biotechnology 2002 and beyond." Authors: Masha Kononova, Livia Stavolone and Thomas Hohn. Title: Evaluation of constitutive Cestrum Yellow Leaf -Curling Virus Promoter (CmYLCV) in maize and tomato. p. 237-238. Jun. 24, 2002.

Manuscript submitted to Plant Molecular Biology Journal. Title: Cestrum yellow leaf curling virus (CmYLCV) promoter: a new strong constitutive promoter for heterologous gene expression in a wide variety of crops Livia Stavolone, Maria Kononova, Sandra Pauli, Antonio Ragozzino, Peter de Haan, Steve Milligan, Kay Lawton,and Thomas Hohn. Sep. 2003

*Primary Examiner*—James Ketter
(74) *Attorney, Agent, or Firm*—Michael E. Yates

(57) ABSTRACT

This invention describes novel DNA sequences that function as promoters of transcription of associated nucleotide sequences. More specifically, this invention describes DNA sequences conferring constitutive expression to an associated nucleotide sequence. The invention also describes recombinant sequences containing such promoter sequences. The said recombinant DNA sequences may be used to create transgenic plants, but especially plants expressing a nucleotide sequence of interest at all times and in most tissues and organs.

21 Claims, No Drawings

SEQUENCE LISTING

<160> NUMBER OF SEQ ID NOS: 49

<210> SEQ ID NO 1
<211> LENGTH: 670
<212> TYPE: DNA
<213> ORGANISM: Cestrum yellow leaf curling virus

<400> SEQUENCE: 1

```
attactggca gacaaagtgg cagacatact gtcccacaaa tgaagatgga atctgtaaaa      60
gaaaacgcgt gaaataatgc gtctgacaaa ggttaggtcg gctgccttta atcaatacca     120
aagtggtccc taccacgatg gaaaaactgt gcagtcggtt tggcttttc tgacgaacaa      180 ataagattcg tggccgacag gtgggggtcc accatgtgaa ggcatcttca gactccaata     240
atggagcaat gacgtaaggg cttacgaaat aagtaagggt agtttgggaa atgtccactc     300
acccgtcagt ctataaatac ttagcccctc cctcattgtt aagggagcaa aatctcagag     360
agatagtcct agagagagaa agagagcaag tagcctagaa gtagtcaagg cggcgaagta     420
ttcaggcagg gtggccagga agaagaaaag ccaagacgac gaaaacaggt aagagctaag     480
ctttctcatc tcaaagatga ttcttgatga tttttgtctc cacggtccgt ataggatcca     540
```

-continued

```
ctgaattgat aaatatcata tggtttgtat aaaacccgat atttaaatct gtatcattct     600
gtttgaataa aacttgatac tttgttggag tcgtttgtaa aacataaac aattataatc      660 tgttaaaaac                                                             670
```

<210> SEQ ID NO 2
<211> LENGTH: 346
<212> TYPE: DNA
<213> ORGANISM: Cestrum yellow leaf curling virus

<400> SEQUENCE: 2

```
ctggcagaca aagtggcaga catactgtcc cacaaatgaa gatggaatct gtaaaagaaa     60
acgcgtgaaa taatgcgtct gacaaaggtt aggtcggctg cctttaatca ataccaaagt    120
ggtccctacc acgatggaaa aactgtgcag tcggtttggc ttttctgac gaacaaataa     180 gattcgtggc cgacaggtgg gggtccacca tgtgaaggca tcttcagact ccaataatgg    240
agcaatgacg taagggctta cgaaataagt aagggtagtt tgggaaatgt ccactcaccc    300
gtcagtctat aaatacttag cccctccctc attgttaagg gagcaa                   346
```

<210> SEQ ID NO 3
<211> LENGTH: 400
<212> TYPE: DNA
<213> ORGANISM: Cestrum yellow leaf curling virus

<400> SEQUENCE: 3

```
ctggcagaca aagtggcaga catactgtcc cacaaatgaa gatggaatct gtaaaagaaa     60
acgcgtgaaa taatgcgtct gacaaaggtt aggtcggctg cctttaatca ataccaaagt    120
ggtccctacc acgatggaaa aactgtgcag tcggtttggc ttttctgac gaacaaataa     180 gattcgtggc cgacaggtgg gggtccacca tgtgaaggca tcttcagact ccaataatgg    240
agcaatgacg taagggctta cgaaataagt aagggtagtt tgggaaatgt ccactcaccc    300
gtcagtctat aaatacttag cccctccctc attgttaagg gagcaaaatc tcagagagat    360
agtcctagag agagaaagag agcaagtagc ctagaagtag                           400
```

<210> SEQ ID NO 4
<211> LENGTH: 634
<212> TYPE: DNA
<213> ORGANISM: Cestrum yellow leaf curling virus

<400> SEQUENCE: 4

```
ctggcagaca aagtggcaga catactgtcc cacaaatgaa gatggaatct gtaaaagaaa     60
acgcgtgaaa taatgcgtct gacaaaggtt aggtcggctg cctttaatca ataccaaagt    120
ggtccctacc acgatggaaa aactgtgcag tcggtttggc ttttctgac gaacaaataa     180 gattcgtggc cgacaggtgg gggtccacca tgtgaaggca tcttcagact ccaataatgg    240
agcaatgacg taagggctta cgaaataagt aagggtagtt tgggaaatgt ccactcaccc    300
gtcagtctat aaatacttag cccctccctc attgttaagg gagcaaaatc tcagagagat    360
agtcctagag agagaaagag agcaagtagc ctagaagtag tcaaggcggc gaagtattca    420
ggcagggtgg ccaggaagaa gaaaagccaa gacgacgaaa acaggtaaga gctaagcttt    480
ctcatctcaa agatgattct tgatgatttt tgtctccacg gtccgtatag gatccactga    540
attgataaat atcatatggt ttgtataaaa cccgatattt aaatctgtat cattctgttt    600
gaataaaact tgatactttg ttggagtcgt ttgt                                 634
```

<210> SEQ ID NO 5
<211> LENGTH: 32
<212> TYPE: DNA
<213> ORGANISM: Cestrum yellow leaf curling virus

<400> SEQUENCE: 5
aaaaacataa acaattataa tctgttaaaa ac       32

<210> SEQ ID NO 6
<211> LENGTH: 104
<212> TYPE: DNA
<213> ORGANISM: Cestrum yellow leaf curling virus

<400> SEQUENCE: 6
ggcacagctg tcagttgtgc aaatccgagt catctggacc acaaacatca gaagagggtc       60
tacaagagtc agaagacgaa gactttcgg tgctagttta atta       104

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 7
gaccacaaac atcagaag       18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 8
caaacttatt gggtaatc       18

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 9
cagggtacca ctaaaatcac c       21

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 10
aggggatccc caattcccc       19

<210> SEQ ID NO 11
<211> LENGTH: 21
<212> TYPE: DNA
<213> ORGANISM: Artificial Sequence -continued

```
<220> FEATURE:
<223> OTHER INFORMATION: Description of Artificial Sequence:
      oligonucleotide

<400> SEQUENCE: 11
aggggtacca tcgatatgga g                                              21

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 12
ttaggatccg ccctgccac                                                 19

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 13
cttctagaca aagtggcaga c                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 14
ttggtacctt aacaatgagg g                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 15
ctacttctag gtaccttgct c                                              21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 16
ttggtacctt aacaatgagg g                                              21

<210> SEQ ID NO 17
<211> LENGTH: 20
<212> TYPE: DNA
<213> ORGANISM: Artificial Sequence
<220> FEATURE:
```

<223> OTHER INFORMATION: Description of Artificial Sequence:
      oligonucleotide

<400> SEQUENCE: 17 gggatcccc agtctctctc                                                  20

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 18
gtgaattcga gctcggta                                                   18

<210> SEQ ID NO 19
<211> LENGTH: 668
<212> TYPE: DNA
<213> ORGANISM: Cestrum yellow leaf curling virus

<400> SEQUENCE: 19
attactggca gacaaagtgg cagacatact gtcccacaaa tgaagatgga atctgtaaaa      60
gaaaacgcgt gaataatgc gtctgacaaa ggttaggtcg gctgccttta atcaatacca     120
aagtggtccc taccacgatg gaaaaactgt gcagtcggtt tggcttttttc tgacgaacaa    180 ataagattcg tggccgacag gtggggggtcc accatgtgaa ggcatcttca gactccaata    240
atggagcaat gacgtaaggg cttacgaaat aagtaagggt agtttgggaa atgtccactc    300
acccgtcagt ctataaatac ttagcccctc cctcattgtt aagggagcaa atctcagag     360 agatagtcct agagagagaa agagagcaag tagcctagaa gtagtcaagg cggcgaagta    420
ttcaggcagg tggccaggaa gaagaaaagc caagacgacg aaaacaggta agagctaagc    480
tttctcatct caaagatgat tcttgatgat ttttgtctcc acggtccgta taggatcact    540
gaattgataa atatcatatg gtttgtataa aacccgatat ttaaatctgt atcattctgt    600
ttgaataaaa cttgatactt tgttggagtc gtttgtaaaa acataaacaa ttataatctg    660
ttaaaaac                                                             668

<210> SEQ ID NO 20
<211> LENGTH: 632
<212> TYPE: DNA
<213> ORGANISM: Cestrum yellow leaf curling virus

<400> SEQUENCE: 20
ctggcagaca aagtggcaga catactgtcc cacaaatgaa gatggaatct gtaaagaaa      60 acgcgtgaaa taatgcgtct gacaaaggtt aggtcggctg cctttaatca ataccaaagt    120
ggtccctacc acgatggaaa aactgtgcag tcggtttggc ttttttctgac gaacaaataa   180 gattcgtggc cgacaggtgg gggtccacca tgtgaaggca tcttcagact ccaataatgg    240
agcaatgacg taagggctta cgaaataagt aagggtagtt tgggaaatgt ccactcaccc    300
gtcagtctat aaatacttag cccctccctc attgttaagg gagcaaaatc tcagagagat    360
agtcctagag agaaagag agcaagtagc ctagaagtag tcaaggcggc gaagtattca    420
ggcaggtggc caggaagaag aaaagccaag acgacgaaaa caggtaagag ctaagctttc    480
tcatctcaaa gatgattctt gatgattttt gtctccacgg tccgtatagg atcactgaat    540
tgataaatat catatggttt gtataaaacc cgatatttaa atctgtatca ttctgtttga    600
ataaaacttg atactttgtt ggagtcgttt gt                                      632

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 21
cccgctgcag atcgttcaaa catttggc                                           28

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 22
cccgaagctt tctagagatc tagtaac                                            27

<210> SEQ ID NO 23
<211> LENGTH: 41
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 23
gggcggatcc gcatgcatgt cttaaggtaa gctcactaag g                            41

<210> SEQ ID NO 24
<211> LENGTH: 34
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 24
ccgcgctgca ggctgctttc aagcaagttc tgcg                                    34

<210> SEQ ID NO 25
<211> LENGTH: 35
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 25
ttgagagctc gtttaattac tggcagacaa agtgg                                   35

<210> SEQ ID NO 26
<211> LENGTH: 34
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 26

```
ttgactgcag gtttatgttt ttacaaacga ctcc                            34
```

<210> SEQ ID NO 27
<211> LENGTH: 137
<212> TYPE: DNA
<213> ORGANISM: Artificial Sequence
<220> FEATURE:
<223> OTHER INFORMATION: Description of Artificial Sequence: AGLINK
      multicloning site

<400> SEQUENCE: 27

```
gcggccgctc cggattcgaa ttaattaacg tacgaagctt gcatgcctgc agtgatcacc    60
atggtcgact ctagaggatc cccgggtacc gagctcgaat tcggcgcgcc caattgattt   120
aaatggccgc tgcggcc                                                  137
```

<210> SEQ ID NO 28
<211> LENGTH: 216
<212> TYPE: DNA
<213> ORGANISM: Artificial Sequence
<220> FEATURE:
<223> OTHER INFORMATION: Description of Artificial Sequence: BIGLINK
      multicloning site

<400> SEQUENCE: 28

```
ggccgcagcg gccatttaaa tcaattgggc gcgccgaatt cgagctcggt acccggggat    60
cctctagagt cgaccatggt gatcactgca ggcatgcaag cttcgtacgt taattaattc   120
gaatccggag cggccgcacg cgtgggcccg tttaaacctc gagagatctg ctagccctgc   180
aggaaattta ccggtgcccg gcggccagc atggcc                              216
```

<210> SEQ ID NO 29
<211> LENGTH: 28
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 29

```
cgcggatcct ggcagacaaa gtggcaga                                    28
```

<210> SEQ ID NO 30
<211> LENGTH: 26
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 30

```
cgcggatcct acttctaggc tacttg                                      26
```

<210> SEQ ID NO 31
<211> LENGTH: 7195
<212> TYPE: DNA
<213> ORGANISM: Artificial Sequence
<220> FEATURE:
<223> OTHER INFORMATION: Description of Artificial Sequence:
      vector pNOV2804

<400> SEQUENCE: 31

```
gtttacccgc caatatatcc tgtcaaacac tgatagttta aactgaaggc gggaaacgac    60
aatctgatca tgagcggaga attaagggag tcacgttatg accccgccg atgacgcggg   120
```

-continued

| | |
|---|---|
| acaagccgtt ttacgtttgg aactgacaga accgcaacgc tgcaggaatt ggccgcagcg | 180 |
| gccatttaaa tcaattgggc gcgtacgtag cactagtgcg cgatcgctta attaagcggc | 240 |
| gcgcctaaag cttgcatgcc tgcaggtcga ctctagagga tccccgatca tgcaaaaact | 300 |
| cattaactca gtgcaaaact atgcctgggg cagcaaaacg gcgttgactg aactttatgg | 360 |
| tatgaaaaat ccgtccagcc agccgatggc cgagctgtgg atgggcgcac atccgaaaag | 420 |
| cagttcacga gtgcagaatg ccgccggaga tatcgtttca ctgcgtgatg tgattgagag | 480 |
| tgataaatcg actctgctcg agaggccgt tgccaaacgc tttggcgaac tgcctttcct | 540 |
| gttcaaagta ttatgcgcag cacagccact ctccattcag gttcatccaa acaaacacaa | 600 |
| ttctgaaatc ggttttgcca agaaaatgc cgcaggtatc ccgatggatg ccgccgagcg | 660 |
| taactataaa gatcctaacc acaagccgga gctggttttt cgctgacgc ctttccttgc | 720 |
| gatgaacgcg tttcgtgaat tttccgagat tgtctcccta ctccagccgg tcgcaggtgc | 780 |
| acatccggcg attgctcact ttttacaaca gcctgatgcc gaacgtttaa gcgaactgtt | 840 |
| cgccagcctg ttgaatatgc agggtgaaga aaaatcccgc gcgctggcga ttttaaaatc | 900 |
| ggccctcgat agccagcagg gtgaaccgtg gcaaacgatt cgtttaattt ctgaattta | 960 |
| cccggaagac agcggtctgt tctccccgct attgctgaat gtggtgaaat tgaaccctgg | 1020 |
| cgaagcgatg ttcctgttcg ctgaaacacc gcacgcttac ctgcaaggcg tggcgctgga | 1080 |
| agtgatggca aactccgata cgtgctgcg tgcgggtctg acgcctaaat acattgatat | 1140 |
| tccggaactg gttgccaatg tgaaattcga agccaaaccg gctaaccagt tgttgaccca | 1200 |
| gccggtgaaa caaggtgcag aactggactt cccgattcca gtggatgatt ttgccttctc | 1260 |
| gctgcatgac cttagtgata agaaaccac cattagccag cagagtgccg ccattttgtt | 1320 |
| ctgcgtcgaa ggcgatgcaa cgttgtggaa aggttctcag cagttacagc ttaaaccggg | 1380 |
| tgaatcagcg tttattgccg ccaacgaatc accggtgact gtcaaaggcc acggccgttt | 1440 |
| agcgcgtgtt tacaacaagc tgtaagagct tactgaaaaa attaacatct cttgctaagc | 1500 |
| tgggagctct agatccccga atttccccga tcgttcaaac atttggcaat aaagtttctt | 1560 |
| aagattgaat cctgttgccg gtcttgcgat gattatcata taatttctgt tgaattacgt | 1620 |
| taagcatgta ataattaaca tgtaatgcat gacgttattt atgagatggg ttttatgat | 1680 |
| tagagtcccg caattataca tttaatacgc gatagaaaac aaaatatagc gcgcaaacta | 1740 |
| ggataaatta tcgcgcgcgg tgtcatctat gttactagat cgggaattgg gtaccatgcc | 1800 |
| cgggcggcca gcatggccgt atccgcaatg tgttattaag ttgtctaagc gtcaatttgt | 1860 |
| ttacaccaca atatatcctg ccaccagcca gccaacagct ccccgaccgg cagctcggca | 1920 |
| caaaatcacc actcgataca ggcagcccat cagaattaat tctcatgttt gacagcttat | 1980 |
| catcgactgc acgtgcacc aatgcttctg gcgtcaggca gccatcggaa gctgtggtat | 2040 |
| ggctgtgcag gtcgtaaatc actgcataat tcgtgtcgct caaggcgcac tcccgttctg | 2100 |
| gataatgttt tttgcgccga catcataacg gttctggcaa atattctgaa atgagctgtt | 2160 |
| gacaattaat catccggctc gtataatgtg tggaattgtg agcggataac aatttcacac | 2220 |
| aggaaacaga ccatgaggga agcgttgatc gccgaagtat cgactcaact atcagaggta | 2280 |
| gttggcgtca tcgagcgcca tctcgaaccg acgttgctgg ccgtacattt gtacggctcc | 2340 |
| gcagtggatg gcggcctgaa gccacacagt gatattgatt tgctggttac ggtgaccgta | 2400 |
| aggcttgatg aaacaacgcg cgcgagcttg atcaacgacc ttttggaaac ttcggcttcc | 2460 |
| cctggagaga gcgagattct ccgcgctgta gaagtcacca ttgttgtgca cgacgacatc | 2520 |

```
attccgtggc gttatccagc taagcgcgaa ctgcaatttg gagaatggca gcgcaatgac    2580
attcttgcag gtatcttcga gccagccacg atcgacattg atctggctat cttgctgaca    2640
aaagcaagag aacatagcgt tgccttggta ggtccagcgg cggaggaact ctttgatccg    2700
gttcctgaac aggatctatt tgaggcgcta atgaaacct taacgctatg gaactcgccg    2760
cccgactggg ctggcgatga gcgaaatgta gtgcttacgt tgtcccgcat ttggtacagc    2820
gcagtaaccg gcaaaatcgc gccgaaggat gtcgctgccg actgggcaat ggagcgcctg    2880
ccggcccagt atcagcccgt catacttgaa gctaggcagg cttatcttgg acaagaagat    2940
cgcttggcct cgcgcgcaga tcagttggaa gaatttgttc actacgtgaa aggcgagatc    3000
accaaagtag tcggcaaata aagtctagt ggatctccgt accccgggg gatctggctc    3060 gcggcggacg cacgacgccg gggcgagacc ataggcgatc tcctaaatca atagtagctg    3120
taacctcgaa gcgtttcact tgtaacaacg attgagaatt tttgtcataa aattgaaata    3180
cttggttcgc atttttgtca tccgcggtca gccgcaattc tgacgaactg cccatttagc    3240
tggagatgat tgtacatcct tcacgtgaaa atttctcaag cgctgtgaac aagggttcag    3300
attttagatt gaaaggtgag ccgttgaaac acgttcttct tgtcgatgac gacgtcgcta    3360
tgcggcatct tattattgaa taccttacga tccacgcctt caaagtgacc gcggtagccg    3420
acagcaccca gttcacaaga gtactctctt ccgcgacggt cgatgtcgtg gttgttgatc    3480
taaatttagg tcgtgaagat gggctcgaga tcgttcgtaa tctggcggca aagtctgata    3540
ttccaatcat aattatcagt ggcgaccgcc ttgaggagac ggataaagtt gttgcactcg    3600
agctaggagc aagtgatttt atcgctaagc cgttcagtat cagagagttt ctagcacgca    3660 ttcggttgc cttgcgcgtg cgccccaacg ttgtccgctc caaagaccga cggtctttt     3720 gttttactga ctggacactt aatctcaggc aacgtcgctt gatgtccgaa gctggcggtg    3780
aggtgaaact tacggcaggt gagttcaatc ttctcctcgc gtttttagag aaaccccgcg    3840
acgttctatc gcgcgagcaa cttctcattg ccagtcgagt acgcgacgag gaggtttatg    3900
acaggagtat agatgttctc attttgaggc tgcgccgcaa acttgaggca gatccgtcaa    3960
gccctcaact gataaaaaca gcaagaggtg ccggttattt ctttgacgcg gacgtgcagg    4020
tttcgcacgg ggggacgatg gcagcctgag ccaattccca gatccccgag gaatcggcgt    4080
gagcggtcgc aaaccatccg gcccggtaca aatcggcgcg gcgctgggtg atgacctggt    4140
ggagaagttg aaggccgcgc aggccgccca gcggcaacgc atcgaggcag aagcacgccc    4200
cggtgaatcg tggcaagcgg ccgctgatcg aatccgcaaa gaatcccggc aaccgccggc    4260
agccggtgcg ccgtcgatta ggaagccgcc caagggcgac gagcaaccag atttttcgt    4320 tccgatgctc tatgacgtgg gcacccgcga tagtcgcagc atcatggacg tggccgtttt    4380
ccgtctgtcg aagcgtgacc gacgagctgg cgaggtgatc cgctacgagc ttccagacgg    4440
gcacgtagag gtttccgcag gccggccgg catggccagt gtgtgggatt acgacctggt    4500
actgatggcg gtttcccatc taaccgaatc catgaaccga taccgggaag ggaagggaga    4560
caagcccggc cgcgtgttcc gtccacacgt tgcggacgta ctcaagttct gccggcgagc    4620
cgatggcgga aagcagaaag acgacctggt agaaacctgc attcggttaa acaccacgca    4680
cgttgccatg cagcgtacga agaaggccaa gaacggccgc ctggtgacgg tatccgaggg    4740
tgaagccttg attagccgct acaagatcgt aaagagcgaa accggcggc cggagtacat    4800 cgagatcgag ctagctgatt ggatgtaccg cgagatcaca gaaggcaaga acccggacgt    4860
```

```
gctgacggtt cacccccgatt acttttttgat cgatcccggc atcggccgtt ttctctaccg   4920
cctggcacgc cgcgccgcag gcaaggcaga agccagatgg ttgttcaaga cgatctacga   4980
acgcagtggc agcgccggag agttcaagaa gttctgtttc accgtgcgca agctgatcgg   5040
gtcaaatgac ctgccggagt acgatttgaa ggaggaggcg gggcaggctg gcccgatcct   5100
agtcatgcgc taccgcaacc tgatcgaggg cgaagcatcc gccggttcct aatgtacgga   5160
gcagatgcta gggcaaattg ccctagcagg ggaaaaaggt cgaaaaggtc tctttcctgt   5220
ggatagcacg tacattggga acccaaagcc gtacattggg aaccggaacc cgtacattgg   5280
gaacccaaag ccgtacattg ggaaccggtc acacatgtaa gtgactgata taaaagagaa   5340
aaaaggcgat ttttccgcct aaaactcttt aaaacttatt aaaactctta aacccgcct    5400
ggcctgtgca taactgtctg gccagcgcac agccgaagag ctgcaaaaag cgcctaccct   5460
tcggtcgctg cgctccctac gccccgccgc ttcgcgtcgg cctatcgcgg ccgctggccg   5520
ctcaaaaatg gctggcctac ggccaggcaa tctaccaggg cgcggacaag ccgcgccgtc   5580
gccactcgac cgccggcgct gaggtctgcc tcgtgaagaa ggtgttgctg actcatacca   5640
ggcctgaatc gccccatcat ccagccagaa agtgagggag ccacggttga tgagagcttt   5700
gttgtaggtg gaccagttgg tgatttttgaa cttttgcttt gccacggaac ggtctgcgtt   5760
gtcgggaaga tgcgtgatct gatccttcaa ctcagcaaaa gttcgattta ttcaacaaag   5820
ccgccgtccc gtcaagtcag cgtaatgctc tgccagtgtt acaaccaatt aaccaattct   5880
gattagaaaa actcatcgag catcaaatga aactgcaatt tattcatatc aggattatca   5940
ataccatatt tttgaaaaag ccgtttctgt aatgaaggag aaaactcacc gaggcagttc   6000
cataggatgg caagatcctg gtatcggtct gcgattccga ctcgtccaac atcaatacaa   6060
cctattaatt tcccctcgtc aaaaataagg ttatcaagtg agaaatcacc atgagtgacg   6120
actgaatccg gtgagaatgg caaaagctct gcattaatga atcggccaac gcgcggggag   6180
aggcggtttg cgtattgggc gctcttccgc ttcctcgctc actgactcgc tgcgctcggt   6240
cgttcggctg cggcgagcgg tatcagctca ctcaaaggcg gtaatacggt tatccacaga   6300
atcagggggat aacgcaggaa agaacatgtg agcaaaaggc cagcaaaagg ccaggaaccg   6360
taaaaaggcc gcgttgctgg cgtttttcca taggctccgc ccccctgacg agcatcacaa   6420
aaatcgacgc tcaagtcaga ggtggcgaaa cccgacagga ctataaagat accaggcgtt   6480
tcccccctgga agctccctcg tgcgctctcc tgttccgacc ctgccgctta ccggatacct   6540
gtccgccttt ctcccttcgg gaagcgtggc gctttctcat agctcacgct gtaggtatct   6600
cagttcggtg taggtcgttc gctccaagct gggctgtgtg cacgaacccc ccgttcagcc   6660
cgaccgctgc gccttatccg gtaactatcg tcttgagtcc aacccggtaa gacacgactt   6720
atcgccactg gcagcagcca ctggtaacag gattagcaga gcgaggtatg taggcggtgc   6780
tacagagttc ttgaagtggt ggcctaacta cggctacact agaagaacag tatttggtat   6840
ctgcgctctg ctgaagccag ttaccttcgg aaaaagagtt ggtagctctt gatccggcaa   6900
acaaaccacc gctggtagcg gtggtttttt tgtttgcaag cagcagatta cgcgcagaaa   6960
aaaaggatct caagaagatc ctttgatctt ttctacgggg tctgacgctc agtggaacga   7020
aaactcacgt taagggattt tggtcatgag attatcaaaa aggatcttca cctagatcct   7080
tttgatccgg aattaattcc tgtggttggc atgcacatac aaatggacga acggataaac   7140
cttttcacgc ccttttaaat atccgattat tctaataaac gctctttttct cttag         7195
```

<210> SEQ ID NO 32
<211> LENGTH: 4224
<212> TYPE: DNA
<213> ORGANISM: Artificial Sequence
<220> FEATURE:
<223> OTHER INFORMATION: Description of Artificial Sequence:
      vector pNOV3604

<400> SEQUENCE: 32

```
agcttgcatg cctgcaggtc gactctagag gatccccgat catgcaaaaa ctcattaact      60
cagtgcaaaa ctatgcctgg ggcagcaaaa cggcgttgac tgaactttat ggtatggaaa     120
atccgtccag ccagccgatg gccgagctgt ggatgggcgc acatccgaaa agcagttcac     180
gagtgcagaa tgccgccgga gatatcgttt cactgcgtga tgtgattgag agtgataaat     240
cgactctgct cggagaggcc gttgccaaac gctttggcga actgcctttc ctgttcaaag     300
tattatgcgc agcacagcca ctctccattc aggttcatcc aaacaaacac aattctgaaa     360
tcggttttgc caaagaaaat gccgcaggta tcccgatgga tgccgccgag cgtaactata     420
aagatcctaa ccacaagccg agctggtttt tgcgctgac gcctttcctt gcgatgaacg     480
cgtttcgtga atttccgag attgtctccc tactccagcc ggtcgcaggt gcacatccgg     540
cgattgctca cttttacaa cagcctgatg ccgaacgttt aagcgaactg ttcgccagcc     600
tgttgaatat gcagggtgaa gaaaaatccc gcgcgctggc gattttaaaa tcggccctcg     660
atagccagca gggtgaaccg tgcaaacga ttcgtttaat ttctgaattt tacccggaag     720
acagcggtct gttctccccg ctattgctga atgtggtgaa attgaaccct ggcgaagcga     780
tgttcctgtt cgctgaaaca ccgcacgctt acctgcaagg cgtggcgctg aagtgatgg     840
caaactccga taacgtgctg cgtgcgggtc tgacgcctaa atacattgat attccggaac     900
tggttgccaa tgtgaaattc gaagccaaac cggctaacca gttgttgacc cagccggtga     960
aacaaggtgc agaactggac ttcccgattc cagtggatga ttttgccttc tcgctgcatg    1020
accttagtga taaagaaacc accattagcc agcagagtgc cgccattttg ttctgcgtcg    1080
aaggcgatgc aacgttgtgg aaaggttctc agcagttaca gcttaaaccg ggtgaatcag    1140
cgtttattgc cgccaacgaa tcaccggtga ctgtcaaagg ccacggccgt ttagcgcgtg    1200
tttacaacaa gctgtaagag cttactgaaa aaattaacat ctcttgctaa gctgggagct    1260
ctagatcccc gaatttcccc gatcgttcaa acatttggca ataaagtttc ttaagattga    1320
atcctgttgc cggtcttgcg atgattatca tataatttct gttgaattac gttaagcatg    1380
taataattaa catgtaatgc atgacgttat ttatgagatg gttttttatg attagagtcc    1440
cgcaattata catttaatac gcgatagaaa acaaaatata gcgcgcaaac taggataaat    1500
tatcgcgcgc ggtgtcatct atgttactag atcgggaatt gggtaccgaa ttcactggcc    1560
gtcgttttac aacgtcgtga ctgggaaaac cctggcgtta cccaacttaa tcgccttgca    1620
gcacatcccc ctttcgccag ctggcgtaat agcgaagagg cccgcaccga tcgcccttcc    1680
caacagttgc gcagcctgaa tggcgaatgg cgcctgatgc ggtatttct ccttacgcat    1740
ctgtgcggta tttcacaccg catatggtgc actctcagta caatctgctc tgatgccgca    1800
tagttaagcc agccccgaca cccgccaaca cccgctgacg cgccctgacg gcttgtctg    1860
ctcccggcat ccgcttacag acaagctgtg accgtctccg ggagctgcat gtgtcagagg    1920
ttttcaccgt catcaccgaa acgcgcgaga cgaaagggcc tcgtgatacg cctattttta    1980
taggttaatg tcatgataat aatggtttct tagacgtcag gtggcacttt tcggggaaat    2040
gtgcgcggaa cccctatttg tttatttttc taaatacatt caaatatgta tccgctcatg    2100
```

-continued

```
agacaataac cctgataaat gcttcaatgg cgcgccgcgg ccgcttaaga atattgaaaa    2160
aggaagagta tgagtattca acatttccgt gtcgccctta ttccctttttt tgcggcattt    2220 tgccttcctg ttttttgctca cccagaaacg ctggtgaaag taaaagatgc tgaagatcag    2280
ttgggtgcac gagtgggtta catcgaactg gatctcaaca gcggtaagat ccttgagagt    2340
tttcgccccg aagaacgttt tccaatgatg agcacttttta aagttctgct atgtggcgcg    2400
gtattatccc gtattgacgc cgggcaagag caactcggtc gccgcataca ctattctcag    2460
aatgacttgg ttgagtactc accagtcaca gaaaagcatc ttacgatggc atgacagta    2520 agagaattat gcagtgctgc cataaccatg agtgataaca ctgcggccaa cttacttctg    2580
acaacgatcg gaggaccgaa ggagctaacc gcttttttgc acaacatggg ggatcatgta    2640
actcgccttg atcgttggga accggagctg aatgaagcca taccaaacga cgagcgtgac    2700
accacgatgc ctgtagcaat ggcaacaacg ttgcgcaaac tattaactgg cgaactactt    2760
actctagctt cccggcaaca attaatagac tggatggagg cggataaagt tgcaggacca    2820
cttctgcgct cggcccttcc ggctggctgg tttattgctg ataaatctgg agccggtgag    2880
cgtgggtctc gcggtatcat tgcagcactg gggccagatg gtaagccctc ccgtatcgta    2940
gttatctaca cgacggggag tcaggcaact atggatgaac gaaatagaca gatcgctgag    3000
ataggtgcct cactgattaa gcattggtaa ctgtcagacc aagtttactc atatatactt    3060
tagattgatt taaaacttca ttttttaattt aaaaggatct aggtgaagat ccttttttgat    3120 aatctcatga ccaaaatccc ttaacgtgag ttttcgttcc actgagcgtc agacccgta    3180 gaaaagatca aaggatcttc ttgagatcct ttttttctgc gcgtaatctg ctgcttgcaa    3240
acaaaaaaac caccgctacc agcggtggtt tgtttgccgg atcaagagct accaactctt    3300
tttccgaagg taactggctt cagcagagcg cagataccaa atactgtcct tctagtgtag    3360
ccgtagttag gccaccactt caagaactct gtagcaccgc ctacatacct cgctctgcta    3420
atcctgttac cagtggctgc tgccagtggc gataagtcgt gtcttaccgg gttggactca    3480
agacgatagt taccggataa ggcgcagcgg tcgggctgaa cggggggttc gtgcacacag    3540
cccagcttgg agcgaacgac ctacaccgaa ctgagatacc tacagcgtga gctatgagaa    3600
agcgccacgc ttcccgaagg gagaaaggcg gacaggtatc cggtaagcgg cagggtcgga    3660
acaggagagc gcacgaggga gcttccaggg ggaaacgcct ggtatcttta tagtcctgtc    3720
gggtttcgcc acctctgact tgagcgtcga ttttttgtgat gctcgtcagg ggggcggagc    3780
ctatggaaaa acgccagcaa cgcggccttt ttacggttcc tggccttttg ctggcctttt    3840
gctcacatgt tctttcctgc gttatcccct gattctgtgg ataaccgtat taccgccttt    3900
gagtgagctg ataccgctcg ccgcagccga acgaccgagc gcagcgagtc agtgagcgag    3960
gaagcggaag agcttaagcg gccgcggcgc ccgcccaat acgcaaaccg cctctccccg    4020
cgcgttggcc gattcattaa tgcagctggc acgacaggtt tcccgactgg aaagcgggca    4080
gtgagcgcaa cgcaattaat gtgagttagc tcactcatta ggcacccag gctttacact    4140 ttatgcttcc ggctcgtatg ttgtgtggaa ttgtgagcgg ataacaattt cacacaggaa    4200
acagctatga ccatgattac gcca                                          4224
```

<210> SEQ ID NO 33
<211> LENGTH: 21
<212> TYPE: DNA
<213> ORGANISM: Artificial Sequence
<220> FEATURE:

<223> OTHER INFORMATION: Description of Artificial Sequence:
      oligonucleotide

<400> SEQUENCE: 33
ccatcgtggt atttggtatt g                                         21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 34
caataccaaa taccacgatg g                                         21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 35
cgtggtagcg agcactttgg t                                         21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 36
aagtgctcgc taccacgatg g                                         21

<210> SEQ ID NO 37
<211> LENGTH: 912
<212> TYPE: DNA
<213> ORGANISM: Artificial
<220> FEATURE:
<223> OTHER INFORMATION: artificial sequence synthetic GFP gene with
      intron

<400> SEQUENCE: 37
atgagcaagg gcgaggagct gttcaccggc gtggtgccaa tcctggtgga gctggacggc      60
gacgtgaacg gccacaagtt cagcgtgagc ggcgagggcg agggcgacgc gacctacggc     120
aagctgaccc tgaagttcat ctgtaccacc ggcaagctcc cggtcccgtg gccgaccctg     180
gtgaccacct tcacctacgg cgtgcagtgt ttcagccgct acccggacca catgaagcgc     240
cacgacttct tcaagagcgc catgccggag ggctacgtaa gtttctgctt ctacctttga     300
tatatatata ataattatca ttaattagta gtaatataat atttcaaata ttttttttcaa     360 aataaaagaa tgtagtatat agcaattgct tttctgtagt ttataagtgt gtatatttta     420
atttataact tttctaatat atgaccaaaa tttgttgatg tgcaggtgca ggagcgcacc     480
atcagcttca aggacgacgg caactacaag acccgcgccg aggtgaagtt cgagggcgac     540
acactagtga accgcatcga gctgaagggc atcgacttca aggaggacgg caacatcctg     600
ggccacaagc tggagtacaa ctacaacagc cacaacgtgt acatcaccgc ggacaagcag     660

-continued

| | |
|---|---|
| aagaacggca tcaaggcgaa cttcaagatc cgccacaaca tcgaggacgg cagcgtgcag | 720 |
| ctggccgacc actaccagca gaacaccccg atcggcgacg tcctgtgct gctgccggac | 780 |
| aaccactacc tgagcaccca gagcgccctg agcaaggacc cgaacgagaa gcgcgaccac | 840 |
| atggtgctgc tggagttcgt gaccgccgcc ggcatcaccc acggcatgga cgagctgtac | 900 |
| aaggttaact ag | 912 |

<210> SEQ ID NO 38
<211> LENGTH: 2001
<212> TYPE: DNA
<213> ORGANISM: Artificial
<220> FEATURE:
<223> OTHER INFORMATION: artificial sequence GUS gene with intron

<400> SEQUENCE: 38

| | |
|---|---|
| atggtccgtc ctgtagaaac cccaacccgt gaaatcaaaa aactcgacgg cctgtgggca | 60 |
| ttcagtctgg atcgcgaaaa ctgtggaatt gatcagcgtt ggtgggaaag cgcgttacaa | 120 |
| gaaagccggg caattgctgt gccaggcagt tttaacgatc agttcgccga tgcagatatt | 180 |
| cgtaattatg cggcaacgt ctggtatcag cgcgaagtct ttataccgaa aggttgggca | 240 |
| ggccagcgta tcgtgctgcg tttcgatgcg gtcactcatt acggcaaagt gtgggtcaat | 300 |
| aatcaggaag tgatggagca tcagggcggc tatacgccat ttgaagccga tgtcacgccg | 360 |
| tatgttattg ccgggaaaag tgtacgtaag tttctgcttc tacctttgat atatatataa | 420 |
| taattatcat taattagtag taatataata tttcaaatat tttttcaaa ataaaagaat | 480 |
| gtagtatata gcaattgctt ttctgtagtt tataagtgtg tatattttaa tttataactt | 540 |
| ttctaatata tgaccaaaat ttgttgatgt gcaggtatca ccgtttgtgt gaacaacgaa | 600 |
| ctgaactggc agactatccc gccgggaatg gtgattaccg acgaaaacgg caagaaaaag | 660 |
| cagtcttact tccatgattt ctttaactat gccggaatcc atcgcagcgt aatgctctac | 720 |
| accacgccga acacctgggt ggacgatatc accgtggtga cgcatgtcgc gcaagactgt | 780 |
| aaccacgcgt ctgttgactg gcaggtggtg gccaatggtg atgtcagcgt tgaactgcgt | 840 |
| gatgcggatc aacaggtggt tgcaactgga caaggcacta gcgggacttt gcaagtggtg | 900 |
| aatccgcacc tctggcaacc gggtgaaggt tatctctatg aactgtgcgt cacagccaaa | 960 |
| agccagacag agtgtgatat ctacccgctt cgcgtcggca tccggtcagt ggcagtgaag | 1020 |
| ggcgaacagt tcctgattaa ccacaaaccg ttctacttta ctggctttgg tcgtcatgaa | 1080 |
| gatgcggact tgcgtggcaa aggattcgat aacgtgctga tggtgcacga ccacgcatta | 1140 |
| atggactgga ttgggccaa ctcctaccgt acctcgcatt acccttacgc tgaagagatg | 1200 |
| ctcgactggg cagatgaaca tggcatcgtg gtgattgatg aaactgctgc tgtcggcttt | 1260 |
| aacctctctt taggcattgg tttcgaagcg ggcaacaagc cgaaagaact gtacagcgaa | 1320 |
| gaggcagtca acgggaaac tcagcaagcg cacttacagg cgattaaaga gctgatagcg | 1380 |
| cgtgacaaaa accacccaag cgtggtgatg tggagtattg ccaacgaacc ggatacccgt | 1440 |
| ccgcaaggtg cacgggaata tttcgcgcca ctggcggaag caacgcgtaa actcgacccg | 1500 |
| acgcgtccga tcacctgcgt caatgtaatg ttctgcgacg ctcacaccga taccatcagc | 1560 |
| gatctctttg atgtgctgtg cctgaaccgt tattacggat ggtatgtcca aagcggcgat | 1620 |
| ttggaaacgg cagagaaggt actggaaaaa gaacttctgg cctggcagga gaaactgcat | 1680 |
| cagccgatta tcatcaccga atacggcgtg gatacgttag ccgggctgca ctcaatgtac | 1740 |
| accgacatgt ggagtgaaga gtatcagtgt gcatggctgg atatgtatca ccgcgtcttt | 1800 |

```
gatcgcgtca gcgccgtcgt cggtgaacag gtatggaatt tcgccgattt tgcgacctcg    1860
caaggcatat tgcgcgttgg cggtaacaag aaagggatct tcactcgcga ccgcaaaccg    1920
aagtcggcgg cttttctgct gcaaaaacgc tggactggca tgaacttcgg tgaaaaaccg    1980
cagcagggag gcaaacaatg a                                              2001
```

```
<210> SEQ ID NO 39
<211> LENGTH: 26
<212> TYPE: DNA
<213> ORGANISM: Artificial
<220> FEATURE:
<223> OTHER INFORMATION: artificial sequence PCR primer

<400> SEQUENCE: 39
cgcggattgc tcccttaaca atgagg                                         26
```

```
<210> SEQ ID NO 40
<211> LENGTH: 1618
<212> TYPE: DNA
<213> ORGANISM: Artificial
<220> FEATURE:
<223> OTHER INFORMATION: artificial sequence CmpS-synGFPI-nos expression
      cassette

<400> SEQUENCE: 40
tcctggcaga caaagtggca gacatactgt cccacaaatg aagatggaat ctgtaaaaga    60
aaacgcgtga ataatgcgt ctgacaaagg ttaggtcggc tgcctttaat caataccaaa    120
gtggtcccta ccacgatgga aaaactgtgc agtcggtttg gcttttcctg acgaacaaat    180
aagattcgtg gccgacaggt gggggtccac catgtgaagg catcttcaga ctccaataat    240
ggagcaatga cgtaagggct tacgaaataa gtaagggtag tttgggaaat gtccactcac    300
ccgtcagtct ataaatactt agcccctccc tcattgttaa gggagcaaaa tctcagagag    360
atagtcctag agagagaaag agagcaagta gcctagaagt aggatccacc atgctgcaga    420
tgagcaaggg cgaggagctg ttcaccggcg tggtgccaat cctggtggag ctggacggcg    480
acgtgaacgg ccacaagttc agcgtgagcg gcgagggcga gggcgacgcg acctacggca    540
agctgaccct gaagttcatc tgtaccaccg gcaagctccc ggtcccgtgg ccgaccctgg    600
tgaccacctt cacctacggc gtgcagtgtt tcagccgcta cccggaccac atgaagcgcc    660
acgacttctt caagagcgcc atgccggagg gctacgtaag tttctgcttc tacctttgat    720
atatatataa taattatcat taattagtag taatataata tttcaaatat ttttttcaaa    780
ataaaagaat gtagtatata gcaattgctt ttctgtagtt tataagtgtg tatatttaa    840 tttataactt ttctaatata tgaccaaaat tgttgatgt gcaggtgcag gagcgcacca    900
tcagcttcaa ggacgacggc aactacaaga cccgcgccga ggtgaagttc gagggcgaca    960
cactagtgaa ccgcatcgag ctgaagggca tcgacttcaa ggaggacggc aacatcctgg    1020
gccacaagct ggagtacaac tacaacagcc acaacgtgta catcaccgcg gacaagcaga    1080
agaacggcat caaggcgaac ttcaagatcc gccacaacat cgaggacggc agcgtgcagc    1140
tggccgacca ctaccagcag aacacccga tcggcgacgg tcctgtgctg ctgccggaca    1200
accactacct gagcacccag agcgccctga gcaaggaccc gaacgagaag cgcgaccaca    1260
tggtgctgct ggagttcgtg accgccgccg gcatcaccca cggcatggac gagctgtaca    1320
aggttaacta gagctcaaga tcccccgaat tccccgatc gttcaaacat ttggcaataa    1380
agtttcttaa gattgaatcc tgttgccggt cttgcgatga ttatcatcta atttctgttg    1440
```

-continued

```
aattacgtta agcatgtaat aattaacatg taatgcatga cgttatttat gagatgggtt    1500
tttatgatta gagtcccgca attatacatt taatacgcga tagaaaacaa aatatagcgc    1560
gcaaactagg ataaattatc gcgcgcggtg tcatctatgt tactagatcc gggaattg     1618
```

<210> SEQ ID NO 41
<211> LENGTH: 2730
<212> TYPE: DNA
<213> ORGANISM: Artificial
<220> FEATURE:
<223> OTHER INFORMATION: artificial sequence CmpS-GIG-nos expression cassette

<400> SEQUENCE: 41

```
aggatcctgg cagacaaagt ggcagacata ctgtcccaca aatgaagatg gaatctgtaa      60
aagaaaacgc gtgaaataat gcgtctgaca aaggttaggt cggctgcctt taatcaatac     120
caaagtggtc cctaccacga tgaaaaaact gtgcagtcgg tttggctttt tctgacgaac     180
aaataagatt cgtggccgac aggtgggggt ccaccatgtg aaggcatctt cagactccaa     240
taatggagca atgacgtaag ggcttacgaa ataagtaagg gtagtttggg aaatgtccac     300
tcacccgtca gtctataaat acttagcccc tccctcattg ttaagggagc aaaatctcag     360
agagatagtc ctagagagag aaagagagca agtagcctag aagtaggatc ccctcgaggt     420
cgaccatggt ccgtcctgta gaaaccccaa cccgtgaaat caaaaaactc gacggcctgt     480
gggcattcag tctggatcgc gaaaactgtg gaattgatca cgttggtgg gaaagcgcgt      540 tacaagaaag ccgggcaatt gctgtgccag gcagttttaa cgatcagttc gccgatgcag     600
atattcgtaa ttatgcgggc aacgtctggt atcagcgcga agtctttata ccgaaaggtt     660
gggcaggcca gcgtatcgtg ctgcgtttcg atgcggtcac tcattacggc aaagtgtggg     720
tcaataatca ggaagtgatg gagcatcagg gcggctatac gccatttgaa gccgatgtca     780
cgccgtatgt tattgccggg aaaagtgtac gtaagttttct gcttctacct ttgatatata     840
tataataatt atcattaatt agtagtaata taatatttca aatattttt tcaaaataaa      900 agaatgtagt atatagcaat tgcttttctg tagtttataa gtgtgtatat tttaatttat     960
aacttttcta atatatgacc aaaatttgtt gatgtgcagg tatcaccgtt tgtgtgaaca    1020
acgaactgaa ctggcagact atcccgccgg gaatggtgat taccgacgaa aacggcaaga    1080
aaaagcagtc ttacttccat gatttcttta actatgccgg aatccatcgc agcgtaatgc    1140
tctacaccac gccgaacacc tgggtggacg atatcaccgt ggtgacgcat gtcgcgcaag    1200
actgtaacca cgcgtctgtt gactggcagg tggtggccaa tggtgatgtc agcgttgaac    1260
tgcgtgatgc ggatcaacag gtggttgcaa ctggacaagg cactagcggg actttgcaag    1320
tggtgaatcc gcacctctgg caaccgggtg aaggttatct ctatgaactg tgcgtcacag    1380
ccaaaagcca gacagagtgt gatatctacc cgcttcgcgt cggcatccgg tcagtggcag    1440
tgaagggcga acagttcctg attaaccaca aaccgttcta ctttactggc tttggtcgtc    1500
atgaagatgc ggacttgcgt ggcaaaggat tcgataacgt gctgatggtg cacgaccacg    1560
cattaatgga ctggattggg gccaactcct accgtacctc gcattaccct tacgctgaag    1620
agatgctcga ctgggcagat gaacatggca tcgtggtgat tgatgaaact gctgctgtcg    1680
gctttaacct ctctttaggc attggtttcg aagcgggcaa caagccgaaa gaactgtaca    1740
gcgaagaggc agtcaacggg gaaactcagc aagcgcactt acaggcgatt aaagagctga    1800
tagcgcgtga caaaaaccac ccaagcgtgg tgatgtggag tattgccaac gaaccggata    1860
```

```
cccgtccgca aggtgcacgg gaatatttcg cgccactggc ggaagcaacg cgtaaactcg      1920
acccgacgcg tccgatcacc tgcgtcaatg taatgttctg cgacgctcac accgatacca      1980
tcagcgatct ctttgatgtg ctgtgcctga accgttatta cggatggtat gtccaaagcg      2040
gcgatttgga aacggcagag aaggtactgg aaaagaact tctggcctgg caggagaaac       2100
tgcatcagcc gattatcatc accgaatacg gcgtggatac gttagccggg ctgcactcaa      2160
tgtacaccga catgtggagt gaagagtatc agtgtgcatg gctggatatg tatcaccgcg      2220
tctttgatcg cgtcagcgcc gtcgtcggtg aacaggtatg gaatttcgcc gattttgcga      2280
cctcgcaagg catattgcgc gttggcggta acaagaaagg gatcttcact cgcgaccgca      2340
aaccgaagtc ggcggctttt ctgctgcaaa acgctggac tggcatgaac ttcggtgaaa        2400
aaccgcagca gggaggcaaa caatgaatca acaactctcc tggcgcacca tcgtcggcta      2460
cagcctcggg aattagatcc ccgaatttcc ccgatcgttc aaacatttgg caataaagtt      2520
tcttaagatt gaatcctgtt gccggtcttg cgatgattat catataatt ctgttgaatt        2580 acgttaagca tgtaataatt aacatgtaat gcatgacgtt atttatgaga tgggttttta      2640
tgattagagt cccgcaatta tacatttaat acgcgataga aaacaaaata tagcgcgcaa      2700
actaggataa attatcgcgc gcggtgtcat                                        2730
```

<210> SEQ ID NO 42
<211> LENGTH: 1577
<212> TYPE: DNA
<213> ORGANISM: Artificial
<220> FEATURE:
<223> OTHER INFORMATION: artificial sequence CmpC-synGFPI-nos expression
    cassette

<400> SEQUENCE: 42

```
tggcagacaa agtggcagac atactgtccc acaaatgaag atggaatctg taaaagaaaa        60
cgcgtgaaat aatgcgtctg acaaaggtta ggtcggctgc ctttaatcaa taccaaagtg      120
gtccctacca cgatggaaaa actgtgcagt cggtttggct ttttctgacg aacaaataag      180
attcgtggcc gacaggtggg ggtccaccat gtgaaggcat cttcagactc caataatgga      240
gcaatgacgt aagggcttac gaaataagta agggtagttt gggaaatgtc cactcacccg      300
tcagtctata aatacttagc ccctccctca ttgttaaggg agcaacgatc cgcgaagggc      360
gaattcgttt aaacctgcag atgagcaagg gcgaggagct gttcaccggc gtggtgccaa      420
tcctggtgga gctggacggc gacgtgaacg gccacaagtt cagcgtgagc ggcgagggcg      480
agggcgacgc gacctacggc aagctgaccc tgaagttcat ctgtaccacc ggcaagctcc      540
cggtcccgtg gccgaccctg gtgaccacct tcacctacgg cgtgcagtgt tcagccgct       600 acccggacca catgaagcgc cacgacttct tcaagagcgc catgccggag ggctacgtaa      660
gtttctgctt ctacctttga tatatatata ataattatca ttaattagta gtaatataat      720
atttcaaata tttttttcaa aataaagaa tgtagtatat agcaattgct tttctgtagt        780
ttataagtgt gtatatttta atttataact tttctaatat atgaccaaaa tttgttgatg      840
tgcaggtgca ggagcgcacc atcagcttca aggacgacgg caactacaag acccgcgccg      900
aggtgaagtt cgagggcgac acactagtga accgcatcga gctgaagggc atcgacttca      960
aggaggacgg caacatcctg ggccacaagc tggagtacaa ctacaacagc cacaatgtgt      1020
acatcaccgc ggacaagcag aagaacggca tcaaggcgaa cttcaagatc cgccacaata      1080
tcgaggacgg cagcgtgcag ctggccgacc actaccagca gaacacccccg atcggcgacg      1140
```

-continued

```
gtcctgtgct gctgccggac aaccactacc tgagcaccca gagcgccctg agcaaggacc      1200
cgaacgagaa gcgcgaccac atggtgctgc tggagttcgt gaccgccgcc ggcatcaccc      1260
acggcatgga cgagctgtac aaggttaact agagctctag atccccgaat tccccgatc      1320 gttcaaacat ttggcaataa agtttcttaa gattgaatcc tgttgccggt cttgcgatga      1380
ttatcatata atttctgttg aattacgtta agcatgtaat aattaacatg taatgcatga      1440
cgttatttat gagatgggtt tttatgatta gagtcccgca attatacatt taatacgcga      1500
tagaaaacaa aatatagcgc gcaaactagg ataaattatc gcgcgcggtg tcatctatgt      1560
tactagatcg ggaattg                                                      1577
```

<210> SEQ ID NO 43
<211> LENGTH: 2725
<212> TYPE: DNA
<213> ORGANISM: Artificial
<220> FEATURE:
<223> OTHER INFORMATION: artificial sequence CmpC-GIG-nos expression
      cassette

<400> SEQUENCE: 43

```
tggcagacaa agtggcagac atactgtccc acaaatgaag atggaatctg taaaagaaaa       60
cgcgtgaaat aatgcgtctg acaaaggtta ggtcggctgc ctttaatcaa taccaaagtg      120
gtccctacca cgatggaaaa actgtgcagt cggtttggct ttttctgacg aacaaataag      180
attcgtggcc gacaggtggg ggtccaccat gtgaaggcat cttcagactc caataatgga      240
gcaatgacgt aagggcttac gaaataagta agggtagttt gggaaatgtc cactcacccg      300
tcagtctata aatacttagc ccctccctca ttgttaaggg agcaacgatc cgcgaagggc      360
gaattcctgc agcccggggg atcccctcga ggtcgaccat ggtccgtcct gtagaaaccc      420
caacccgtga atcaaaaaa ctcgacggcc tgtgggcatt cagtctggat cgcgaaaact      480
gtggaattga tcagcgttgg tgggaaagcg cgttacaaga aagccgggca attgctgtgc      540
caggcagttt taacgatcag ttcgccgatg cagatattcg taattatgcg ggcaacgtct      600
ggtatcagcg cgaagtcttt ataccgaaag gttgggcagg ccagcgtatc gtgctgcgtt      660
tcgatgcggt cactcattac ggcaaagtgt gggtcaataa tcaggaagtg atggagcatc      720
agggcggcta tgccatttt gaagccgatg tcacgccgta tgttattgcc gggaaaagtg      780
tacgtaagtt tctgcttcta cctttgatat atatataata attatcatta attagtagta      840
atataatatt tcaaatattt ttttcaaaat aaaagaatgt agtatatagc aattgctttt      900
ctgtagttta aagtgtgta tattttaatt tataacttt ctaatatatg accaaaattt      960
gttgatgtgc aggtatcacc gtttgtgtga caacgaact gaactggcag actatcccgc     1020
cgggaatggt gattaccgac gaaaacggca agaaaagca gtcttacttc catgatttct     1080
ttaactatgc cggaatccat cgcagcgtaa tgctctacac cacgccgaac acctgggtgg     1140
acgatatcac cgtggtgacg catgtcgcgc aagactgtaa ccacgcgtct gttgactggc     1200
aggtggtggc caatggtgat gtcagcgttg aactgcgtga tgcggatcaa caggtggttg     1260
caactggaca aggcactagc gggacttttc aagtggtgaa tccgcacctc tggcaaccgg     1320
gtgaaggtta tctctatgaa ctgtgcgtca cagcccaaag ccagacagag tgtgatatct     1380
acccgcttcg cgtcggcatc cggtcagtgg cagtgaaggg cgaacagttc ctgattaacc     1440
acaaaccgtt ctactttact ggctttggtc gtcatgaaga tgcggacttg cgtggcaaag     1500
gattcgataa cgtgctgatg gtgcacgacc acgcattaat ggactggatt ggggccaact     1560
```

-continued

```
cctaccgtac ctcgcattac ccttacgctg aagagatgct cgactgggca gatgaacatg     1620
gcatcgtggt gattgatgaa actgctgctg tcggctttaa cctctcttta ggcattggtt     1680
tcgaagcggg caacaagccg aaagaactgt acagcgaaga ggcagtcaac ggggaaactc     1740
agcaagcgca cttacaggcg attaaagagc tgatagcgcg tgacaaaaac cacccaagcg     1800
tggtgatgtg gagtattgcc aacgaaccgg atacccgtcc gcaaggtgca cgggaatatt     1860
tcgcgccact ggcggaagca acgcgtaaac tcgacccgac gcgtccgatc acctgcgtca     1920
atgtaatgtt ctgcgacgct cacaccgata ccatcagcga tctctttgat gtgctgtgcc     1980
tgaaccgtta ttacggatgg tatgtccaaa gcggcgattt ggaaacggca gagaaggtac     2040
tggaaaaaga acttctggcc tggcaggaga actgcatca gccgattatc atcaccgaat      2100
acggcgtgga tacgttagcc gggctgcact caatgtacac cgacatgtgg agtgaagagt     2160
atcagtgtgc atggctggat atgtatcacc gcgtctttga tcgcgtcagc gccgtcgtcg     2220
gtgaacaggt atggaatttc gccgattttg cgacctcgca aggcatattg cgcgttggcg     2280
gtaacaagaa agggatcttc actcgcgacc gcaaaccgaa gtcggcggct tttctgctgc     2340
aaaaacgctg gactggcatg aacttcggtg aaaaaccgca gcagggaggc aaacaatgaa     2400
tcaacaactc tcctggcgca ccatcgtcgg ctacagcctc gggaattaga tccccgaatt     2460
tccccgatcg ttcaaacatt tggcaataaa gtttcttaag attgaatcct gttgccggtc     2520
ttgcgatgat tatcatataa tttctgttga attacgttaa gcatgtaata attaacatgt     2580
aatgcatgac gttatttatg agatgggttt ttatgattag agtcccgcaa ttatacattt     2640
aatacgcgat agaaaacaaa atatagcgcg caaactagga taaattatcg cgcgcggtgt     2700
catctatgtt actagatcgg gaatt                                           2725
```

<210> SEQ ID NO 44
<211> LENGTH: 9172
<212> TYPE: DNA
<213> ORGANISM: Artificial
<220> FEATURE:
<223> OTHER INFORMATION: artificial sequence vector pNOV2117

<400> SEQUENCE: 44

```
aagcttggcg cgccggtacc agcttgcatg cctgcagtgc agcgtgaccc ggtcgtgccc       60
ctctctagag ataatgagca ttgcatgtct aagttataaa aaattaccac atatttttt      120 tgtcacactt gtttgaagtg cagtttatct atctttatac atatatttaa actttactct     180
acgaataata taatctatag tactacaata atatcagtgt tttagagaat catataaatg     240
aacagttaga catggtctaa aggacaattg agtattttga acacaggact ctacagtttt     300 atcttttag tgtgcatgtg ttctcctttt tttttgcaaa tagcttcacc tatataatac     360
ttcatccatt ttattagtac atccatttag ggtttagggt taatggtttt tatagactaa     420 ttttttagt acatctattt tattctattt tagcctctaa attaagaaaa ctaaaactct     480
attttagttt ttttatttaa taatttgat ataaaataga ataaaataaa gtgactaaaa     540
attaaacaaa taccctttaa gaaattaaaa aaactaagga acattttc ttgtttcgag       600 tagataatgc cagcctgtta aacgccgtcg acgagtctaa cggacaccaa ccagcgaacc      660
agcagcgtcg cgtcgggcca agcgaagcag acggcacggc atctctgtcg ctgcctctgg     720
acccctctcg agagttccgc tccaccgttg gacttgctcc gctgtcggca tccagaaatt     780
gcgtggcgga gcggcagacg tgagccggca cggcaggcgg cctcctcctc ctctcacggc     840
```

```
accggcagct acgggggatt cctttcccac cgctccttcg ctttcccttc ctcgcccgcc    900
gtaataaata gacacccccct ccacaccctc tttccccaac ctcgtgttgt tcggagcgca   960
cacacacaca accagatctc ccccaaatcc acccgtcggc acctccgctt caaggtacgc  1020
cgctcgtcct cccccccccc ccctctctac cttctctaga tcggcgttcc ggtccatggt  1080
tagggcccgg tagttctact tctgttcatg tttgtgttag atccgtgttt gtgttagatc  1140
cgtgctgcta gcgttcgtac acggatgcga cctgtacgtc agacacgttc tgattgctaa  1200
cttgccagtg tttctctttg gggaatcctg ggatggctct agccgttccg cagacgggat  1260
cgatttcatg attttttttg tttcgttgca tagggtttgg tttgcccttt tcctttattt  1320
caatatatgc cgtgcacttg tttgtcgggt catcttttca tgctttttt tgtcttggtt   1380
gtgatgatgt ggtctggttg ggcggtcgtt ctagatcgga gtagaattct gtttcaaact  1440
acctggtgga tttattaatt ttggatctgt atgtgtgtgc catacatatt catagttacg  1500
aattgaagat gatggatgga aatatcgatc taggataggt atacatgttg atgcgggttt  1560
tactgatgca tatacagaga tgcttttgt tcgcttggtt gtgatgatgt ggtgtggttg    1620
ggcggtcgtt cattcgttct agatcggagt agaatactgt ttcaaactac ctggtgtatt  1680
tattaatttt ggaactgtat gtgtgtgtca tacatcttca tagttacgag tttaagatgg  1740
atggaaatat cgatctagga taggtataca tgttgatgtg ggttttactg atgcatatac  1800
atgatggcat atgcagcatc tattcatatg ctctaacctt gagtacctat ctattataat  1860
aaacaagtat gttttataat tattttgatc ttgatatact tggatgatgg catatgcagc  1920
agctatatgt ggattttttt agccctgcct tcatacgcta tttatttgct tggtactgtt  1980
tcttttgtcg atgctcaccc tgttgtttgg tgttacttct gcagggatcc ccgatcatgc  2040
aaaaactcat taactcagtg caaaactatg cctggggcag caaaacggcg ttgactgaac  2100
tttatggtat ggaaaatccg tccagccagc cgatggccga gctgtggatg ggcgcacatc  2160
cgaaaagcag ttcacgagtg cagaatgccg ccggagatat cgtttcactg cgtgatgtga  2220
ttgagagtga taaatcgact ctgctcggag aggccgttgc caaacgcttt ggcgaactgc  2280
cttttcctgtt caaagtatta tgcgcagcac agccactctc cattcaggtt catccaaaca  2340
aacacaattc tgaaatcggt tttgccaaag aaaatgccgc aggtatcccg atggatgccg  2400
ccgagcgtaa ctataaagat cctaaccaca agccggagct ggttttttgcg ctgacgcctt  2460
tccttgcgat gaacgcgttt cgtgaatttt ccgagattgt ctccctactc cagccggtcg  2520
caggtgcaca tccggcgatt gctcactttt tacaacagc tgatgccgaa cgtttaagcg   2580
aactgttcgc cagcctgttg aatatgcagg tgaagaaaa atcccgcgcg ctggcgattt   2640
taaaatcggc cctcgatagc cagcagggtg aaccgtggca aacgattcgt ttaatttctg  2700
aattttaccc ggaagacagc ggtctgttct ccccgctatt gctgaatgtg gtgaaattga  2760
accctggcga agcgatgttc ctgttcgctg aaacaccgca cgcttacctg caaggcgtgg  2820
cgctggaagt gatggcaaac tccgataacg tgctgcgtgc gggtctgacg cctaaataca  2880
ttgatattcc ggaactggtt gccaatgtga aattcgaagc caaaccggct aaccagttgt  2940
tgacccagcc ggtgaaacaa ggtgcagaac tggacttccc gattccagtg atgattttg   3000
ccttctcgct gcatgacctt agtgataaag aaaccaccat tagccagcag agtgccgcca  3060
ttttgttctg cgtcgaaggc gatgcaacgt tgtggaaagg ttctcagcag ttacagctta  3120
aaccgggtga atcagcgttt attgccgcca acgaatcacc ggtgactgtc aaaggccacg  3180
gccgtttagc gcgtgtttac aacaagctgt aagagcttac tgaaaaaatt aacatctctt  3240
```

-continued

```
gctaagctgg gagctcgatc cgtcgacctg cagatcgttc aaacatttgg caataaagtt    3300
tcttaagatt gaatcctgtt gccggtcttg cgatgattat catataattt ctgttgaatt    3360
acgttaagca tgtaataatt aacatgtaat gcatgacgtt atttatgaga tgggttttta    3420
tgattagagt cccgcaatta tacatttaat acgcgataga aaacaaaata tagcgcgcaa    3480
actaggataa attatcgcgc gcggtgtcat ctatgttact agatctgcta gccctgcagg    3540
aaatttaccg gtgcccgggc ggccagcatg gccgtatccg caatgtgtta ttaagttgtc    3600
taagcgtcaa tttgtttaca ccacaatata tcctgccacc agccagccaa cagctccccg    3660
accggcagct cggcacaaaa tcaccactcg atacaggcag cccatcagaa ttaattctca    3720
tgtttgacag cttatcatcg actgcacggt gcaccaatgc ttctggcgtc aggcagccat    3780
cggaagctgt ggtatggctg tgcaggtcgt aaatcactgc ataattcgtg tcgctcaagg    3840
cgcactcccg ttctggataa tgttttttgc gccgacatca taacggttct ggcaaatatt    3900
ctgaaatgag ctgttgacaa ttaatcatcc ggctcgtata atgtgtggaa ttgtgagcgg    3960
ataacaattt cacacaggaa acagaccatg agggaagcgt tgatcgccga agtatcgact    4020
caactatcag aggtagttgg cgtcatcgag cgccatctcg aaccgacgtt gctggccgta    4080
catttgtacg gctccgcagt ggatggcggc ctgaagccac acagtgatat tgatttgctg    4140
gttacggtga ccgtaaggct tgatgaaaca acgcggcgag ctttgatcaa cgaccttttg    4200
gaaacttcgg cttcccctgg agagagcgag attctccgcg ctgtagaagt caccattgtt    4260
gtgcacgacg acatcattcc gtggcgttat ccagctaagc gcgaactgca atttggagaa    4320
tggcagcgca atgacattct tgcaggtatc ttcgagccag ccacgatcga cattgatctg    4380
gctatcttgc tgacaaaagc aagagaacat agcgttgcct tggtaggtcc agcggcggag    4440
gaactctttg atccggttcc tgaacaggat ctatttgagg cgctaaatga aaccttaacg    4500
ctatggaact cgccgcccga ctgggctggc gatgagcgaa atgtagtgct tacgttgtcc    4560
cgcatttggt acagcgcagt aaccggcaaa atcgcgccga aggatgtcgc tgccgactgg    4620
gcaatggagc gcctgccggc ccagtatcag cccgtcatac ttgaagctag caggcttat    4680 cttggacaag aagatcgctt ggcctcgcgc gcagatcagt tggaagaatt tgttcactac    4740
gtgaaaggcg agatcaccaa gtagtcggc aaataaagct ctagtggatc tccgtacccc    4800
cgggggatct ggctcgcggc ggacgcacga cgccggggcg agaccatagg cgatctccta    4860
aatcaatagt agctgtaacc tcgaagcgtt tcacttgtaa caacgattga gaattttgt    4920 cataaaattg aaatacttgg ttcgcatttt tgtcatccgc ggtcagccgc aattctgacg    4980
aactgcccat ttagctggag atgattgtac atccttcacg tgaaaatttc tcaagcgctg    5040
tgaacaaggg ttcagatttt agattgaaag gtgagccgtt gaaacacgtt cttcttgtcg    5100
atgacgacgt cgctatgcgg catcttatta ttgaatacct tacgatccac gccttcaaag    5160
tgaccgcggt agccgacagc acccagttca caagagtact ctcttccgcg acggtcgatg    5220
tcgtggttgt tgatctaaat ttaggtcgtg aagatgggct cgagatcgtt cgtaatctgg    5280
cggcaaagtc tgatattcca atcataatta tcagtggcga ccgccttgag gagacggata    5340
aagttgttgc actcgagcta ggagcaagtg attttatcgc taagccgttc agtatcagag    5400
agtttctagc acgcattcgg gttgccttgc gcgtgcgccc aacgttgtc cgctccaaag    5460 accgacggtc tttttgtttt actgactgga cacttaatct caggcaacgt cgcttgatgt    5520
ccgaagctgg cggtgaggtg aaacttacgg caggtgagtt caatcttctc ctcgcgtttt    5580
```

-continued

```
tagagaaacc ccgcgacgtt ctatcgcgcg agcaacttct cattgccagt cgagtacgcg    5640
acgaggaggt ttatgacagg agtatagatg ttctcatttt gaggctgcgc cgcaaacttg    5700
aggcagatcc gtcaagccct caactgataa aaacagcaag aggtgccggt tatttctttg    5760
acgcggacgt gcaggtttcg cacgggggga cgatggcagc ctgagccaat tcccagatcc    5820
ccgaggaatc ggcgtgagcg gtcgcaaacc atccggcccg gtacaaatcg gcgcggcgct    5880
gggtgatgac ctggtggaga agttgaaggc cgcgcaggcc gcccagcggc aacgcatcga    5940
ggcagaagca cgccccggtg aatcgtggca agcggccgct gatcgaatcc gcaaagaatc    6000
ccggcaaccg ccggcagccg gtgcgccgtc gattaggaag ccgcccaagg gcgacgagca    6060
accagatttt ttcgttccga tgctctatga cgtgggcacc cgcgatagtc gcagcatcat    6120
ggacgtggcc gttttccgtc tgtcgaagcg tgaccgacga gctggcgagg tgatccgcta    6180
cgagcttcca gacgggcacg tagaggtttc gcagggccg gccggcatgg ccagtgtgtg    6240
ggattacgac ctggtactga tggcggtttc ccatctaacc gaatccatga accgataccg    6300
ggaagggaag ggagacaagc ccggccgcgt gttccgtcca cacgttgcgg acgtactcaa    6360
gttctgccgg cgagccgatg gcggaaagca gaaagacgac ctggtagaaa cctgcattcg    6420
gttaaacacc acgcacgttg ccatgcagcg tacgaagaag gccaagaacg gccgcctggt    6480
gacggtatcc gagggtgaag ccttgattag ccgctacaag atcgtaaaga gcgaaaccgg    6540
gcggccggag tacatcgaga tcgagctagc tgattggatg taccgcgaga tcacagaagg    6600
caagaacccg gacgtgctga cggttcaccc cgattacttt ttgatcgatc ccggcatcgg    6660 ccgtttttctc taccgcctgg cacgccgcgc cgcaggcaag gcagaagcca gatggttgtt    6720
caagacgatc tacgaacgca gtggcagcgc cggagagttc aagaagttct gtttcaccgt    6780
gcgcaagctg atcgggtcaa atgacctgcc ggagtacgat ttgaaggagg aggcggggca    6840
ggctggcccg atcctagtca tgcgctaccg caacctgatc gagggcgaag catccgccgg    6900
ttcctaatgt acggagcaga tgctagggca aattgcccta gcaggggaaa aaggtcgaaa    6960
aggtctcttt cctgtggata gcacgtacat tgggaaccca aagccgtaca ttgggaaccg    7020
gaacccgtac attgggaacc caaagccgta cattgggaac cggtcacaca tgtaagtgac    7080
tgatataaaa gagaaaaaag gcgatttttc cgcctaaaac tctttaaaac ttattaaaac    7140
tcttaaaacc cgcctggcct gtgcataact gtctggccag cgcacagccg aagagctgca    7200
aaaagcgcct acccttcggt cgctgcgctc cctacgcccc gccgcttcgc gtcggcctat    7260
cgcggccgct ggccgctcaa aaatggctgg cctacggcca ggcaatctac cagggcgcgg    7320
acaagccgcg ccgtcgccac tcgaccgccg gcgctgaggt ctgcctcgtg aagaaggtgt    7380
tgctgactca taccaggcct gaatcgcccc atcatccagc cagaaagtga gggagccacg    7440
gttgatgaga gctttgttgt aggtggacca gttggtgatt ttgaactttt gctttgccac    7500
ggaacggtct gcgttgtcgg gaagatgcgt gatctgatcc ttcaactcag caaaagttcg    7560
atttattcaa caaagccgcc gtcccgtcaa gtcagcgtaa tgctctgcca gtgttacaac    7620
caattaacca attctgatta gaaaaactca tcgagcatca aatgaaactg caatttattc    7680
atatcaggat tatcaatacc atattttga aaaagccgtt tctgtaatga aggagaaaac    7740
tcaccgaggc agttccatag gatggcaaga tcctggtatc ggtctgcgat tccgactcgt    7800
ccaacatcaa tacaacctat taatttcccc tcgtcaaaaa taaggttatc aagtgagaaa    7860
tcaccatgag tgacgactga atccggtgag aatggcaaaa gctctgcatt aatgaatcgg    7920
ccaacgcgcg gggagaggcg gtttgcgtat tgggcgctct tccgcttcct cgctcactga    7980
```

-continued

| | |
|---|---|
| ctcgctgcgc tcggtcgttc ggctgcggcg agcggtatca gctcactcaa aggcggtaat | 8040 |
| acggttatcc acagaatcag gggataacgc aggaaagaac atgtgagcaa aaggccagca | 8100 |
| aaaggccagg aaccgtaaaa aggccgcgtt gctggcgttt ttccataggc tccgcccccc | 8160 |
| tgacgagcat cacaaaaatc gacgctcaag tcagaggtgg cgaaacccga caggactata | 8220 |
| aagataccag gcgtttcccc ctggaagctc cctcgtgcgc tctcctgttc cgaccctgcc | 8280 |
| gcttaccgga tacctgtccg cctttctccc ttcgggaagc gtggcgcttt ctcatagctc | 8340 |
| acgctgtagg tatctcagtt cggtgtaggt cgttcgctcc aagctgggct gtgtgcacga | 8400 |
| accccccgtt cagcccgacc gctgcgcctt atccggtaac tatcgtcttg agtccaaccc | 8460 |
| ggtaagacac gacttatcgc cactggcagc agccactggt aacaggatta gcagagcgag | 8520 |
| gtatgtaggc ggtgctacag agttcttgaa gtggtggcct aactacggct acactagaag | 8580 |
| aacagtattt ggtatctgcg ctctgctgaa gccagttacc ttcggaaaaa gagttggtag | 8640 |
| ctcttgatcc ggcaaacaaa ccaccgctgg tagcggtggt ttttttgttt gcaagcagca | 8700 |
| gattacgcgc agaaaaaaag gatctcaaga agatcctttg atcttttcta cggggtctga | 8760 |
| cgctcagtgg aacgaaaact cacgttaagg gattttggtc atgagattat caaaaaggat | 8820 |
| cttcacctag atcctttga tccggaatta ttcctgtgg ttggcatgca catacaaatg | 8880 |
| gacgaacgga taaccttttt cacgcccttt taaatatccg attattctaa taaacgctct | 8940 |
| tttctcttag gtttacccgc caatatatcc tgtcaaacac tgatagttta aactgaaggc | 9000 |
| gggaaacgac aatctgatca tgagcggaga attaaggag tcacgttatg accccgccg | 9060 |
| atgacgcggg acaagccgtt ttacgtttgg aactgacaga accgcaacgc tgcaggaatt | 9120 |
| ggccgcagcg gccatttaaa tcaattgggc gcgccgaatt cgagctcggt ac | 9172 |

<210> SEQ ID NO 45
<211> LENGTH: 8849
<212> TYPE: DNA
<213> ORGANISM: Artificial
<220> FEATURE:
<223> OTHER INFORMATION: artificial sequence vector pNOV4200

<400> SEQUENCE: 45

| | |
|---|---|
| ggtaccccg gggatcctc tagagtcgac catggtgatc actgcaggca tgcaagcttc | 60 |
| gtacgttaat taattcgaat ccggagcggc cgcacgcgtg ggcccgttta acctcgaga | 120 |
| gatctgctag ccctgcagga aatttaccgg tgcccgtacc ggatttggag ccaagtctca | 180 |
| taaacgccat tgtggaagaa agtcttgagt tggtggtaat gtaacagagt agtaagaaca | 240 |
| gagaagagag agagtgtgag atacatgaat tgtcgggcaa caaaaatcct gaacatctta | 300 |
| ttttagcaaa gagaaagagt tccgagtctg tagcagaaga gtgaggagaa atttaagctc | 360 |
| ttggacttgt gaattgttcc gcctcttgaa tacttcttca atcctcatat attcttcttc | 420 |
| tatgttacct gaaaaccggc atttaatctc gcgggttat tccggttcaa catttttttt | 480 |
| gttttgagtt attatctggg cttaataacg caggcctgaa ataaattcaa ggcccaactg | 540 |
| tttttttttt taagaagttg ctgttaaaaa aaaaaaagg gaattaacaa caacaacaaa | 600 |
| aaagataaa gaaataata acaattactt taattgtaga ctaaaaaaac atagatttta | 660 |
| tcatgaaaaa aagagaaaag aaataaaaac ttggatcaaa aaaaaacata cagatcttct | 720 |
| aattattaac ttttcttaaa aattaggtcc ttttttcccaa caattaggtt tagagttttg | 780 |
| gaattaaacc aaaaagattg ttctaaaaaa tactcaaatt tggtagataa gtttccttat | 840 |

-continued

```
tttaattagt caatggtaga tacttttttt tcttttcttt attagagtag attagaatct    900
tttatgccaa gtattgataa attaaatcaa gaagataaac tatcataatc aacatgaaat    960
taaaagaaaa atctcatata tagtattagt attctctata tatattatga ttgcttattc   1020
ttaatgggtt gggttaacca agacatagtc ttaatggaaa gaatctttt tgaactttt    1080
ccttattgat taaattcttc tatagaaaag aaagaaatta tttgaggaaa agtatataca   1140
aaagaaaaa tagaaaaatg tcagtgaagc agatgtaatg gatgacctaa tccaaccacc    1200
accataggat gtttctactt gagtcggtct tttaaaaacg cacggtggaa aatatgacac   1260
gtatcatatg attccttcct ttagtttcgt gataataatc ctcaactgat atcttccttt   1320
ttttgttttg gctaaagata ttttattctc attaatagaa aagacggttt tgggcttttg   1380
gtttgcgata taaagaagac cttcgtgtgg aagataataa ttcatccttt cgtctttttc   1440
tgactcttca atctctccca aagcctaaag cgatctctgc aaatctctcg cgactctctc   1500
tttcaaggta tattttctga ttcttttgt ttttgattcg tatctgatct ccaattttg    1560
ttatgtggat tattgaatct tttgtataaa ttgcttttga caatattgtt cgtttcgtca   1620
atccagcttc taaattttgt cctgattact aagatatcga ttcgtagtgt ttacatctgt   1680
gtaatttctt gcttgattgt gaaattagga ttttcaagga cgatctattc aattttgtg   1740
ttttctttgt tcgattctct ctgttttagg tttcttatgt ttagatccgt ttctctttgg   1800
tgttgttttg atttctctta cggcttttga tttggtatat gttcgctgat tggtttctac   1860
ttgttctatt gtttatttc aggtggatct cgactctagg ggggcaataa gatatgaaaa   1920
agcctgaact caccgcgacg tctgtcgaga agtttctgat cgaaaagttc gacagcgtct   1980
ccgacctgat gcagctctcg gagggcgaag aatctcgtgc tttcagcttc gatgtaggag   2040
ggcgtggata tgtcctgcgg gtaaatagct gcgccgatgg tttctacaaa gatcgttatg   2100
tttatcggca ctttgcatcg gccgcgctcc cgattccgga agtgcttgac attgggcat    2160
tcagcgagag cctgacctat tgcatctccc gccgtgcaca gggtgtcacg ttgcaagacc   2220
tgcctgaaac cgaactgccc gctgttctgc agccggtcgc ggaggccatg gatgcgatcg   2280
ctgcggccga tcttagccag acgagcgggt tcggcccatt cggaccgcaa ggaatcggtc   2340
aatacactac atggcgtgat ttcatatgcg cgattgctga tccccatgtg tatcactggc   2400
aaactgtgat ggacgacacc gtcagtgcgt ccgtcgcgca ggctctcgat gagctgatgc   2460
tttgggccga ggactgcccc gaagtccggc acctcgtgca cgcggatttc ggctccaaca   2520
atgtcctgac ggacaatggc cgcataacag cggtcattga ctggagcgag gcgatgttcg   2580
gggattccca atacgaggtc gccaacatct tcttctggag gccgtggttg gcttgtatgg   2640
agcagcagac gcgctacttc gagcggaggc atccggagct tgcaggatcg ccgcggctcc   2700
gggcgtatat gctccgcatt ggtcttgacc aactctatca gagcttggtt gacggcaatt   2760
tcgatgatgc agcttgggcg cagggtcgat gcgacgcaat cgtccgatcc ggagccggga   2820
ctgtcgggcg tacacaaatc gcccgcagaa gcgcggccgt ctggaccgat ggctgtgtag   2880
aagtactcgc cgatagtgga aaccgacgcc ccagcactcg tccgagggca aggaataga    2940
gtagatgccg accgggatcc ccgaatttcc ccgatcgttc aaacatttgg caataaagtt   3000
tcttaagatt gaatcctgtt gccggtcttg cgatgattat catataattt ctgttgaatt   3060
acgttaagca tgtaataatt aacatgtaat gcatgacgtt atttatgaga tgggttttta   3120
tgattagagt cccgcaatta tacatttaat acgcgataga aaacaaaata tagcgcgcaa   3180
actaggataa attatcgcgc gcggtgtcat ctatgttact agatcgggaa ttgggtacgg   3240
```

```
gcggccagca tggccgtatc cgcaatgtgt tattaagttg tctaagcgtc aatttgttta    3300
caccacaata tatcctgcca ccagccagcc aacagctccc cgaccggcag ctcggcacaa    3360
aatcaccact cgatacaggc agcccatcag aattaattct catgtttgac agcttatcat    3420
cgactgcacg gtgcaccaat gcttctggcg tcaggcagcc atcggaagct gtggtatggc    3480
tgtgcaggtc gtaaatcact gcataattcg tgtcgctcaa ggcgcactcc cgttctggat    3540
aatgtttttt gcgccgacat cataacggtt ctggcaaata ttctgaaatg agctgttgac    3600
aattaatcat ccggctcgta taatgtgtgg aattgtgagc ggataacaat tcacacagg     3660
aaacagacca tgagggaagc gttgatcgcc gaagtatcga ctcaactatc agaggtagtt    3720
ggcgtcatcg agcgccatct cgaaccgacg ttgctggccg tacatttgta cggctccgca    3780
gtggatggcg gcctgaagcc acacagtgat attgatttgc tggttacggt gaccgtaagg    3840
cttgatgaaa caacgcggcg agctttgatc aacgaccttt tggaaacttc ggcttcccct    3900
ggagagagcg agattctccg cgctgtagaa gtcaccattg ttgtgcacga cgacatcatt    3960
ccgtggcgtt atccagctaa gcgcgaactg caatttggag aatggcagcg caatgacatt    4020
cttgcaggta tcttcgagcc agccacgatc gacattgatc tggctatctt gctgacaaaa    4080
gcaagagaac atagcgttgc cttggtaggt ccagcggcgg aggaactctt tgatccggtt    4140
cctgaacagg atctatttga ggcgctaaat gaaaaccttaa cgctatggaa ctcgccgccc    4200
gactgggctg gcgatgagcg aaatgtagtg cttacgttgt cccgcatttg gtacagcgca    4260
gtaaccggca aaatcgcgcc gaaggatgtc gctgccgact gggcaatgga gcgcctgccg    4320
gcccagtatc agcccgtcat acttgaagct aggcaggctt atcttggaca agaagatcgc    4380
ttggcctcgc gcgcagatca gttggaagaa tttgttcact acgtgaaagg cgagatcacc    4440
aaagtagtcg gcaaataaag ctctagtgga tctccgtacc cccggggat ctggctcgcg     4500
gcggacgcac gacgccgggg cgagaccata ggcgatctcc taaatcaata gtagctgtaa    4560
cctcgaagcg tttcacttgt aacaacgatt gagaattttt gtcataaaat tgaaatactt    4620
ggttcgcatt tttgtcatcc gcggtcagcc gcaattctga cgaactgccc atttagctgg    4680
agatgattgt acatccttca cgtgaaaatt tctcaagcgc tgtgaacaag ggttcagatt    4740
ttagattgaa aggtgagccg ttgaaacacg ttcttcttgt cgatgacgac gtcgctatgc    4800
ggcatcttat tattgaatac cttacgatcc acgccttcaa agtgaccgcg gtagccgaca    4860
gcacccagtt cacaagagta ctctcttccg cgacggtcga tgtcgtggtt gttgatctag    4920
atttaggtcg tgaagatggg ctcgagatcg ttcgtaatct ggcggcaaag tctgatattc    4980
caatcataat tatcagtggc gaccgccttg aggagacgga taagttgtt gcactcgagc     5040
taggagcaag tgattttatc gctaagccgt tcagtatcag agagtttcta gcacgcattc    5100
gggttgcctt gcgcgtgcgc cccaacgttg tccgctccaa agaccgacgg tcttttttgtt   5160
ttactgactg gacacttaat ctcaggcaac gtcgcttgat gtccgaagct ggcggtgagg    5220
tgaaacttac ggcaggtgag ttcaatcttc tcctcgcgtt tttagagaaa ccccgcgacg    5280
ttctatcgcg cgagcaactt ctcattgcca gtcgagtacg cgacgaggag gtttatgaca    5340
ggagtataga tgttctcatt ttgaggctgc gccgcaaact tgaggcagat ccgtcaagcc    5400
ctcaactgat aaaaacagca agaggtgccg gttatttctt tgacgcggac gtgcaggttt    5460
cgcacggggg gacgatggca gcctgagcca attcccagat ccccgaggaa tcggcgtgag    5520
cggtcgcaaa ccatccggcc cggtacaaat cggcgcggcg ctgggtgatg acctggtgga    5580
```

```
gaagttgaag gccgcgcagg ccgcccagcg gcaacgcatc gaggcagaag cacgccccgg   5640
tgaatcgtgg caagcggccg ctgatcgaat ccgcaaagaa tcccggcaac cgccggcagc   5700
cggtgcgccg tcgattagga agccgcccaa gggcgacgag caaccagatt ttttcgttcc   5760
gatgctctat gacgtgggca cccgcgatag tcgcagcatc atggacgtgg ccgttttccg   5820
tctgtcgaag cgtgaccgac gagctggcga ggtgatccgc tacgagcttc cagacgggca   5880
cgtagaggtt tccgcagggc cggccggcat ggccagtgtg tgggattacg acctggtact   5940
gatggcggtt tcccatctaa ccgaatccat gaaccgatac cgggaaggga agggagacaa   6000
gcccggccgc gtgttccgtc cacacgttgc ggacgtactc aagttctgcc ggcgagccga   6060
tggcggaaag cagaaagacg acctggtaga aacctgcatt cggttaaaca ccacgcacgt   6120
tgccatgcag cgtacgaaga aggccaagaa cggccgcctg gtgacggtat ccgagggtga   6180
agccttgatt agccgctaca agatcgtaaa gagcgaaacc gggcggccgg agtacatcga   6240
gatcgagcta gctgattgga tgtaccgcga gatcacagaa gcaagaaacc cggacgtgct   6300
gacggttcac cccgattact ttttgatcga tcccggcatc ggccgttttc tctaccgcct   6360
ggcacgccgc gccgcaggca aggcagaagc cagatggttg ttcaagacga tctacgaacg   6420
cagtggcagc gccggagagt tcaagaagtt ctgtttcacc gtgcgcaagc tgatcgggtc   6480
aaatgacctg ccggagtacg atttgaagga ggaggcgggg caggctggcc cgatcctagt   6540
catgcgctac cgcaacctga tcgagggcga agcatccgcc ggttcctaat gtacggagca   6600
gatgctaggg caaattgccc tagcagggga aaaaggtcga aaaggtctct ttcctgtgga   6660
tagcacgtac attgggaacc caaagccgta cattgggaac cggaacccgt acattgggaa   6720
cccaaagccg tacattggga accggtcaca catgtaagtg actgatataa aagagaaaaa   6780
aggcgatttt tccgcctaaa actctttaaa acttattaaa actcttaaaa cccgcctggc   6840
ctgtgcataa ctgtctggcc agcgcacagc cgaagagctg caaaaagcgc ctacccttcg   6900
gtcgctgcgc tccctacgcc ccgccgcttc gcgtcggcct atcgcggccg ctggccgctc   6960
aaaaatggct ggcctacggc caggcaatct accaggcgc ggacaagccg cgccgtcgcc    7020
actcgaccgc cggcgctgag gtctgcctcg tgaagaaggt gttgctgact cataccaggc   7080
ctgaatcgcc ccatcatcca gccagaaagt gagggagcca cggttgatga gagctttgtt   7140
gtaggtggac cagttggtga ttttgaactt ttgctttgcc acggaacggt ctgcgttgtc   7200
gggaagatgc gtgatctgat ccttcaactc agcaaaagtt cgatttattc aacaaagccg   7260
ccgtcccgtc aagtcagcgt aatgctctgc cagtgttaca accaattaac caattctgat   7320
tagaaaaact catcgagcat caaatgaaac tgcaatttat tcatatcagg attatcaata   7380 ccatatttt gaaaaagccg tttctgtaat gaaggagaaa actcaccgag gcagttccat    7440
aggatggcaa gatcctggta tcggtctgcg attccgactc gtccaacatc aatacaacct   7500
attaatttcc cctcgtcaaa ataaggttat caagtgaga atcaccatg agtgacgact     7560 gaatccggtg agaatggcaa aagctctgca ttaatgaatc ggccaacgcg cggggagagg   7620
cggtttgcgt attgggcgct cttccgcttc ctcgctcact gactcgctgc gctcggtcgt   7680
tcggctgcgg cgagcggtat cagctcactc aaaggcggta atacggttat ccacagaatc   7740
aggggataac gcaggaaaga acatgtgagc aaaaggccag caaaaggcca ggaaccgtaa   7800
aaaggccgcg ttgctggcgt ttttccatag gctccgcccc cctgacgagc atcacaaaaa   7860
tcgacgctca agtcagaggt ggcgaaaccc gacaggacta taaagatacc aggcgtttcc   7920
ccctggaagc tccctcgtgc gctctcctgt tccgaccctg ccgcttaccg gatacctgtc   7980
```

-continued

```
cgcctttctc ccttcgggaa gcgtggcgct ttctcatagc tcacgctgta ggtatctcag    8040
ttcggtgtag gtcgttcgct ccaagctggg ctgtgtgcac gaaccccccg ttcagcccga    8100
ccgctgcgcc ttatccggta actatcgtct tgagtccaac ccggtaagac acgacttatc    8160
gccactggca gcagccactg gtaacaggat tagcagagcg aggtatgtag gcggtgctac    8220
agagttcttg aagtggtggc ctaactacgg ctacactaga agaacagtat ttggtatctg    8280
cgctctgctg aagccagtta ccttcggaaa aagagttggt agctcttgat ccggcaaaca    8340
aaccaccgct ggtagcggtg gtttttttgt ttgcaagcag cagattacgc gcagaaaaaa    8400
aggatctcaa gaagatcctt tgatcttttc tacggggtct gacgctcagt ggaacgaaaa    8460
ctcacgttaa gggattttgg tcatgagatt atcaaaaagg atcttcacct agatcctttt    8520
gatccggaat taattcctgt ggttggcatg cacatacaaa tggacgaacg gataaacctt    8580
ttcacgccct tttaaatatc cgattattct aataaacgct cttttctctt aggtttaccc    8640
gccaatatat cctgtcaaac actgatagtt taaactgaag gcgggaaacg acaatctgat    8700
catgagcgga gaattaaggg agtcacgtta tgacccccgc cgatgacgcg ggacaagccg    8760
ttttacgttt ggaactgaca gaaccgcaac gctgcaggaa ttggccgcag cggccattta    8820
aatcaattgg gcgcgccgaa ttcgagctc                                      8849
```

<210> SEQ ID NO 46
<211> LENGTH: 2949
<212> TYPE: DNA
<213> ORGANISM: Artificial
<220> FEATURE:
<223> OTHER INFORMATION: artificial sequence ZmUbi-GFP-35S term
      expression cassette

<400> SEQUENCE: 46

```
gcatgcctgc agtgcagcgt gacccggtcg tgccctctc tagagataat gagcattgca      60
tgtctaagtt ataaaaaatt accacatatt ttttttgtca cacttgtttg aagtgcagtt    120
tatctatctt tatacatata tttaaacttt actctacgaa taatataatc tatagtacta    180
caataatatc agtgttttag agaatcatat aaatgaacag ttagacatgg tctaaaggac    240
aattgagtat tttgacaaca ggactctaca gtttatctt tttagtgtgc atgtgttctc     300 ctttttttt gcaaatagct tcacctatat aatacttcat ccatttatt agtacatcca     360 tttagggttt agggttaatg gttttttatag actaatttt ttagtacatc tattttattc    420
tattttagcc tctaaattaa gaaaactaaa actctatttt agttttttta tttaataatt    480
tagatataaa atagaataaa ataaagtgac taaaaattaa acaaataccc tttaagaaat    540
taaaaaaact aaggaaacat ttttcttgtt tcgagtagat aatgccagcc tgttaaacgc    600
cgtcgacgag tctaacggac accaaccagc gaaccagcag cgtcgcgtcg ggccaagcga    660
agcagacggc acggcatctc tgtcgctgcc tctggacccc tctcgagagt tccgctccac    720
cgttggactt gctccgctgt cggcatccag aaattgcgtg gcggagcggc agacgtgagc    780
cggcacggca ggcggcctcc tcctcctctc acggcacggc agctacgggg gattcctttc    840
ccaccgctcc ttcgctttcc cttcctcgcc cgccgtaata aatagacacc cctccacac    900 cctctttccc caacctcgtg ttgttcggag cgcacacaca caaccagac tctccccaa     960 atccacccgt cggcacctcc gcttcaaggt acgccgctcg tcctcccccc ccccccctct   1020
ctaccttctc tagatcggcg ttccggtcca tggttagggc ccggtagttc tacttctgtt   1080
catgtttgtg ttagatccgt gtttgtgtta gatccgtgct gctagcgttc gtacacggat   1140
```

```
gcgacctgta cgtcagacac gttctgattg ctaacttgcc agtgtttctc tttggggaat    1200
cctgggatgg ctctagccgt tccgcagacg ggatcgattt catgattttt tttgtttcgt    1260
tgcatagggt ttggtttgcc cttttccttt atttcaatat atgccgtgca cttgtttgtc    1320
gggtcatctt ttcatgcttt tttttgtctt ggttgtgatg atgtggtctg gttgggcggt    1380
cgttctagat cggagtagaa ttctgtttca aactacctgg tggatttatt aattttggat    1440
ctgtatgtgt gtgccataca tattcatagt tacgaattga agatgatgga tggaaatatc    1500
gatctaggat aggtatacat gttgatgcgg gttttactga tgcatataca gagatgcttt    1560
ttgttcgctt ggttgtgatg atgtggtgtg gttgggcggt cgttcattcg ttctagatcg    1620
gagtagaata ctgtttcaaa ctacctggtg tatttattaa ttttggaact gtatgtgtgt    1680
gtcatacatc ttcatagtta cgagtttaag atggatggaa atatcgatct aggataggta    1740
tacatgttga tgtgggtttt actgatgcat atacatgatg gcatatgcag catctattca    1800
tatgctctaa ccttgagtac ctatctatta taataaacaa gtatgtttta taattatttt    1860
gatcttgata tacttggatg atggcatatg cagcagctat atgtggattt ttttagccct    1920
gccttcatac gctatttatt tgcttggtac tgtttctttt gtcgatgctc accctgttgt    1980
ttggtgttac ttctgcaggt cgactctaga ggatccacca tgctgcagat gagcaagggc    2040
gaggagctgt tcaccggcgt ggtgccaatc ctggtggagc tggacggcga cgtgaacggc    2100
cacaagttca gcgtgagcgg cgagggcgag ggcgacgcga cctacggcaa gctgaccctg    2160
aagttcatct gtaccaccgg caagctcccg gtcccgtggc cgaccctggt gaccaccttc    2220
acctacggcg tgcagtgttt cagccgctac ccggaccaca tgaagcgcca cgacttcttc    2280
aagagcgcca tgccggaggg ctacgtgcag gagcgcacca tcagcttcaa ggacgacggc    2340
aactacaaga cccgcgccga ggtgaagttc gagggcgaca cactagtgaa ccgcatcgag    2400
ctgaagggca tcgacttcaa ggaggacggc aacatcctgg ccacaagct ggagtacaac    2460 tacaacagcc acaacgtgta catcaccgcg acaagcaga agaacggcat caaggcgaac    2520
ttcaagatcc gccacaacat cgaggacggc agcgtgcagc tggccgacca ctaccagcag    2580
aacaccccga tcggcgacgg tcctgtgctg ctgccggaca accactacct gagcacccag    2640
agcgccctga gcaaggaccc gaacgagaag cgcgaccaca tggtgctgct ggagttcgtg    2700
accgccgccg gcatcaccca cggcatggac gagctgtaca aggttaacta gagctcaaga    2760
tctgttctgc acaaagtgga gtagtcagtc atcgatcagg aaccagacac cagacttta    2820 ttcatacagt gaagtgaagt gaagtgcagt gcagtgagtt gctggttttt gtacaactta    2880 gtatgtatt gtatttgtaa aatacttcta tcaataaaat ttctaattcc taaaaccaaa    2940
atccagtgg                                                             2949

<210> SEQ ID NO 47
<211> LENGTH: 4341
<212> TYPE: DNA
<213> ORGANISM: Artificial
<220> FEATURE:
<223> OTHER INFORMATION: artificial sequence ZmUBi-GIG-nos expression
      cassette

<400> SEQUENCE: 47
cctgcagtgc agcgtgaccc ggtcgtgccc ctctctagag ataatgagca ttgcatgtct      60
aagttataaa aaattaccac atattttttt tgtcacactt gtttgaagtg cagtttatct     120
atctttatac atatatttaa actttactct acgaataata taatctatag tactacaata     180
```

-continued

```
atatcagtgt tttagagaat catataaatg aacagttaga catggtctaa aggacaattg    240
agtattttga caacaggact ctacagtttt atctttttag tgtgcatgtg ttctccttt     300 tttttgcaaa tagcttcacc tatataatac ttcatccatt ttattagtac atccatttag    360
ggtttagggt taatggtttt tatagactaa ttttttagt acatctattt tattctattt     420
tagcctctaa attaagaaaa ctaaaactct attttagttt ttttatttaa taatttagat    480
ataaaataga ataaaataaa gtgactaaaa attaaacaaa tacccttaa gaaattaaaa     540 aaactaagga aacattttc ttgtttcgag tagataatgc cagcctgtta aacgccgtcg     600
acgagtctaa cggacaccaa ccagcgaacc agcagcgtcg cgtcgggcca agcgaagcag    660
acggcacggc atctctgtcg ctgcctctgg accccctctcg agagttccgc tccaccgttg    720
gacttgctcc gctgtcggca tccagaaatt gcgtggcgga gcggcagacg tgagccggca    780
cggcaggcgg cctcctcctc ctctcacggc accggcagct acggggatt cctttcccac     840 cgctccttcg ctttcccttc ctcgcccgcc gtaataaata gaccacccct ccacaccctc    900
tttccccaac ctcgtgttgt tcggagcgca cacacacaca accagatctc ccccaaatcc    960
acccgtcggc acctccgctt caaggtacgc cgctcgtcct ccccccccc cctctctac     1020 cttctctaga tcggcgttcc ggtccatggt tagggcccgg tagttctact tctgttcatg   1080
tttgtgttag atccgtgttt gtgttagatc cgtgctgcta gcgttcgtac acggatgcga   1140
cctgtacgtc agacacgttc tgattgctaa cttgccagtg tttctctttg gggaatcctg   1200
ggatggctct agccgttccg cagacgggat cgatttcatg attttttttg tttcgttgca   1260
taggggttgg tttgcccttt tccttattt caatatatgc cgtgcacttg tttgtcgggt    1320
catcttttca tgctttttt tgtcttggtt gtgatgatgt ggtctggttg ggcggtcgtt    1380
ctagatcgga gtagaattct gtttcaaact acctggtgga tttattaatt ttggatctgt   1440
atgtgtgtgc catacatatt catagttacg aattgaagat gatggatgga aatatcgatc   1500
taggataggt atacatgttg atgcgggttt tactgatgca atacagaga tgcttttgt     1560 tcgcttggtt gtgatgatgt ggtgtggttg ggcggtcgtt cattcgttct agatcggagt   1620
agaatactgt ttcaaactac ctggtgtatt tattaattt ggaactgtat gtgtgtgtca    1680
tacatcttca tagttacgag tttaagatgg atggaaatat cgatctagga taggtataca   1740
tgttgatgtg ggtttactg atgcatatac atgatggcat atgcagcatc tattcatatg   1800
ctctaacctt gagtacctat ctattataat aaacaagtat gttttataat tattttgatc    1860
ttgatatact tggatgatgg catatgcagc agctatatgt ggatttttt agccctgcct    1920 tcatacgcta tttatttgct tggtactgtt tcttttgtcg atgctcaccc tgttgtttgg    1980
tgttacttct gcagggatcc cctcgaggtc gaccatggtc cgtcctgtag aaaccccaac   2040
ccgtgaaatc aaaaaactcg acggcctgtg gcattcagt ctggatcgcg aaaactgtgg    2100
aattgatcag cgttggtggg aaagcgcgtt acaagaaagc cgggcaattg ctgtgccagg   2160 cagtttaac gatcagttcg ccgatgcaga tattcgtaat tatgcgggca acgtctggta    2220
tcagcgcgaa gtctttatac cgaaaggttg gcaggccag cgtatcgtgc tgcgtttcga    2280
tgcggtcact cattacggca aagtgtgggt caataatcag gaagtgatgg agcatcaggg   2340
cggctatacg ccatttgaag ccgatgtcac gccgtatgtt attgccggga aaagtgtacg   2400
taagtttctg cttctacctt tgatatatat ataataatta tcattaatta gtagtaatat   2460
aatatttcaa atattttttt caaaataaaa gaatgtagta tatagcaatt gcttttctgt   2520
```

-continued

```
agtttataag tgtgtatatt ttaatttata acttttctaa tatatgacca aaatttgttg    2580
atgtgcaggt atcaccgttt gtgtgaacaa cgaactgaac tggcagacta tcccgccggg    2640
aatggtgatt accgacgaaa acggcaagaa aaagcagtct tacttccatg atttctttaa    2700
ctatgccgga atccatcgca gcgtaatgct ctacaccacg ccgaacacct gggtggacga    2760
tatcaccgtg gtgacgcatg tcgcgcaaga ctgtaaccac cgtctgttg actggcaggt     2820 ggtggccaat ggtgatgtca gcgttgaact gcgtgatgcg gatcaacagg tggttgcaac    2880
tggacaaggc actagcggga cttttgcaagt ggtgaatccg cacctctggc aaccgggtga   2940
aggttatctc tatgaactgt gcgtcacagc caaaagccag acagagtgtg atatctaccc    3000
gcttcgcgtc ggcatccggt cagtggcagt gaagggcgaa cagttcctga ttaaccacaa    3060
accgttctac tttactggct ttggtcgtca tgaagatgcg gacttgcgtg caaaggatt     3120 cgataacgtg ctgatggtgc acgaccacgc attaatggac tggattgggg ccaactccta    3180
ccgtacctcg cattacccctt acgctgaaga gatgctcgac tgggcagatg aacatggcat   3240
cgtggtgatt gatgaaactg ctgctgtcgg ctttaacctc tctttaggca ttggtttcga    3300
agcgggcaac aagccgaaag aactgtacag cgaagaggca gtcaacgggg aaactcagca    3360
agcgcactta caggcgatta aagagctgat agcgcgtgac aaaaaccacc caagcgtggt    3420
gatgtggagt attgccaacg aaccggatac ccgtccgcaa ggtgcacggg aatatttcgc    3480
gccactggcg gaagcaacgc gtaaactcga cccgacgcgt ccgatcacct gcgtcaatgt    3540
aatgttctgc gacgctcaca ccgataccat cagcgatctc tttgatgtgc tgtgcctgaa    3600
ccgttattac ggatggtatg tccaaagcgg cgatttggaa acggcagaga aggtactgga    3660 aaagaactt ctggcctggc aggagaaact gcatcagccg attatcatca ccgaatacgg      3720
cgtggatacg ttagccgggc tgcactcaat gtacaccgac atgtggagtg aagagtatca    3780
gtgtgcatgg ctggatatgt atcaccgcgt ctttgatcgc gtcagcgccg tcgtcggtga    3840
acaggtatgg aatttcgccg attttgcgac ctcgcaaggc atattgcgcg ttggcggtaa    3900
caagaaaggg atcttcactc gcgaccgcaa accgaagtcg gcggcttttc tgctgcaaaa    3960
acgctggact ggcatgaact tcggtgaaaa accgcagcag ggaggcaaac aatgaatcaa    4020
caactctcct ggcgcaccat cgtcggctac agcctcggga attagatccc cgaatttccc    4080
cgatcgttca aacatttggc aataaagttt cttaagattg aatcctgttg ccggtcttgc    4140
gatgattatc atataatttc tgttgaatta cgttaagcat gtaataatta acatgtaatg    4200
catgacgtta tttatgagat gggttttat gattagagtc ccgcaattat acatttaata    4260
cgcgatagaa acaaaatat agcgcgcaaa ctaggataaa ttatcgcgcg cggtgtcatc     4320
tatgttacta gatcgggaat t                                              4341
```

<210> SEQ ID NO 48
<211> LENGTH: 2943
<212> TYPE: DNA
<213> ORGANISM: Artificial
<220> FEATURE:
<223> OTHER INFORMATION: artificial sequence Ubq3(At)-synGFPI-nos
      expression cassette

<400> SEQUENCE: 48

```
accggatttg gagccaagtc tcataaacgc cattgtggaa gaaagtcttg agttggtggt     60
aatgtaacag agtagtaaga acagagaaga gagagagtgt gagatacatg aattgtcggg    120
caacaaaaat cctgaacatc ttattttagc aaagagaaag agttccgagt ctgtagcaga    180
```

```
agagtgagga gaaatttaag ctcttggact tgtgaattgt tccgcctctt gaatacttct    240
tcaatcctca tatattcttc ttctatgtta cctgaaaacc ggcatttaat ctcgcgggtt    300
tattccggtt caacattttt tttgttttga gttattatct gggcttaata acgcaggcct    360
gaaataaatt caaggcccaa ctgtttttt ttttaagaag ttgctgttaa aaaaaaaaa     420 agggaattaa caacaacaac aaaaaaagat aaagaaaata ataacaatta ctttaattgt    480
agactaaaaa aacatagatt ttatcatgaa aaaagagaa agaaataaa aacttggatc      540 aaaaaaaaaa catacagatc ttctaattat taacttttct taaaaattag gtccttttc    600 ccaacaatta ggtttagagt tttggaatta accaaaaag attgttctaa aaaatactca    660
aatttggtag ataagtttcc ttattttaat tagtcaatgg tagatacttt tttttctttt    720
ctttattaga gtagattaga atcttttatg ccaagtattg ataaattaaa tcaagaagat    780
aaactatcat aatcaacatg aaattaaaag aaaaatctca tatatagtat tagtattctc    840
tatatatatt atgattgctt attcttaatg ggttgggtta accaagacat agtcttaatg    900
gaaagaatct tttttgaact ttttccttat tgattaaatt cttctataga aagaaagaa     960 attatttgag gaaagtata tacaaaaaga aaaatagaaa aatgtcagtg aagcagatgt   1020
aatggatgac ctaatccaac caccaccata ggatgtttct acttgagtcg gtcttttaaa   1080
aacgcacggt ggaaaatatg acacgtatca tatgattcct tcctttagtt tcgtgataat   1140
aatcctcaac tgatatcttc cttttttgt tttggctaaa gatatttat tctcattaat    1200 agaaaagacg gttttgggct tttggttttgc gatataaaga agaccttcgt gtggaagata   1260
ataattcatc ctttcgtctt tttctgactc ttcaatctct cccaaagcct aaagcgatct   1320
ctgcaaatct ctcgcgactc tctcttcaa ggtatatttt ctgattcttt ttgttttga     1380 ttcgtatctg atctccaatt tttgttatgt ggattattga atcttttgta taaattgctt   1440
ttgacaatat tgttcgtttc gtcaatccag cttctaaatt ttgtcctgat tactaagata   1500
tcgattcgta gtgtttacat ctgtgtaatt tcttgcttga ttgtgaaatt aggattttca   1560
aggacgatct attcaatttt tgtgttttct tgttcgatt ctctctgttt taggtttctt    1620
atgtttagat ccgtttctct ttggtgttgt tttgattct cttacggctt ttgatttggt    1680
atatgttcgc tgattggttt ctacttgttc tattgtttta tttcaggtgg atccaccatg   1740
ctgcagatga gcaagggcga ggagctgttc accggcgtgg tgccaatcct ggtggagctg   1800
gacggcgacg tgaacggcca caagttcagc gtgagcggcg agggcgaggg cgacgcgacc   1860
tacggcaagc tgaccctgaa gttcatctgt accaccggca agctcccggt cccgtggccg   1920
accctggtga ccaccttcac ctacggcgtg cagtgtttca gccgctaccc ggaccacatg   1980
aagcgccacg acttcttcaa gagcgccatg ccggagggca cgtaagtttc tgcttctac    2040 ctttgatata tatataataa ttatcattaa ttagtagtaa tataatattt caaatatttt   2100
tttcaaaata aaagaatgta gtatatagca attgcttttc tgtagtttat aagtgtgtat   2160 attttaatt ataacttttc taatatatga ccaaaatttg ttgatgtgca ggtgcaggag    2220
cgcaccatca gcttcaagga cgacggcaac tacaagaccc gcgccgaggt gaagttcgag   2280
ggcgacacac tagtgaaccg catcgagctg aagggcatcg acttcaagga ggacggcaac   2340
atcctgggcc acaagctgga gtacaactac aacagccaca tgtgtacat caccgcggac    2400 aagcagaaga acggcatcaa ggcgaacttc aagatccgcc acaatatcga ggacggcagc   2460
gtgcagctgg ccgaccacta ccagcagaac ccccgatcg gcgacggtcc tgtgctgctg    2520
ccggacaacc actacctgag cacccagagc gccctgagca aggacccgaa cgagaagcgc   2580
```

-continued

```
gaccacatgg tgctgctgga gttcgtgacc gccgccggca tcacccacgg catggacgag    2640
ctgtacaagg ttaactagag ctctagatcc ccgaatttcc ccgatcgttc aaacatttgg    2700
caataaagtt tcttaagatt gaatcctgtt gccggtcttg cgatgattat catataattt    2760
ctgttgaatt acgttaagca tgtaataatt aacatgtaat gcatgacgtt atttatgaga    2820
tgggttttta tgattagagt cccgcaatta tacatttaat acgcgataga aaacaaaata    2880
tagcgcgcaa actaggataa attatcgcgc gcggtgtcat ctatgttact agatcgggaa    2940
ttg                                                                  2943
```

<210> SEQ ID NO 49
<211> LENGTH: 4072
<212> TYPE: DNA
<213> ORGANISM: Artificial
<220> FEATURE:
<223> OTHER INFORMATION: artificial sequence Ubq3(At)-GIG-nos expression
      cassette

<400> SEQUENCE: 49

```
cggatttgga gccaagtctc ataaacgcca ttgtggaaga aagtcttgag ttggtggtaa      60
tgtaacagag tagtaagaac agagaagaga gagagtgtga gatacatgaa ttgtcgggca     120
acaaaaatcc tgaacatctt attttagcaa agagaaaaga ttccgagtct gtagcagaag    180
agtgaggaga aatttaagct cttggacttg tgaattgttc cgcctcttga atacttcttc    240
aatcctcata tattcttctt ctatgttacc tgaaaaccgg catttaatct cgcgggttta    300
ttccggttca acatttttt tgttttgagt tattatctgg gcttaataac gcaggcctga     360
aataaattca aggcccaact gttttttttt taagaagtt gctgttaaaa aaaaaaaag      420 ggaattaaca acaacaacaa aaaagataaa agaaaataat aacaattact ttaattgtag    480
actaaaaaaa catagatttt atcatgaaaa aagagaaaa gaaataaaaa cttggatcaa     540
aaaaaaacat acagatcttc taattattaa cttttcttaa aaattaggtc cttttttccca   600 acaattaggt ttagagtttt ggaattaaac caaaagatt gttctaaaaa atactcaaat     660
ttggtagata agtttcctta ttttaattag tcaatggtag atactttttt ttcttttctt    720
tattagagta gattagaatc ttttatgcca agtattgata aattaaatca agaagataaa    780
ctatcataat caacatgaaa ttaaaagaaa aatctcatat atagtattag tattctctat    840
atatattatg attgcttatt cttaatgggt tgggttaacc aagacatagt cttaatggaa    900
agaatctttt ttgaactttt tccttattga ttaaattctt ctatagaaaa gaaagaaatt    960
atttgaggaa aagtatatac aaaaagaaaa atagaaaat gtcagtgaag cagatgtaat    1020
ggatgaccta atccaaccac caccatagga tgtttctact tgagtcggtc ttttaaaaac   1080
gcacggtgga aaatatgaca cgtatcatat gattccttcc tttagtttcg tgataataat   1140
cctcaactga tatcttcctt tttttgtttt ggctaaagat attttattct cattaataga   1200
aaagacggtt ttgggctttt ggtttgcgat ataagaaga ccttcgtgtg aagataata    1260 attcatcctt tcgtcttttt ctgactcttc aatctctccc aaagcctaaa gcgatctctg   1320
caaatctctc gcgactctct ctttcaaggt atattctg attcttttg tttttgattc      1380 gtatctgatc tccaatttt gttatgtgga ttattgaatc ttttgtataa attgcttttg    1440
acaatattgt tcgtttcgtc aatccagctt ctaaattttg tcctgattac taagatatcg   1500
attcgtagtg tttacatctg tgtaatttct tgcttgattg tgaaattagg attttcaagg   1560
acgatctatt caattttgt gttttctttg ttcgattctc tctgttttag gtttcttatg    1620
```

-continued

```
tttagatccg tttctctttg gtgttgtttt gatttctctt acggcttttg atttggtata    1680
tgttcgctga ttggtttcta cttgttctat tgttttattt caggtggatc ccctcgaggt    1740
cgaccatggt ccgtcctgta gaaacccccaa cccgtgaaat caaaaaactc gacggcctgt    1800
gggcattcag tctggatcgc gaaaactgtg gaattgatca gcgttggtgg gaaagcgcgt    1860
tacaagaaag ccgggcaatt gctgtgccag gcagttttaa cgatcagttc gccgatgcag    1920
atattcgtaa ttatgcgggc aacgtctggt atcagcgcga agtctttata ccgaaaggtt    1980
gggcaggcca gcgtatcgtg ctgcgtttcg atgcggtcac tcattacggc aaagtgtggg    2040
tcaataatca ggaagtgatg gagcatcagg gcggctatac gccatttgaa gccgatgtca    2100
cgccgtatgt tattgccggg aaaagtgtac gtaagtttct gcttctacct ttgatatata    2160
tataataatt atcattaatt agtagtaata taatatttca aatattttt tcaaaataaa    2220
agaatgtagt atatagcaat tgcttttctg tagtttataa gtgtgtatat tttaattttat    2280
aacttttcta atatatgacc aaaatttgtt gatgtgcagg tatcaccgtt tgtgtgaaca    2340
acgaactgaa ctggcagact atcccgccgg gaatggtgat taccgacgaa acggcaaga    2400
aaaagcagtc ttacttccat gatttcttta actatgccgg aatccatcgc agcgtaatgc    2460
tctacaccac gccgaacacc tgggtggacg atatcaccgt ggtgacgcat gtcgcgcaag    2520
actgtaacca cgcgtctgtt gactggcagg tggtggccaa tggtgatgtc agcgttgaac    2580
tgcgtgatgc ggatcaacag gtggttgcaa ctggacaagg cactagcggg actttgcaag    2640
tggtgaatcc gcacctctgg caaccgggtg aaggttatct ctatgaactg tgcgtcacag    2700
ccaaaagcca gacagagtgt gatatctacc cgcttcgcgt cggcatccgg tcagtggcag    2760
tgaagggcga acagttcctg attaaccaca accgttctca ctttactggc tttggtcgtc    2820
atgaagatgc ggacttgcgt ggcaaaggat tcgataacgt gctgatggtg cacgaccacg    2880
cattaatgga ctggattggg gccaactcct accgtacctc gcattaccct tacgctgaag    2940
agatgctcga ctggcagat gaacatggca tcgtggtgat tgatgaaact gctgctgtcg    3000
gctttaacct ctctttaggc attggtttcg aagcgggcaa caagccgaaa gaactgtaca    3060
gcgaagaggc agtcaacggg gaaactcagc aagcgcactt acaggcgatt aaagagctga    3120
tagcgcgtga caaaaaccac ccaagcgtgg tgatgtggag tattgccaac gaaccggata    3180
cccgtccgca aggtgcacgg gaatatttcg cgccactggc ggaagcaacg cgtaaactcg    3240
acccgacgcg tccgatcacc tgcgtcaatg taatgttctg cgacgctcac accgatacca    3300
tcagcgatct cttttgatgtg ctgtgcctga accgttatta cggatggtat gtccaaagcg    3360
gcgatttgga aacggcagag aaggtactgg aaaaagaact tctggcctgg caggagaaac    3420
tgcatcagcc gattatcatc accgaatacg gcgtggatac gttagccggg ctgcactcaa    3480
tgtacaccga catgtggagt gaagagtatc agtgtgcatg gctggatatg tatcaccgcg    3540
tctttgatcg cgtcagcgcc gtcgtcggtg aacaggtatg gaatttcgcc gattttgcga    3600
cctcgcaagg catattgcgc gttggcggta acaagaaagg gatcttcact cgcgaccgca    3660
aaccgaagtc ggcggctttt ctgctgcaaa acgctggac tggcatgaac ttcggtgaaa    3720
aaccgcagca gggaggcaaa caatgaatca acaactctcc tggcgcacca tcgtcggcta    3780
cagcctcggg aattagatcc ccgaatttcc ccgatcgttc aaacatttgg caataaagtt    3840
tcttaagatt gaatcctgtt gccggtcttg cgatgattat catataattt ctgttgaatt    3900
acgttaagca tgtaataatt aacatgtaat gcatgacgtt atttatgaga tgggttttta    3960
```

-continued

| | |
|---|---|
| tgattagagt cccgcaatta tacatttaat acgcgataga aaacaaaata tagcgcgcaa | 4020 |
| actaggataa attatcgcgc gcggtgtcat ctatgttact agatcgggaa tt | 4072 |

CESTRUM YELLOW LEAF CURLING VIRUS PROMOTERS

This application is a national stage application under 35 U.S.C. § 371 of International Application No. PCT/EP01/03408, filed Mar. 26, 2001, which is incorporated herein by reference, which is entitled to the benefit of U.S. Provisional Appln. Ser. No. 60/272,076, filed Feb. 28, 2001, which is incorporated herein by reference.

The present invention relates to novel DNA sequences that function as promoters of transcription of associated nucleotide sequences in plants. More specifically, this invention relates to novel promoters that confer constitutive expression to an associated nucleotide sequence of interest.

In the field of agriculture there exists a continuous desire to modify plants according to one's needs. One way to accomplish this is by using modern genetic engineering techniques. For example, by introducing a gene of interest into a plant, the plant can be specifically modified to express a desirable phenotypic trait. For this, plants are transformed most commonly with a heterologous gene comprising a promoter region, a coding region and a termination region. When genetically engineering a heterologous gene for expression in plants, the selection of a promoter is a critical factor. While it may be desirable to express certain genes only in response to particular stimuli or confined to specific cells or tissues, other genes are more desirably expressed constitutively, i.e. throughout the plant at all times and in most tissues and organs. In the past, the 35S promoter from Cauliflower Mosaic Virus (CaMV 35S promoter) has been widely used for constitutive expression of heterologous genes in plants. There are, however, occasions where it is desirable to use alternative promoters. Therefore, it is a major objective of the present invention to provide such alternative promoters for expression of a nucleotide sequence of interest in plants. The invention also provides recombinant DNA molecules, expression vectors and transgenic plants comprising the promoters of the present invention.

The present invention thus provides:

a DNA sequence capable of driving expression of an associated nucleotide sequence, wherein said DNA sequence is obtainable from the genome of Cestrum yellow leaf curling virus (CmYLCV). Preferred is a DNA sequence which is obtainable from the CmYLCV full-length transcript promoter and comprises the nucleotide sequence depicted in SEQ ID NO:1.

In particular, DNA sequences are provided, wherein
said DNA sequence comprises the nucleotide sequence depicted in SEQ ID NO:2
said DNA sequence comprises the nucleotide sequence depicted in SEQ ID NO:3
said DNA sequence comprises the nucleotide sequence depicted in SEQ ID NO:4
said DNA sequence comprises the nucleotide sequence depicted in SEQ ID NO:5
said DNA sequence comprises the nucleotide sequence depicted in SEQ ID NO:6
said DNA sequence hybridizes under stringent conditions to any one of SEQ ID NO:1, SEQ ID NO:2, SEQ ID NO:3, SEQ ID NO:4, SEQ ID NO:5 or SEQ ID NO:6, in particular wherein the DNA sequence as mentioned hereinbefore comprises the nucleotide sequence depicted in SEQ ID NO:19 or SEQ ID NO:20.

The invention further provides DNA sequences comprising a consecutive stretch of at least 50 nt, preferably of between about 400 bases and about 650 bases, more preferably of between about 200 bases and about 400 bases and most preferably of about 350 bases in length of SEQ ID NO:1, wherein said DNA sequences are capable of driving expression of an associated nucleotide sequence.

In a particular embodiment of the invention said consecutive stretch of at least 50 nt, preferably of between about 400 bases and about 650 bases, more preferably of between about 200 bases and about 400 bases and most preferably of about 350 bases in length has at least 75%, preferably 80%, more preferably 90% and most preferably 95% sequence identity with a corresponding consecutive stretch of at least 50 nt, preferably of between about 400 bases and about 650 bases, more preferably of between about 200 bases and about 400 bases and most preferably of about 350 bases in length of SEQ ID NO:1.

The invention further provides recombinant DNA molecules comprising a full-length transcript promoter region isolated from Cestrum yellow leaf curling virus. In addition, the invention provides recombinant DNA molecules and DNA expression cassettes comprising a DNA sequence according to the invention operably linked to a nucleotide sequence of interest. The invention also provides DNA expression vectors comprising said recombinant DNA and expression cassettes, respectively.

In particular, recombinant DNA molecules and DNA expression cassettes are provided wherein the nucleotide sequence of interest comprises a coding sequence, particularly wherein the coding sequence encodes a desirable phenotypic trait the coding sequence encodes a selectable or screenable marker gene the coding sequence encodes a protein conferring antibiotic resistance, virus resistance, insect resistance, disease resistance, or resistance to other pests, herbicide tolerance, improved nutritional value, improved performance in an industrial process or altered reproductive capability the coding sequence encodes a protein which confers a positive selective advantage to cells that have been transformed with said coding sequence the coding sequence encodes a protein which confers a metabolic advantage to cells that have been transformed with said coding sequence consisting of being able to metabolize a compound, wherein said compound is mannose or xylose or a derivative or a precursor of these, or a substrate of the protein, or is capable of being metabolized by cells transformed with said coding sequence into such a substrate the coding sequence encodes an enzyme selected from the group of xyloisomerases, phosphomanno-isomerase, mannose-6-phosphate isomerase, mannose-1-phosphate isomerase, phosphomanno mutase, mannose epimerase, mannose or xylose phosphatase, mannose-6-phosphatase, mannose-1-phosphatase and mannose or xylose permease the coding sequence encodes a phosphomanno isomerase the coding region is non-translatable the non-translatable coding region is from a viral gene, in particular from TSWV, more particularly from the TSWV NP gene the coding sequence encodes commercially valuable enzymes or metabolites in the plant the coding sequence is in antisense orientation The invention also provides DNA expression vectors comprising a DNA sequence or a recombinant DNA molecule as mentioned hereinbefore. In a particular embodiment of the invention, said DNA expression vector is pNOV2819 or pNOV2819. Further are provided DNA expression vectors comprising a first DNA sequence according to the invention operably linked to a nucleotide sequence of interest, and a second DNA sequence according to the invention operably linked to a nucleotide sequence of interest. In a specific embodiment of the invention the DNA expression vectors as mentioned hereinbefore are capable of altering the expression of a viral genome.

In an even more specific embodiment, the DNA expression vector as mentioned hereinbefore comprises a first DNA sequence capable of expressing in a cell a sense RNA fragment of said viral genome or portion thereof and a second DNA sequence capable of expressing in a cell an antisense RNA fragment of said viral genome or portion thereof, wherein said sense RNA fragment and said antisense RNA fragment are capable of forming a double-stranded RNA.

Expression vectors as mentioned hereinbefore are provided wherein

- said virus is selected from the group consisting of tospoviruses, potyviruses, potexviruses, tobamoviruses, luteoviruses, cucumoviruses, bromoviruses, closteoviruses, tombusviruses and furoviruses
- said DNA sequences comprises a nucleotide sequence derived from a viral coat protein gene, a viral nucleocapsid protein gene, a viral replicase gene, or a viral movement protein gene or portions thereof
- said DNA sequence is derived from tomato spotted wilt virus (TSWV)
- said DNA is derived from a nucleocapsid protein gene The invention further provides host cells stably transformed with a DNA sequence, a recombinant DNA molecule or a DNA expression vector according to the invention. In particular, wherein

- the host cell is a bacterium
- the host cell is a plant cell
- the host cell is a plant cell selected from the group consisting of rice, maize, wheat, barley, rye, sweet potato, sweet corn, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugar-beet, sunflower, rapeseed, clover, tobacco, carrot, cotton, alfalfa, potato, eggplant, cucumber, *Arabidopsis thaliana*, and woody plants such as coniferous and deciduous trees, but particularly rice, maize, wheat, barley, cabbage, cauliflower, pepper, squash, melon, soybean, tomato, sugar-beet, sunflower or cotton, rice, maize, wheat, *Sorghum bicolor*, orchardgrass, sugar beet and soybean cells
- the host cell is a plant cell from a dicotyledonous plant
- the host cell is a plant cell from a dicotyledonous plant selected from the group consisting of soybean, cotton, tobacco, sugar beet and oilseed rape
- the host cell is a plant cell from a monocotyledonous plant
- the host cell is a plant cell from a monocotyledonous plant selected from the group consisting of maize, wheat, sorghum, rye, oats, turf grass, rice, and barley.

In addition, plants and the progeny thereof including seeds are provided stably transformed with a DNA sequence, a recombinant DNA molecule or a DNA expression vector according to the invention. In particular, wherein

- the plant is selected from the group consisting of rice, maize, wheat, barley, rye, sweet potato, sweet corn, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugar-beet, sunflower, rapeseed, clover, tobacco, carrot, cotton, alfalfa, potato, eggplant, cucumber, *Arabidopsis thaliana*, and woody plants such as coniferous and deciduous trees, but particularly rice, maize, wheat, barley, cabbage, cauliflower, pepper, squash, melon, soybean, tomato, sugar-beet, sunflower or cotton, rice, maize, wheat, *Sorghum bicolor*, orchardgrass, sugar beet and soybean.

The present invention further discloses

- the use of the DNA sequence according to the invention to express a nucleotide sequence of interest
- a method of producing a DNA sequence according to the invention, wherein the DNA is produced by a polymerase chain reaction wherein at least one oligonucleotide used comprises a sequence of nucleotides which represents a consecutive stretch of 15, 18, 20, 22, 24 or more base pairs of SEQ ID NO:1.

In order to ensure a clear and consistent understanding of the specification and the claims, the following definitions are provided:

CmYLCV: Cestrum yellow leaf curling virus.

DNA shuffling: DNA shuffling is a method to rapidly, easily and efficiently introduce rearrangements, preferably randomly, in a DNA molecule or to generate exchanges of DNA sequences between two or more DNA molecules, preferably randomly. The DNA molecule resulting from DNA shuffling is a shuffled DNA molecule that is a non-naturally occurring DNA molecule derived from at least one template DNA molecule.

Expression: refers to the transcription and/or translation of an endogenous gene or a transgene in plants. In the case of antisense constructs, for example, expression may refer to the transcription of the antisense DNA only.

Functionally equivalent sequence: refers to a DNA sequence which has promoter activity substantially similar to the CmYLCV full-length transcript promoter or parts thereof and which under stringent hybridizing conditions hybridizes with the said promoter sequences.

Gene: refers to a coding sequence and associated regulatory sequence wherein the coding sequence is transcribed into RNA such as mRNA, rRNA, tRNA, snRNA, sense RNA or antisense RNA. Examples of regulatory sequences are promoter sequences, 5'- and 3'-untranslated sequences and termination sequences. Further elements that may be present are, for example, introns.

Gene of interest: refers to any gene which, when transferred to a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability. The "gene of interest" may also be one that is transferred to plants for the production of commercially valuable enzymes or metabolites in the plant.

Heterologous as used herein means of different natural or of synthetic origin. For example, if a host cell is transformed with a nucleic acid sequence that does not occur in the untransformed host cell, that nucleic acid sequence is said to be heterologous with respect to the host cell. The transforming nucleic acid may comprise a heterologous promoter, heterologous coding sequence, or heterologous termination sequence. Alternatively, the transforming nucleic acid may be completely heterologous or may comprise any possible combination of heterologous and endogenous nucleic acid sequences.

Leader region: region in a gene between transcription start site and translation start site.

Marker gene: refers to a gene encoding a selectable or screenable trait.

Operably linked to/associated with: a regulatory DNA sequence is said to be "operably linked to" or "associated with" a DNA sequence that codes for an RNA or a protein if the two sequences are situated such that the regulatory DNA sequence affects expression of the coding DNA sequence.

Plant: refers to any plant, particularly to seed plants

Plant cell: structural and physiological unit of the plant, comprising a protoplast and a cell wall. The plant cell may be in form of an isolated single cell or a cultured cell, or as a part of higher organized unit such as, for example, a plant tissue, or a plant organ.

Plant material: refers to leaves, stems, roots, flowers or flower parts, fruits, pollen, pollen tubes, ovules, embryo sacs, egg cells, zygotes, embryos, seeds, cuttings, cell or tissue cultures, or any other part or product of a plant Promoter: refers to a DNA sequence that initiates transcription of an associated DNA sequence. The promoter region may also include elements that act as regulators of gene expression such as activators, enhancers, and/or repressors and may include all or part of the 5' non-translated leader sequence.

Recombinant DNA molecule: a combination of DNA sequences that are joined together using recombinant DNA technology.

Recombinant DNA technology: procedures used to join together DNA sequences as described, for example, in Sambrook et al., 1989, Cold Spring Harbor, N.Y.: Cold Spring Harbor Laboratory Press.

Screenable marker gene: refers to a gene whose expression does not confer a selective advantage to a transformed cell, but whose expression makes the transformed cell phenotypically distinct from untransformed cells.

Selectable marker gene: refers to a gene whose expression in a plant cell gives the cell a selective advantage. The selective advantage possessed by the cells transformed with the selectable marker gene may be due to their ability to grow in the presence of a negative selective agent, such as an antibiotic or a herbicide, compared to the growth of non-transformed cells. The selective advantage possessed by the transformed cells, compared to non-transformed cells, may also be due to their enhanced or novel capacity to utilize an added compound as a nutrient, growth factor or energy source. Selectable marker gene also refers to a gene or a combination of genes whose expression in a plant cell in the presence of the selective agent, compared to the absence of the selective agent, has a positive effect on the transformed plant cell and a negative effect on the un-transformed plant cell, for example with respect to growth, and thus gives the transformed plant cell a positive selective advantage.

Sequence identity: the percentage of sequence identity is determined using computer programs that are based on dynamic programming algorithms. Computer programs that are preferred within the scope of the present invention include the BLAST (Basic Local Alignment Search Tool) search programs designed to explore all of the available sequence databases regardless of whether the query is protein or DNA. Version BLAST 2.0 (Gapped BLAST) of this search tool has been made publicly available on the Internet (currently http://www.ncbi.nlm.nih.gov/BLAST/). It uses a heuristic algorithm, which seeks local as opposed to global alignments and is therefore able to detect relationships among sequences, which share only isolated regions. The scores assigned in a BLAST search have a well-defined statistical interpretation. Said programs are preferably run with optional parameters set to the default values.

Transformation: refers to the introduction of a nucleic acid into a cell. In particular, it refers to the stable integration of a DNA molecule into the genome of an organism of interest TSWV: tomato spotted wilt virus The present invention relates to DNA sequences obtainable from the genome of the Cestrum yellow leaf curling virus (CmYLCV). Preferred are DNA sequences which are obtainable from the CmYLCV full-length transcript promoter which are capable of driving expression of an associated nucleotide sequence of interest. DNA sequences comprising functional and/or structural equivalents thereof are also embraced by the invention. The present invention thus relates to DNA sequences that function as promoters of transcription of associated nucleotide sequences. The promoter region may also include elements that act as regulators of gene expression such as activators, enhancers, and/or repressors and may include the 5' non-translated leader sequence of the transcribed mRNA.

In a preferred embodiment of the invention, said DNA sequence confers constitutive expression to an associated nucleotide sequence. Constitutive expression means that the nucleotide sequence of interest is expressed at all times and in most tissues and organs. When tested in association with a GUS or CAT reporter gene in transient expression assays, the DNA sequence according to the invention confers high level of expression of the GUS or CAT reporter gene. Thus, the DNA sequence according to the invention is useful for high level expression of an associated nucleotide sequence of interest, which preferably is a coding sequence. It is known to the skilled artisan that the associated coding sequence of interest can be expressed in sense or in antisense orientation. Further, the coding sequence of interest may be of heterologous or homologous origin with respect to the plant to be transformed. In case of a homologous coding sequence, the DNA sequence according to the invention is useful for ectopic expression of said sequence. In one particular embodiment of the invention expression of the coding sequence of interest under control of a DNA sequence according to the invention suppresses its own expression and that of the original copy of the gene by a process called cosuppression.

The promoters of the present invention can be obtained from Cestrum yellow leaf curling virus (CmYLCV) genomic DNA, which can be isolated, for example, from infected *Cestrum parqui* plants. CmYLCV-infected *Cestrum parqui* plants are identified by their leaf mosaic and crinkled leaf malformation. This DNA is then sequenced and analyzed. Sequence comparison with sequences in the database shows that the genomic organization of the CmYLCV is related to the one of other members of the Caulimovirus family. CmYLCV contains 8 open reading frames. Sequence comparison of the CmYLCV gene products shows that gene I product is involved in intracellular movements: gene A encodes a small protein of unknown function, gene B codes for the aphid transmission factor; gene C encodes a virion associated protein; the gene IV is the major capsid protein; gene V codes for a reverse transcriptase and the gene VI activates in trans the translation of viral genes on full-length transcript. Of particular interest is the so-called CmYLCV full-length transcript promoter.

It is known to the skilled artisan that various regions of the CmYLCV full-length transcript promoter can be used according to the invention. One particular embodiment of the invention is the CmYLCV full-length transcript promoter region shown in SEQ ID NO:1, called the CmpD promoter. This sequence contains 350 bp of CmYLCV full-length transcript promoter and 320 bp of the CmYLCV full-length transcript 5' non-translated leader sequence. This sequence is obtained by sequencing the CmYLCV genomic DNA. The promoter and leader sequences respectively, are identified by comparison to sequences in the database. A variant of SEQ ID NO:1, called CmpE, wherein the CmYLCV full-length transcript 5' non-translated leader sequence is 318 bp instead of 320 bp in length, is shown in SEQ ID NO:19.

One preferred embodiment of the invention is the DNA sequence depicted in SEQ ID NO:2, called the CmpC promoter. The CmpC promoter is a fragment of the sequence shown in SEQ ID NO:1 and contains 346 bp of CmYLCV full-length transcript promoter, corresponding to base 5 to 350 of SEQ ID NO:1. This DNA sequence is obtainable by PCR with genomic DNA from Cestrum yellow leaf curling virus or from Cestrum yellow leaf curling virus-infected *Cestrum parqui* plants using forward primer Cmp1 (SEQ ID NO:13) and reverse primer CmpC2 (SEQ ID NO:14). The putative TATA-box of the CmpC promoter is located from base 308 to base 315 of SEQ ID NO:2. The CmpC promoter contains at least 3 putative enhancer regions. Enhancer region 1 having the nucleotide sequence CAAT is located from base 232 to base 235 of SEQ ID NO:2, and enhancer region 2 also having the nucleotide sequence CAAT is located from base 243 to base 246 of SEQ ID NO:2. Enhancer region 3 is located from base 246 to base 253 of SEQ ID NO:2 and has the nucleotide sequence TGACG-TAA.

Another preferred embodiment of the invention is the DNA shown in SEQ ID NO:3, called the CmpS promoter. The CmpS promoter also is a fragment of the sequence shown in SEQ ID NO: 1 and contains the 346 bp of SEQ ID NO:2 plus 54 bp from the leader region of the CmYLCV full-length transcript promoter. The leader region is a nucleotide sequence preceding the coding region which is transcribed but not translated into protein. It is known to the skilled artisan that the leader region can contain regulatory elements with important functions in gene expression. The CmpS promoter is obtainable by PCR with genomic DNA from Cestrum yellow leaf curling virus or from Cestrum yellow leaf curling virus-infected *Cestrum parqui* plants using forward primer Cmp1 (SEQ ID NO:13) and reverse primer CmpS2 (SEQ ID NO:15). The CmpS promoter contains at least 2 putative enhancer regions in the leader region. Enhancer region 4 (GAGAGA) is located at base 354 to base 359 of SEQ ID NO:3 and enhancer region 5 (GAGAGAGA) is located at base 368 to base 375 of SEQ ID NO:3.

Yet another preferred embodiment of the invention is the sequences depicted in SEQ ID NO:4, called the CmpL promoter. As the preceding promoters, the CmpL promoter is a fragment of the sequence shown in SEQ ID NO: 1 and contains the 346 bp of SEQ ID NO:2 plus 288 bp of the CmYLCV full-length transcript 5' non-translated leader sequence. The CmpL promoter is obtainable by PCR with genomic DNA from Cestrum yellow leaf curling virus or from Cestrum yellow leaf curling virus-infected *Cestrum parqui* plants using forward primer Cmp1 (SEQ ID NO:13) and reverse primer CmpL2 (SEQ ID NO:16). A variant of SEQ ID NO:4, called CmpF, wherein the CmYLCV full-length transcript 5' non-translated leader sequence is 286 bp instead of 288 bp in length, is shown in SEQ ID NO:20.

It is known to the skilled artisan that the nucleotide sequences shown in SEQ ID NOs:1, 2, 3, 4, 19 and 20 can be extended at their 5-' and 3'-ends with homologous or heterologous nucleotide sequences. For example, the 5'-end of SEQ ID NOs:1, 2, 3, 4, 19 and 20 can be extended by all or part of the nucleotides shown in SEQ ID NO:6. SEQ ID NO:6 is naturally found upstream of SEQ ID NOs: 2, 3, 4 and 20 and contains part of ORF VI of CmYLCV (base 1 to base 100 of SEQ ID NO:6) as well as part of the CmYLCV full-length transcript promoter (base 101 to base 104 of SEQ ID NO:6). Likewise, the 3'-ends of SEQ ID NOs:2, 3, 4 and 20 can be extended by all or part of the nucleotides shown in SEQ ID NO:5, representing the nucleotide sequence naturally found at the 3'-end of SEQ ID NOs:4 and 20 and comprising part of the CmYLCV full-length transcript leader sequence.

As described above, the DNA sequences of the invention can be obtained, for example, by PCR with genomic DNA from Cestrum yellow leaf curling virus or from Cestrum yellow leaf curling virus-infected *Cestrum parqui* plants. Alternatively, the DNA sequences of the invention can be obtained from any other virus of the Caulimovirus family comprising homologues of the DNA sequence of the invention using sequence specific primers.

It is apparent to the skilled artisan that, based on the nucleotide sequences shown in SEQ ID NO:1 to SEQ ID NO:6 and SEQ ID Nos 19 and 20, any primer combination of interest can be chosen to PCR amplify DNA fragments of various lengths that can be used according to the invention. The invention thus includes fragments derived from the CmYLCV full-length transcript promoters that function according to the invention, i.e. are capable of conferring expression of an associated nucleotide sequence.

This can be tested by generating such promoter fragments, fusing them to a selectable or screenable marker gene and assaying the fusion constructs for retention of promoter activity. Such assays are within the ordinary skill of the person skilled in the art. Preferred DNA fragments of the invention are of at least about 50 bases, preferably of between about 400 bases and about 650 bases, more preferably of between about 200 bases and about 400 bases and most preferably of about 350 bases in length.

It is also clear to the skilled artisan that mutations, insertions, deletions and/or substitutions of one or more nucleotides can be introduced into the DNA sequences of SEQ ID NOs:1, 2, 3, 4, 5 and 6 or longer or shorter fragments derived from the sequence information thereof using methods known in the art. In addition, an unmodified or modified nucleotide sequence of the present invention can be varied by shuffling the sequence of the invention. To test for a function of variant DNA sequences according to the invention, the sequence of interest is operably linked to a selectable or screenable marker gene and expression of the marker gene is tested in transient expression assays with protoplasts or in stably transformed plants. It is known to the skilled artisan that DNA sequences capable of driving expression of an associated nucleotide sequence are build in a modular way. Accordingly, expression levels from shorter DNA fragments may be different than the one from the longest fragment and may be different from each other. For example, deletion of a down-regulating upstream element will lead to an increase in the expression levels of the associated nucleotide sequence while deletion of an upregulating element will decrease the expression levels of the associated nucleotide sequence. It is also known to the skilled artisan that deletion of development-specific or a tissue-specific element will lead to a temporally or spatially altered expression profile of the associated nucleotide sequence. Embraced by the present invention are also functional equivalents of the promoters of the present invention, i.e. nucleotide sequences that hybridize under stringent conditions to any one of SEQ ID NO:1, SEQ ID NO:2, SEQ ID NO:3, SEQ ID NO:4, SEQ ID NO:5 or SEQ ID NO:6, such as, for example, the sequences shown in SEQ ID NO:19 and SEQ ID NO:20. A stringent hybridization is performed at a temperature of 65° C., preferably 60° C. and most preferably 55° C. in double strength (2×) citrate buffered saline (SSC) containing 0.1% SDS followed by rinsing of the support at the same temperature but with a buffer having a reduced SSC concentration. Such reduced concentration buffers are typically one tenth strength SSC (0.1×SSC) containing 0.1% SDS, preferably 0.2×SSC containing 0.1% SSC and most preferably half strength SSC (0.5×SSC) containing 0.1% SDS. In fact, functional equivalents to all or part of the CmYLCV full-length transcript promoter from other organisms can be found by hybridizing any one of SEQ ID NO:1, SEQ ID NO:2, SEQ ID NO:3, SEQ ID NO:4, SEQ ID NO:5, SEQ ID NO:6, SEQ ID NO:19 or SEQ ID NO:20 with genomic DNA isolated from an organism of interest, particularly from another Caulimovirus.

The skilled artisan knows how to proceed to find such sequences as there are many ways known in the art to identify homologous sequences in other organisms. Such newly identified DNA molecules then can be sequenced and the sequence can be compared to any one of SEQ ID NO:1, SEQ ID NO:2, SEQ ID NO:3, SEQ ID NO:4, SEQ ID NO:5, SEQ ID NO:6, SEQ ID NO:19 or SEQ ID NO:20 and tested for promoter activity. Within the scope of the present invention are DNA molecules having at least 75%, preferably 80%, more preferably 90%, and most preferably 95% sequence identity to the nucleotide sequence of any one of SEQ ID Nos:1, 2, 3, 4 or 6 over a length of at least 50 nucleotides. The percentage of sequence identity is determined using computer programs that are based on dynamic programming algorithms. Computer programs that are preferred within the scope of the present invention include the BLAST (Basic Local Alignment Search Tool) search programs designed to explore all of the available sequence databases regardless of whether the query is protein or DNA. Version BLAST 2.0 (Gapped BLAST) of this search tool has been made publicly available on the Internet, at the NCBI web site. It uses a heuristic algorithm which seeks local as opposed to global alignments and is therefore able to detect relationships among sequences which share only isolated regions. The scores assigned in a BLAST search have a well-defined statistical interpretation. Said programs are preferably run with optional parameters set to the default values.

It is another object of the present invention to provide recombinant DNA molecules comprising a DNA sequence according to the invention operably linked to a nucleotide sequence of interest. The nucleotide sequence of interest can, for example, code for a ribosomal RNA, an antisense RNA or any other type of RNA that is not translated into protein. In another preferred embodiment of the invention the nucleotide sequence of interest is translated into a protein product. The nucleotide sequence associated with the promoter sequence may be of homologous or heterologous origin with respect to the plant to be transformed. The sequence may also be entirely or partially synthetic. Regardless of the origin, the associated DNA sequence will be expressed in the transformed plant in accordance with the expression properties of the promoter to which it is linked. In case of homologous nucleotide sequences associated with the promoter sequence, the promoter according to the invention is useful for ectopic expression of said homologous sequences. Ectopic expression means that the nucleotide sequence associated with the promoter sequence is expressed in tissues and organs and/or at times where said sequence may not be expressed under control of its own promoter. In one particular embodiment of the invention, expression of nucleotide sequence associated with the promoter sequence suppresses its own expression and that of the original copy of the gene by a process called cosuppression.

In a preferred embodiment of the invention the associated nucleotide sequence may code for a protein that is desired to be expressed throughout the plant at all times and in most tissues and organs. Such nucleotide sequences preferably encode proteins conferring a desirable phenotypic trait to the plant transformed therewith. Examples are nucleotide sequences encoding proteins conferring antibiotic resistance, virus resistance, insect resistance, disease resistance, or resistance to other pests, herbicide tolerance, improved nutritional value, improved performance in an industrial process or altered reproductive capability. The associated nucleotide sequence may also be one that is transferred to plants for the production of commercially valuable enzymes or metabolites in the plant. Embraced by the present invention are also selectable or screenable marker genes, i.e. genes comprising a DNA sequence of the invention operably linked to a coding region encoding a selectable or screenable trait.

Examples of selectable or screenable marker genes are described below. For certain target species, different antibiotic or herbicide selection markers may be preferred. Selection markers used routinely in transformation include the nptII gene which confers resistance to kanamycin, paromomycin, geneticin and related antibiotics (Vieira and Messing, 1982, Gene 19: 259–268; Bevan et al., 1983, Nature 304: 184–187) the bacterial aadA gene (Goldschmidt-Clermont, 1991, Nucl. Acids Res. 19: 4083–4089), encoding aminoglycoside 3'-adenylyltransferase and conferring resistance to streptomycin or spectinomycin, the hph gene which confers resistance to the antibiotic hygromycin (Blochlinger and Diggelmann, 1984, Mol. Cell. Biol. 4: 2929–2931), and the dhfr gene, which confers resistance to methotrexate (Bourouis and Jarry, 1983, EMBO J. 2: 1099–1104). Other markers to be used include a phosphinothricin acetyltransferase gene, which confers resistance to the herbicide phosphinothricin (White et al., 1990, Nucl. Acids Res. 18: 1062; Spencer et al. 1990, Theor. Appl. Genet. 79: 625–631), a mutant EPSP synthase gene encoding glyphosate resistance (Hinchee et al., 1988, Bio/Technology 6: 915–922), a mutant acetolactate synthase (ALS) gene which confers imidazolione or sulfonylurea resistance (Lee et al., 1988, EMBO J. 7: 1241–1248), a mutant psbA gene conferring resistance to atrazine (Smeda et al., 1993, Plant Physiol. 103: 911–917), or a mutant protoporphyrinogen oxidase gene as described in EP 0 769 059. Identification of transformed cells may also be accomplished through expression of screenable marker genes such as genes coding for chloramphenicol acetyl transferase (CAT), β-glucuronidase (GUS), luciferase (LUC), and green fluorescent protein (GFP) or any other protein that confers a phenotypically distinct trait to the transformed cell. Selection markers resulting in positive selection, such as a phosphomannose isomerase gene, as described in patent application WO 93/05163, are also used. Other genes to be used for positive selection are described in WO 94/20627 and encode xyloisomerases and phosphomanno-isomerases such as mannose-6-phosphate isomerase and mannose-1-phosphate isomerase; phosphomanno mutase; mannose epimerases such as those which convert carbohydrates to mannose or mannose to carbohydrates such as glucose or galactose; phosphatases such as mannose or xylose phosphatase, mannose-6-phosphatase and mannose-1-phosphatase, and permeases which are involved in the transport of mannose, or a derivative, or a precursor thereof into the cell. The agent which reduces the toxicity of the compound to the cells is typically a glucose derivative such as methyl-3-O-glucose or phloridzin. Transformed cells are identified without damaging or killing the non-transformed cells in the population and without co-introduction of antibiotic or herbicide resistance genes. As described in WO 93/05163, in addition to the fact that the need for antibiotic or herbicide resistance genes is eliminated, it has been shown that the positive selection method is often far more efficient than traditional negative selection.

Therefore, the promoters of the present invention are preferably operably linked to a nucleotide sequence which encodes a protein which comprises a region which: (a) encodes a protein which is involved in the metabolism of the compound, and/or (b) regulates the activity of the gene encoding the protein, wherein the compound is mannose or xylose or a derivative or a precursor of these, or a substrate of the protein, or is capable of being metabolized by the transformed cells into such a substrate. Said nucleotide sequence may encode a mannose-6-phosphate isomerase and the compound may be mannose. Alternatively, the nucleotide sequence may encode a phosphosugar-isomerase, a phosphosugar-mutase such as phosphomanno mutase, a phosphatase such as mannose-6-phosphatase, a sugar-epimerase, a sugar-permease, a phosphosugar-permease or a xylose isomerase, and the compound may be mannose, mannose-6-phosphate, D-mannoseamine or xylose.

In a preferred embodiment of the invention, the promoters of the invention are operably linked to the coding region of the *E. coli* manA gene (Joersbo and Okkels, 1996, Plant Cell Reports 16:219–221, Negrotto et al., 2000, Plant Cell Reports 19:798–803), encoding a phosphomannose isomerase (PMI), and a Nos (nopaline synthetase) terminator obtained from *Agrobacterium tumefaciens* T-DNA (Depicker et al., J. Mol. Appl. Genet. 1 (6), 561–573 (1982)). The skilled artisan knows that the Nos terminator may be substituted for by any other terminator that functions in plants. The promoter of the invention may be the CmpD, CmpC, CmpS, CmpL, CmpB, CmpA, CmpE or CmpF promoter, depicted in SEQ ID Nos 1 to 6 and 19 to 20, or any promoter derived therefrom. In an even more preferred embodiment of the invention, the promoter is the CmpS promoter depicted in SEQ ID NO:3.

The promoters of the present invention may also be used to provide resistance or tolerance to viruses by operatively linking the promoters of the invention with coding regions of genes from viruses to be controlled.

For virus control of negative strand viruses such as tomato spotted wilt virus (TSWV), the viral nucleocapsid protein (NP) and the movement protein (MP) gene sequences can be used, and for viruses belonging to the Alpha-like supergroup of viruses such as TMV and CMV, RNA-dependent RNA-polymerase (RdRpu) and movement protein (MP) gene sequences can be used. For viruses belonging to the Picomalike supergroup of viruses, including potyviruses, any viral sequence may be linked to the promoters of the invention. Finally, for all other viruses, including DNA viruses, RNA-dependent RNA-polymerase (RdRp) or replicase-associated gene sequences may be used. Such constructs for virus control can be constructed as exemplified in Example 8 and Example 9 of WO 00/68374. It is within the ordinary skill of the person skilled in the art to replace the promoters disclosed in WO 00/68374 with the promoters of the present invention. Following the teaching of WO 00/68374 the skilled artisan also knows how to prepare constructs comprising the promoters of the invention operably linked to a viral sequences as mentioned hereinbefore to confer resistance or tolerance to said virus.

Instead of expressing double stranded viral RNA in transgenic plants, as disclosed in WO 00/68374, the viral RNA can also be expressed as a non-translatable RNA plus-sense viral RNA molecule as described, for example, in U.S. Pat. No. 558,302 or in Examples 12 and 13 of the present invention.

It is a further objective of the invention to provide recombinant expression vectors comprising a DNA sequence of the invention fused to an associated nucleotide sequence of interest. In these vectors, foreign DNA can be inserted into a polylinker region such that these exogenous sequences can be expressed in a suited host cell which may be, for example, of bacterial or plant origin. For example, the plasmid pBI101 derived from the *Agrobacterium tumefaciens* binary vector pBIN19 allows cloning and testing of promoters using beta-glucuronidase (GUS) expression signal (Jefferson et al, 1987, EMBO J. 6: 3901–3907). The size of the vector is 12.2 kb. It has a low-copy RK2 origin of replication and confers kanamycine resistance in both bacteria and plants. There are numerous other expression vectors known to the person skilled in the art that can be used according to the invention.

It is a further objective of the present invention to provide transgenic plants comprising the recombinant DNA sequences of the invention. The invention thus relates to plant cells, to plants derived from such cells, to plant material, to the progeny and to seeds derived from such plants, and to agricultural products with improved properties obtained by any one of the transformation methods described below. Plants transformed in accordance with the present invention may be monocots or dicots and include, but are not limited to, rice, maize, wheat, barley, rye, sweet potato, sweet corn, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugar-beet, sunflower, rapeseed, clover, tobacco, carrot, cotton, alfalfa, potato, eggplant, cucumber, *Arabidopsis thaliana*, and woody plants such as coniferous and deciduous trees. Preferred plants to be transformed are rice, maize, wheat, barley, cabbage, cauliflower, pepper, squash, melon, soybean, tomato, sugar-beet, sunflower or cotton, but especially rice, maize, wheat, *Sorghum bicolor*, orchardgrass, sugar beet and soybean. The recombinant DNA sequences of the invention can be introduced into the plant cell by a number of well-known methods. Those skilled in the art will appreciate that the choice of such method might depend on the type of plant which is targeted for transformation, i.e., monocot or dicot. Suitable methods of transforming plant cells include microinjection (Crossway et al., 1986, Bio Techniques 4:320–334), electroporation (Riggs and Bates, 1986, Proc.

Natl. Acad. Sci., USA 83:5602–5606), *Agrobacterium*-mediated transformation (Hinchee et al., 1988, Bio/Technology 6:915–922; EP 0 853 675), direct gene transfer (Paszkowski et al., 1984, EMBO J. 3:2717–2722), and ballistic particle acceleration using devices available from Agracetus, Inc., Madison, Wis. and Dupont, Inc., Wilmington, Del. (see, for example, U.S. Pat. No. 4,945,050 and McCabe et al., 1988, Bio/Technology 6:923–926). The cells to be transformed may be differentiated leaf cells, embryogenic cells, or any other type of cell. In the direct transformation of protoplasts, the uptake of exogenous genetic material into a protoplast may be enhanced by the use of a chemical agent or an electric field. The exogenous material may then be integrated into the nuclear genome. The previous work is conducted in dicot tobacco plants, which resulted in the foreign DNA being incorporated and transferred to progeny plants (Paszkowski et al., 1984, EMBO J. 3:2712–2722; Potrykus et al., 1985, Mol. Gen. Genet 199:169–177). Monocot protoplasts, for example, of *Triticum monococcum*, *Lolium multiflorum* (Italian rye grass), maize, and Black Mexican sweet corn, are transformed by this procedure. An additional preferred embodiment is the protoplast transformation method for maize as disclosed in EP 0 292 435, as well as in EP 0 846 771. For maize transformation also see Koziel et al., 1993, Bio/Technology 11:194–200.

Transformation of rice can be carried out by direct gene transfer techniques utilizing protoplasts or particle bombardment. Protoplast-mediated transformation is described for Japonica-types and Indica-types (Zhang et al., 1988, Plant Cell Rep., 7:379–384; Shimamoto et al., 1989, Nature 338:274–276; Datta et al., 1990, Bio/Technology 8:736–740). Both types described above are also routinely transformable using particle bombardment (Christou et al., 1991, Bio/Technology 9:957–962). Patent application No. EP 0 332 581 describes techniques for the generation, transformation and regeneration of Pooideae protoplasts. These techniques allow the transformation of all Pooideae plants including Dactylis and wheat. Furthermore, wheat transformation is described in patent application No. EP 0 674 715; and by Weeks et al., 1993 (Plant Physiol. 102: 1077–1084).

The thus-constructed plant expression vector can, for example, be introduced into the calli of rice according to the conventional plant transformation method, and the differentiation of roots and leaves is induced therefrom, and then, can be transferred to a flowerpot for cultivation, thereby obtaining the transformed rice.

The plants resulting from transformation with the DNA sequences or vectors of the present invention will express a nucleotide sequence of interest throughout the plant and in most tissues and organs.

The genetic properties engineered into the transgenic plants described above are passed on by sexual reproduction or vegetative growth and can thus be maintained and propagated in progeny plants. Generally said maintenance and propagation make use of known agricultural methods developed to fit specific purposes such as tilling, sowing or harvesting.

Specialized processes such as hydroponics or greenhouse technologies can also be applied. Use of the advantageous genetic properties of the transgenic plants according to the invention can further be made in plant breeding that aims at the development of plants with improved properties such as tolerance of pests, herbicides, or stress, improved nutritional value, increased yield, or improved structure causing less loss from lodging or shattering. The various breeding steps are characterized by well-defined human intervention such as selecting the lines to be crossed, directing pollination of the parental lines, or selecting appropriate progeny plants. Depending on the desired properties different breeding measures are taken. The relevant techniques are well known in the art and include but are not limited to hybridization, inbreeding, backcross breeding, multiline breeding, variety blend, interspecific hybridization, aneuploid techniques, etc. Hybridization techniques also include the sterilization of plants to yield male or female sterile plants by mechanical, chemical or biochemical means. Cross pollination of a male sterile plant with pollen of a different line assures that the genome of the male sterile but female fertile plant will uniformly obtain properties of both parental lines. Thus, the transgenic plants according to the invention can be used for the breeding of improved plant lines that for example increase the effectiveness of conventional methods such as herbicide or pesticide treatment or allow to dispense with said methods due to their modified genetic properties. Alternatively new crops with improved stress tolerance can be obtained that, due to their optimized genetic "equipment", yield harvested product of better quality than products that were not able to tolerate comparable adverse developmental conditions.

It is another objective of the present invention to provide DNA sequences that can be used to express a nucleotide sequence of interest in a desired organism. This organism can be a bacterium, a plant or any other organism of interest.

Furthermore, the disclosure of SEQ ID NOs:1 to 6 enables a person skilled in the art to design oligonucleotides for polymerase chain reactions which attempt to amplify DNA fragments from templates comprising a sequence of nucleotides characterized by any continuous sequence of 15 and preferably 20 to 30 or more base pairs in SEQ ID Nos:1, 2, 3, 4, 5 or 6. Said nucleotides comprise a sequence of nucleotides which represents 15 and preferably 20 to 30 or more base pairs of SEQ ID Nos:1, 2, 3, 4, 5 or 6. Polymerase chain reactions performed using at least one such oligonucleotide and their amplification products constitute another embodiment of the present invention.

BRIEF DESCRIPTION OF THE SEQUENCES IN THE SEQUENCE LISTING

| | |
|---|---|
| SEQ ID NO:1 | CmpD |
| SEQ ID NO:2 | CmpC |
| SEQ ID NO:3 | CmpS |
| SEQ ID NO:4 | CmpL |
| SEQ ID NO:5 | CmpB |
| SEQ ID NO:6 | CmpA |
| SEQ ID NO:7 | S1 forward primer |
| SEQ ID NO:8 | S2 reverse primer |
| SEQ ID NO:9 | GUS forward primer |
| SEQ ID NO:10 | GUS reverse primer |
| SEQ ID NO:11 | CAT forward primer |
| SEQ ID NO:12 | CAT reverse primer |
| SEQ ID NO:13 | Cmp1 forward primer |
| SEQ ID NO:14 | CmpC2 reverse primer |
| SEQ ID NO:15 | CmpS2 reverse primer |
| SEQ ID NO:16 | CmpL2 reverse primer |
| SEQ ID NO:17 | PA forward primer |
| SEQ ID NO:18 | PA reverse primer |
| SEQ ID NO:19 | CmpE |
| SEQ ID NO:20 | CmpF |
| SEQ ID NO:21 | NOS terminator forward primer |
| SEQ ID NO:22 | NOS terminator reverse primer |
| SEQ ID NO:23 | TSWV NP gene forward primer |
| SEQ ID NO:24 | TSWV NP gene reverse primer |
| SEQ ID NO:25 | CmYLCV promoter forward primer |

-continued

| | |
|---|---|
| SEQ ID NO:26 | CmYLCV promoter reverse primer |
| SEQ ID NO:27 | AGLINK multicloning site |
| SEQ ID NO:28 | BIGLINK multicloning site |
| SEQ ID NO:29 | Cmpf-B primer |
| SEQ ID NO:30 | CmpS-B primer |
| SEQ ID NO:31 | pNOV2804; binary vector, contains a promoterless PMI-nos terminator expression cassette |
| SEQ ID NO:32 | pNOV3604; vector for transformation by biolistics, contains a promoterless PMI-nos terminator expression cassette |
| SEQ ID NO:33 | CmpMr reverse primer |
| SEQ ID NO:34 | CmpMf forward primer |
| SEQ ID NO:35 | CmpMrs reverse primer |
| SEQ ID NO:36 | CmpMfs forward primer |
| SEQ ID NO:37 | synGFPI; plant optimized GFP gene with intron |
| SEQ ID NO:38 | GIG; GUS gene with intron |
| SEQ ID NO:39 | Cmp-C reverse primer |
| SEQ ID NO:40 | CmpS-synGFPI-nos expression cassette |
| SEQ ID NO:41 | CmpS-GIG-nos expression cassette |
| SEQ ID NO:42 | CmpC-synGFPI-nos expression cassette |
| SEQ ID NO:43 | CmpC-GIG-nos expression cassette |
| SEQ ID NO:44 | pNOV2117 vector |
| SEQ ID NO:45 | pNOV4200 vector |
| SEQ ID NO:46 | ZmUbi-GFP-35S term expression cassette |
| SEQ ID NO:47 | ZmUbi-GIG-nos expression cassette |
| SEQ ID NO:48 | Ubq3(At)-synGFPI-nos expression cassette |
| SEQ ID NO:49 | Ubq3(At)-GIG-nos expression cassette |

EXAMPLES

Standard recombinant DNA and molecular cloning techniques used here are well known in the art and are described, for example, by Sambrook et al., 1989, *"Molecular Cloning"*, Cold Spring Harbor, Cold Spring Harbor Laboratory Press, NY and by Ausubel et al., 1994, "Current protocols in molecular biology", John Wiley and Sons, New York.

Example 1

Virus Cloning

1. DNA extraction Virus genomic DNA is extracted from Cestrum yellow leaf curling virus-infected *Cestrum parqui* plants. Five grams of infected leaves are homogenized in 30 ml of grinding buffer (0.2 M Tris pH 7.0, 0.02 M EDTA, 2 M Urea) for 60 sec at maximum speed in a Brinkman Polytron homogenizer with PT10 probe and gently shaken at 4° C. overnight with Triton X-100 (2% final concentration). Virus is purified from crude homogenate by low-speed centrifugation (10,000 rpm for 20 min in a Sorvall SS-34 rotor) and from the obtained supernatant by high-speed centrifugation (27,000 rpm for 2 hr in a Beckman SW-28 rotor) through a sucrose cushion (3 ml of 15% sucrose). The pellet-containing virus is then resuspended in 0.1 M Tris, pH 7.4, 2.5 mM MgCl$_2$. DNase I (Sigma) and RNase A (Sigma) are added to a concentration of 10 mg/ml each. After 30 min at 37° C., the reaction is stopped with the addition of EDTA to 10 mM. Virus DNA is isolated from CmYLCV particles by treating with protease K (E. Merck, 0.5 mg/ml final concentration) in the presence of 1% SDS at 65° C. for 15 min. The viral DNA is then purified by phenol extraction and by ethanol precipitation. The virus DNA contained in the final ethanol precipitate is dissolved in water.

2. DNA amplification and cloning Hundred nanograms of the obtained DNA are used as a template for PCR amplification in a 50 µl reaction volume containing 10 µM of each primer, 25 mM each dNTP, 5 µl of pfu reaction buffer (Stratagene) and 2.5 units of pfu turbo DNA polymerase (Stratagene). A S1 forward primer (gaccacaaacatcagaag, SEQ ID NO:7) and a S2 reverse primer (caaacttattgggtaatc, SEQ ID NO:8) are used for the PCR reaction. Cycling parameters for PCR are: 1×(94° C. for 1 min); 30×(94° C. for 1 min, 50° C. for 1 min, 72° C. for 1 min); 1×(72° C. for 10 min) Each single DNA fragment is cloned in pPCR-Script™ Amp SK(+) plasmid (Stratagene) according to the manufacturer's instructions.

Example 2

DNA Sequencing

Sequencing of the DNA virus clones is carried out using the automated ABI PRISM 377 DNA sequencer (Perkin Elmer) and ABI PRISM dRhodamine terminator cycle sequencing kit (Perkin Elmer) according to the manufacturer's instructions. The described S1 primer and S2 primers (Example 1) are used for the sequencing reactions as well as the universal M13–20 and Reverse primers.

Example 3

Construction of Plasmids for Transient Expression

All the PCR reactions are carried out with Pfu polymerase (Stratagene) as described in Example 1.

1. Reporter genes amplification The beta-glucuronidase (GUS) and the chloramphenicol acetyltransferase (CAT) reporter genes are amplified. For GUS gene amplification GUS forward (cagggtaccactaaaatcacc, SEQ ID NO:9) and GUS reverse (aggggatccccaattcccc, SEQ ID NO:10) oligonucleotides are used at the annealing temperature of 60° C. CAT forward (aggggtaccatcgatatggag, SEQ ID NO:11) and Cat reverse (ttaggatccgccctgccac, SEQ ID NO:12) oligonucleotides are annealed at 62° C. The forward primers are designed to contain a KpnI recognition site and the reverse ones a BamHI site.

2. CmYLCV promoter amplification Three different promoter fragments are selected. CmpC (SEQ ID NO:2), CmpS (SEQ ID NO:3), and CmpL (SEQ ID NO:4). Cmp1 forward primer (cttctagacaaagtggcagac, SEQ ID NO:13) is used for all the three amplifications at the annealing temperature of 52° C. It is modified (shown in bold) from the original sequence to contain a XbaI recognition site. The CmpC2 reverse primer (ttggtaccttaacaatgaggg, SEQ ID NO:14) is used for CmpC fragment amplification and the CmpS2 reverse primer (ctacttctaggtaccttgctc, SEQ ID NO:15) is used for the CmpS fragment. Both of them are modified to contain a KpnI recognition site. The CmpL2 reverse primer (ttggtaccttaacaatgaggg, SEQ ID NO:16) is used for CmpL fragment amplification and it is modified to contain a ClaI restriction site.

3. Polyadenylation signal amplification The polyadenylation signal fragments is amplified from the cauliflower mosaic virus (CaMV) infectious clone (Franck et al., Cell 21 (1), 285–294, 1980). PA (polyadenylation signal amplification) forward (ggggatccccagtctctctc, SEQ ID NO:17) and PA reverse (gtgaattcgagctcggta, SEQ ID NO:18) oligonucleotides are used for PCR and annealed at 60° C. The forward primer is designed to contain a BamHI recognition site and the reverse one an EcoRI site.

4. Produced Constructs pCmpCG (CmpC promoter fragment+GUS gene+polyA)
pCmpSG (CmpS promoter fragment+GUS gene+polyA)
pCmpCC (CmpC promoter fragment+CAT gene+polyA)
pCmpSC (CmpS promoter fragment+CAT gene+polyA)
pCmpLC (CmpL promoter fragment+CAT gene+polyA)

The cassettes containing the promoter fragment, the reporter genes and the polyadenylation signal are inserted in a pUC19 vector (Stratagene) restricted with XbaI and EcoRI.

5. Constructs Used for Comparison pCapG (Cap promoter fragment+GUS gene+polyA)
pCapSG (CapS promoter fragment+GUS gene+polyA)
pCapC (Cap promoter fragment+CAT gene+polyA)

Promoter fragments contained in these constructs are obtained from CaMV (Franck et al., Cell 21 (1), 285–294, 1980, see GenBank accession number V00141). GUS, CAT and polyA fragments are identical to those used for the CmYLCV constructs. Cap corresponds to the fragment from base −227 to base +33 from TATA-box (base 7175 to base 7438 of the CaMV genome, see GenBank accession number V00141) and CapS corresponds to the fragment from base −227 to base +82 from TATA-box (base 7175 to base 7486 of the CaMV genome, see GenBank accession number V00141). These positions correspond approximately to those chosen for the CmYLCV fragments.

Example 4

Transient Expression Experiments

1. Suspension Cultures and Protoplast Preparation

*Orychophragmus violaceus.* Suspension cultures are maintained in 40 ml of MS medium (Murashige and Skoog, Physiol Plant 15, 474–497, 1962) including 100 mg/ml inositol, 2% sucrose, and 0.1 mg/ml 2,4D. Protoplasts are isolated from 4- to 5-day-old-cultures. Cell walls are digested at 26° C. for 1 hr in 0.1% pectolyaseu Y23 (Seishin Pharmaceutical Co., Japan), 1% cellulase Onozuka R10 (Yakult Honsha Co., Japan), 0.4 M D-mannitol, and 0.1% MES, pH 5.5. Protoplasts are filtered through a 50 µm sieve and washed twice with electroporation (EP) solution (10 mM HEPES, 150 mM NaCl, 5 mM $CaCl_2$, 0.2 M mannitol, pH 7.1).

*Nicotiana plumbaginifolia.* Plants are maintained axenically on RPM2 medium (Blonstein et al., Mol Gen Genet 211, 252–259, 1988) plus 7 g/l bacto agar, pH 5.6. For protoplasts preparation, leaves are cut and incubated overnight at 26° C. in a solution of 0.5% driselase (Fluka), 0.25 mM PVP 10 (polyvinylpyrrolidone MW 10000), 3.85 mM $CaCl_2$, 6 mg/l NAA, 2 mg/l BAP, and 0.5 M sucrose, pH 5.7. Protoplasts are filtered through a 100 µm sieve. Sucrose solution (0.6 M sucrose, 0.1% MES, and 15 mM $CaCl_2$, pH 5.7) is added to the protoplast suspension for the first purification step, and the suspension is overlaid with W5 solution (150 mM NaCl, 125 mM $CaCl_2$, 5 mM KCl, 6 mM glucose; Menczel et al., Theor Appl Genet 59, 191–195, 1981). Protoplasts are then washed once with W5 solution and finally with EP solution.

*Oryza sativa.* Protoplasts are prepared from a morphogenic rice suspension culture established from *O. sativa* cv. Nipponbare as described (Datta et al., 1990, Bio/Technology 8:736–740).

2. Transient expression experiment Transfection by electroporation of $2\times10^6$ *Orychophragmus violaceus* protoplasts in 0.66 ml EP buffer is carried out by discharging a 960 µF capacitor through a distance of 4 mm of protoplast suspension. The capacitor is loaded at the 450 Volts. Electroporation is performed in the presence of 5–10 µg of plasmid DNA, then protoplasts are cultivated 16 to 24 hours at 25° C. Transfection of $2\times10^6$ *Nicotiana plumbaginifolia* protoplast in 0.3 ml suspension is carried out in the presence of 0.3 ml PEG (40% polyetyleneglycole 6000) and 5–10 µg of plasmid DNA. Protoplasts are cultivated in 0.4 ml K3 medium (Godall et al., Methods Enzymol 181, 148–161, 1990) for 16 to 24 hours at 25° C. and added with 10 ml W5 buffer before harvesting.

Protein extracts are prepared by at least three cycles of freezing and thawing, and clarified by centrifugation.

Example 5

CAT and GUS Assays

For detection of CAT gene expression double antibody sandwich (DAS)-ELISA is carried out using a CAT ELISA kit (Boehringer) according to the manufacturer's instructions. CAT activity is measured with a Dynex MRXII apparatus. Samples for GUS assay are diluted in GUS buffer (0.05 M $NaPO_4$, pH 7, 0.01 M EDTA, 0.1% Triton-X-100, 0.1% Sarkosyl). The reaction is carried out in the presence of an equal amount of GUS-reaction buffer (100 ml/l 10×GUS buffer, 200 mg/l BSA, 705 mg/l 4-methylumbelliferyl-glucuronide) at 37° C. and stopped with 2 M Ammediol. The activity is measured in a Titertek Fluroskan II.

Both CAT and GUS assay results are normalized to a standard clone value. Results obtained from ten different experiments show that the various CmYLCV promoter fragments function as highly active promoters.

*N. plumbaginifolia* Protoplast Transient Expression

| | GUS reporter gene | |
|---|---|---|
| CmpCG | 100 | |
| CmpSG | 86.9 | +/−20% |
| CapG | 9 | +/−20% |
| CapSG | 38.9 | +/−15% |
| | CAT reporter gene | |
| CmpCC | 100 | |
| CmpSC | 78 | /−20% |
| CapSC | 89.5 | +/−15% |
| CmpLC | 9 | +/−20% |

*O. violaceus* Protoplast Transient Expression

| | GUS reporter gene | |
|---|---|---|
| CmpCG | 100 | |
| CmpSG | 84.6 | +/−15% |
| CapG | 9.6 | +/−15% |
| CapSG | 40.7 | +/−15% |
| | CAT reporter gene | |
| CmpCC | 100 | |
| CmpSC | 255 | +/−20% |
| CapSC | 546 | +/−15% |
| CmpLC | 10 | +/−20% |

*O. sativa* Protoplast Transient Expression

| | GUS reporter gene | |
|---|---|---|
| CmpCG | 100 | |
| CmpSG | 84.6 | +/−15% |
| CapG | 9.6 | +/−15% |
| CapSG | 40.7 | +/−15% |

Example 6

Preparation of Solutions and Media for Plant Regeneration and Transformation Culture media GM, CIM and SIM are the media described by Valvekens et al. (1988, Proc. Natl. Acad. Sci. USA. 85: 5536–5540).

Culture medium GM contains the mineral salts of Murashige and Skoog (1962, Physiol. Plant. 15:473–497), 1.0 mg/l thiamine (stock 1 mg/ml), 0.5 mg/l pyridoxine HCl (stock 1 mg/ml), 0.5 mg/[nicotinic acid (stock 1 mg/ml), 0.5 g/l 2-(N-morpholino)ethanesulfonic acid (MES), 10 g/l sucrose, 8 g/l agar, with the pH adjusted to 5.8 with 1N KOH. CIM contains the mineral salts and vitamins of B5 medium (Gamborg et al., 1968, Exp. Cell Res. 50:151–158), 0.5 g/l 2-(N-morpholino)ethanesulfonic acid (MES), 20 g/l glucose, 0.5 mg/l 2,4-dichlorophenoxyacetic acid (2,4-D) (stock 10 mg/ml in DMSO), 0.05 mg/l kinetin (stock 5 mg/ml in DMSO), pH 5.8. Solid CIM medium contains 8 g/l agar. SIM contains the mineral salts and vitamins of B5 medium (Gamborg et al., 1968, supra), 0.5 g/l 2-(N-morpholino)ethanesulfonic acid (MES), 20 g/l glucose, 5 mg/l N6-(2-isopentenyl)adenine (2iP) (stock 20 mg/ml in DMSO), 0.15 mg/l indole-3-acetic-acid (IAA) (stock 1.5 mg/ml in DMSO), 8 g/l agar, pH 5.8. SIM V750 K100 is SIM medium supplemented with 750 mg/l vancomycin and 100 mg/l kanamycin. SIM V500 K100 is SIM medium supplemented with 500 mg/l vancomycin and 100 mg/l kanamycin. GM K50 is GM medium supplemented with 50 mg/l kanamycin.

The culture media are all sterilized by autoclaving (20 min, 121° C.). Vitamins are dissolved in water and added to media before autoclaving. Hormones are dissolved in dimethyl sulfoxide (DMSO). Antibiotics are dissolved in water and sterilized by filtration (0.22 µm). Hormones and antibiotics are added after autoclaving and cooling of the media to 65° C. In all cases 9-cm Petri dishes (Falcon, 3003) are used, except for GM and GM K50 which are usually poured into 15-cm Petri dishes (Falcon, 3025).

Plates with solid media are dried before usage in laminar flow to remove condensate.

Example 7

Arabidopsis strain and Growth Conditions

*Arabidopsis thaliana* seeds ecotype Columbia (Col-0) wild type are purchased from Lehle Seeds, USA (1102 South Industrial Blvd. Suite D, Round Rock Tex. 78681, USA). Plants are grown at 22° C. 16/8 hour light/dark cycle in pots in the mixture of 4 parts sand, 4 parts garden soil and 1 part agrilit.

Example 8

Agrobacterium Strain and Culture

Vector plasmids are introduced into recipient *Agrobacterium tumefaciens* strain LBA4404 (Clontech) by triparental mating according to the protocol described by Walkerpeach and Velten ("*Agrobacterium*-mediated gene transfer to plant cells: Cointegrate and binary vector systems". in: Plant Molecular Biology Manual, B1: 1–19,1994. Eds.: S. B. Gelvin, R. A., Schilperoort, Kluvers Acad. Publishers.). Mobilizing strain used is *E. coli* HB101 harboring conjugation plasmid pRK2013 (Ditta et al., 1980, Broad host range DNA cloning system from Gram-negative bacteria. Construction of gene bank of *Rhizobium meliloti*. Proc. Natl. Acad. Sci. USA 77: 7347–7351). *Agrobacteria* used for root transformation are grown in LB medium (Sambrook et al., 1989, "Molecular Cloning", Cold Spring Harbor, Cold Spring Harbor Laboratory Press, NY) without antibiotics at 28° C. and 200 rpm.

Example 9

Seed Sterilization

Seeds are placed in 70% EtOH/0.05% Tween 20 for 1 minute in a 2 ml Eppendorf tube. 70% EtOH/0.05% Tween 20 is removed with a pipette and replaced with 5% NaOCl/ 0.05% Tween 20 for 15 minutes. Seeds are shaken regularly. The solution is removed in sterile conditions and the seeds are washed in sterile, distilled water 3 times for 10 minutes each. After the last wash seeds are keep in 0.5–1 ml water. Seeds can be used immediately or stored at 4° C. for two-three weeks. Sterilized seeds (20–30) are transferred with forceps on GM medium in 15-cm Petri dishes. Seedlings are grown in vertically placed plates in a growth chamber (22° C.; 16/8 hour light/dark cycle).

Example 10

Transformation of Root Explants of *Arabidopsis thaliana*

Roots of three-week-old seedlings are used in the transformation procedure. Roots should not be green or brown. Green parts of seedlings are removed with scalpel and forceps. Remaining roots are collected and approximately 5 entire root systems are placed per plate with solid CIM medium. Roots are pressed gently onto the surface of the plate to ensure full contact with the medium, but they should not be dipped into the agar. Roots are incubated for three days in a growth chamber (22° C.; 16/8 hour light/dark cycle). Roots are then transferred to a sterile Petri dish with filter paper wetted with liquid CIM medium and cut with a scalpel in 0.5–1 cm pieces. Root explants are then transferred to a 50 ml sterile Falcon tube containing 10 ml of liquid CIM medium. To this, 0.5 ml of an overnight *Agrobacterium* culture (OD 0.6–1) is added and incubate for 1–2 minutes while shaking gently. The liquid is poured out of the tube through sterile metal screens (50 mesh, Sigma, S-0895), which are kept with forceps. Roots usually remain on the wall of the tube close to its edge. Then the root explants are transferred to a sterile Petri dish with filter paper and briefly blotted dry to remove excess of liquid. Root explants are put onto plates with solid CIM medium and incubated in a growth chamber for 2 days under dim light (1.5–2 klux). Slight traces of overgrowth with *Agrobacterium* should be visible after the period of cocultivation. Root explants are then transferred to sterile 50 ml Falcon tubes with 20 ml of liquid CIM medium, supplemented with 1000 mg/l vancomycin. The Falcon tubes are then gently vortexed to remove the *Agrobacteria*. The liquid is poured out of the tube as described above and the explants are briefly blotted dry on filter paper. Explants are then transferred to plates containing SIM V750 K100 medium. Roots should be in a close contact with the medium. The explants are incubated in a growth chamber in normal conditions for one week and then transferred to SIM V500 K100 medium and incubated for an additional week. Then the amount of vancomycin is reduced to 250 mg/l. First shoots should appear at the end of the third week of cultivation on SIM media. Shoots are excised when 0.3–0.5-cm long, any residual callus is removed, and the shoots are transferred to 15-cm plates containing GM K50 medium. Max. 3 shoots are placed per plate. To get more shoots, the remaining root explants can be transferred to fresh SIM plates supplemented with 125 mg/l vancomycin and 100 mg/l kanamycin for additional two weeks. Rooted shoots can be transferred to soil to allow seed set. Shoots that do not root are transferred to Magenta jars (one per jar) containing GM medium to produce seeds in vitro.

Seeds from individual transgenic plants are germinated on GM K50 medium in growth chamber for 2 weeks. Phenotypically normal kanamycin resistant seedlings, which form green true leaves and branched root system, are selected for further analyses.

Example 11

Histochemical β-glucuronidase (GUS) Assay

In vitro grown seedlings or plants grown in soil are used in GUS assays. Either whole seedlings or dissected organs are dipped into GUS staining solution. GUS staining solution contains 1 mM 5-bromo-4-chloro-3-indolyl glucuronide (X-Gluc, Duchefa, 20 mM stock in DMSO), 100 mM Na-phosphate buffer pH 7.0, 10 mM EDTA pH 8.0, and 0.1% Triton X100. Tissue samples are incubated at 37° C. for 1–16 hours. If necessary samples can be cleared with several washes of 70% EtOH to remove chlorophyll.

Example 12

Construction of Tobacco Transformation Vector pZU627

All the PCR reactions are carried out with Platinum Pfx DNA Polymerase (Life Technologies) according to manufacturer's instructions.

1. NOS Terminator Amplification and Cloning

The NOS terminator is amplified from pBIN19 (Bevan et al 1984) using the NOS terminator forward primer (SEQ ID NO:21) and NOS terminator reverse primer (SEQ ID NO:22). The forward primer is modified to contain a PstI site and the reverse primer is modified to contain a HindIII site. The NOS terminator amplification product is cloned as PstI/HindIII fragment in same sites of pBluescript (Stratagene) resulting in plasmid pZU400A.

2. Amplification of the Tomato Spotted Wilt Virus Nucleocapsid Protein (TSWV NP) Gene Amplification and Cloning In order to obtain a non-translatable TSWV NP gene, modified TSWV NP gene primers are used to amplify the TSWV NP gene. The TSWV NP gene forward primer introduces a BamHI, a SphI, a start and a stop codon (SEQ ID NO:23). The reverse primer is modified to introduce a PstI site (SEQ ID NO:24). The amplification product is cloned as BamHI/PstI fragment into the BamHI/PstI site of pZU400A upstream of and in same direction as the NOS terminator. In the resulting clone pZU400b the PstI site between the TSWV NP gene and the NOS terminator is removed using a T4 DNA polymerase treatment (Life Technologies) according to manufacturer's instructions. From the resulting clone denoted pZU400C, the TSWV NP gene and NOS terminator are cloned as a SphI/HindIII fragment into the SphI/HindIII site of shuttle vector pZO1560 resulting in plasmid pZU400. pZO1560 is a pBluescript derivative in which the original multicloning site is replaced by the AGLINK multicloning site (SEQ ID NO:27).

3. CmYLCV Promoter Amplification and Cloning

The CmYLCV viral promoter is amplified using CmYLCV promoter forward primer (SEQ ID NO:25) and CmYLCV promoter reverse primer (SEQ ID NO:26). The forward primer is modified to contain a SstI site and the reverse primer is modified to contain a PstI site. The amplified CmYLCV viral promoter is cloned as SstI/PstI fragment, in same direction as and upstream of the TSWV-N gene, into the SstI/PstI site of pZU400. This results in clone pZU625 that contains a viral gene cassette that produces a non-translatable TSWV NP RNA.

4. Cloning of Viral Gene Cassette to pVictorHiNK

The viral gene cassette is cloned as AscI/PacI fragment from pZU625 into the AscI/PacI site of pVictorHiNK vector pZU494. This results in the plant transformation vector pZU627. pVictorHiNK is a binary vector comprising an origin of replication (ORI) derived from *Pseudomonas aeruginosa* plasmid pVS1 which is known to be highly stable in *A. tumefaciens* (Itoh et al., 1984. Plasmid 11:206–220; Itoh and Haas, 1985. Gene 36;27–36). The pVS1 ORI is only functional in *Agrobacterium* and can be mobilized by the helper plasmid pRK2013 from *E. coli* into *A. tumefaciens* by means of a triparental mating procedure (Ditta et al., 1980. Proc. Natl. Acad. Sci. USA 77:7347–7351).

This binary vector also comprises a ColEI origin of replication which is functional in *E. coli* and derived from pUC19 (Yannisch-Perron et al., 1985. Gene 33:103–119).

For maintenance in *Ecoli* and *A. tumefaciens* this vector contains a bacterial resistance gene to spectomycin and streptomycin encoded by a 0.93 kb gene from transposon Tn7 (Fling et al., 1985. Nucl. Acid Res. 13:7095) which functions as selection marker for maintenance of the vector in *E. coli* and *A. tumefaciens*. The gene is fused to the tac promoter for efficient bacterial expression (Amman et al., 1983. Gene 25: 167–178).

The right and left T-DNA border fragments of 1.9 kb and 0.9 kb, respectively that comprise the 24 bp border repeats, are derived from the Ti-plasmid of the nopaline type *A. tumefaciens* strains pTil37 (Yadev et al., 1982. Proc. Natl. Acad. Sci. USA. 79:6322–6326). Subsequently the T-DNA region between the borders is modified by deleting the M13 derived sequences and, to improve its cloning versatility, the BIGLINK multicloning site (SEQ ID NO:28) is introduced yielding pVictorHiNK.

PVictorHiNK contains an NPTII gene cassette for selection of transformants during the plant transformation process. This gene cassette contains a NOS promoter, the NPTII gene and the NOS terminator, obtained from *A. tumefaciens*.

Example 13

Plant Transformation and Screening for Resistance

1. Transformation of Binary Vectors to Plant Material

Methods to transfer binary vectors to plant material are well established and known to a person skilled in the art. Variations in procedures exist due to for instance differences in used *Agrobacterium* strains, different sources of explant material, differences in regeneration systems depending on as well the cultivar as the plant species used. Binary vector pZU627 is used in plant transformation experiments according to the following procedures. PZU627 is transferred by tri-parental mating to an acceptor *Agrobacterium tumefaciens* strain, followed by Southern blot analysis of the ex-conjugants for verification of proper transfer of the construct to the acceptor strain, inoculation and co-cultivation of axenic explant material with the recombinant *Agrobacterium tumefaciens* strain, selective killing of the *Agrobacterium tumefaciens* strain using the appropriate antibiotics, selection of transformed cells by growing on selective media containing kanamycine, transfer of plantlets to soil, assaying for the intactness of the integrated T-DNA by Southern blot analysis of isolated chromosomal DNA of the plant.

2. Resistance of Plants Against TSWV Infections

Transformed plants are grown in the greenhouse under standard quarantine conditions in order to prevent any infection by pathogens. At a four-leaf stage the plants are infected with TSWV by mechanical inoculation. Tissue from plants systemically infected with TSWV is ground in 5 volumes of ice-cold inoculation buffer (10 mM phosphate buffer supplemented with 1% $Na_2SO_3$) and rubbed in the presence of carborundum powder on the first two fully extended new leaves. The inoculated plants are monitored for symptom development during three weeks after inoculation. Plants containing pZU627 sequences do not show TSWV symptoms, whereas untransformed control plants show severe systemic TSWV symptoms within 7 days after inoculation. Resistant plants are self-pollinated and the seeds harvested. Progeny plants are analyzed for segregation of the inserted gene and subsequently re-screened for resistance against TSWV infection as described above.

Example 14

Construction of CmpS-phosphomannose Isomerase-nos Constructs for Plant Transformation The CmpS promoter is PCR amplified using the Cmpf-B (cgc gga tcc tgg cag aca aag tgg cag a; SEQ ID NO:29) and the CmpS-B (cgc gga tcc tac ttc tag gct act tg, SEQ ID NO:30) primers having flanking BamHI sites. The resulting PCR fragment is cloned into the BamHI site of pBluescript KS (+) to form pNOV4211.

To create a binary vector for transformation via *Agrobacterium tumefaciens*, the CmpS promoter is excised from pNOV4211 using BamHI and inserted into BamHI-digested pNOV2804 (SEQ ID NO:31) upstream of the PMI gene, and the resulting vector called pNOV2819. pNOV2804 (SEQ ID NO:31) is a binary vector with VS1 origin of replication, a copy of the *Agrobacterium* virG gene in the backbone, and a promoterless PMI-nos terminator expression cassette between the left and right borders of T-DNA. PMI (phosphomannose isomerase) is the coding region of the *E. coli* manA gene (Joersbo and Okkels, 1996, Plant Cell Reports 16:219–221, Negrotto et al., 2000, Plant Cell Reports 19:798–803). The nos (nopaline synthase) terminator is obtained from *Agrobacterium tumefaciens* T-DNA (Depicker et al., 1982, J. Mol. Appl. Genet. 1 (6), 561–573. The phosphomannose isomerase coding region and the nos terminator are located at nt 290 to nt 1465 and nt 1516 to 1789 respectively, of pNOV2804 (SEQ ID NO:31).

To create a vector for biolistic transformation, the CmpS promoter is excised from pNOV4211 using BamHI and inserted into BamHI-digested pNOV3604 (SEQ ID NO:32) to form pNOV2820, thus creating a PMI expression cassette driven by the CmpS promoter. pNOV3604 is a vector for preparing biolistic fragments and is based on pUC19 with an ColEI origin of replication and a beta-lactamase gene conferring ampicillin-resistance. As pNOV2804, pNOV3604 also contains a promoterless PMI-nos terminator expression cassette (see above). The phosphomannose isomerase coding region and the nos terminator are located at nt 42 to nt 1217 and nt 1268 to 1541 respectively, of pNOV3604 (SEQ ID NO:32).

Binary vector pNOV2819 is used for transformation via *Agrobacterium tumefaciens* and vector pNOV2820 is used for biolistic transformation.

Example 15

Construction of CmpC-GUS Plasmids for Stable Expression in Planta.

1. Construction of the Binary Vector

The vector pCambia 1302 (Cambia, Canberra, Australia; Roberts, C. S., Rajagopal, S., Smith, L., Nguyen, T., Yang, W., Nugroho, S., Ravi, K. S. Cao, M. L., Vijayachandra, K., et al. A comprehensive set of modular vectors for advanced manipulation and efficient transformation of plants. Presented at the Rockefeller Foundation Meeting of the International Program on Rice Biotechnology, Malacca, Malaysia, Sep. 15–19, 1997) is chosen and modified for the experiments: The CaMV 35S promoter in front of the GFP gene is removed by digestion at position 9788 with HindIII endonuclease and at position 1 with NcoI endonuclease and the vector is relegated at the two compatible ends. Digestion with XhoI endonuclease at positions 7613 and BstXI at position 9494 excise the hygromycin gene and the CaMV 35S promoter in front of it. The 35S promoter sequences are eliminated from the vector to exclude any risk of homology-mediated gene silencing. The bar gene driven by the 1' promoter (Mengiste et al., Plant J, 1997, 12(4): 945–948) is introduced in the EcoRI site at position 9737 as a selectable marker. The obtained vector is named pCamBar.

2. Produced Constructs

The cassettes CmpCG and CapG described in Example 3 are inserted in the pCamBar vector between XbaI site at position 9764 and EcoRI at position 9737 to obtain the pCamBarCmpCG and the pCamBarCapG plasmids, respectively. The two constructs are used to transform *Agrobacterium tumefaciens* cells.

Example 16

Stable Expression in *Arabidopsis thaliana*

1. Plant Production and Transfection

*Arabidopsis thaliana* (Columbia 0) wt seeds are sown, cold-treated 3 days at 4° C. in the dark to synchronize germination and transferred to growth room (22° C./24 h light). Germinated plants are infiltrated when they have produced a maximum number of unopened buds. The infiltration is carried out according to the protocol described by Clough and Bent, Plant J. 16: 735–743, 1987.

2. Selection of Transgenic Plants

Seedlings obtained from T1-generation seeds are selected by spraying with the BASTA herbicide (Plüss-Staufer AG/SA) (150 mg/l) every five days for three times. Twenty pCamBarCmpCG and nine pCamBarCapG resistant plants are collected after selection. They are grown under the described condition to obtain the T2-generation seeds. These seeds undergo the same procedure as described above for the wt, the T2 seedlings are selected by BASTA spraying, and the resistant mutants analyzed for GUS-gene expression.

3. Histochemical GUS Expression in Stably Transformed *Arabidopsis* Plants

Histochemical GUS staining is done as described in Example 11. The analysis is performed in 15 ml culture tubes by immersion of the transformed seedlings in the X-gluc solution, application of 130 mBar pressure for 10 min and incubation at 37° C. overnight. Results obtained from *Arabidopsis* plants transformed with pCamBarCmpCG indicate a constitutive expression of the GUS reporter gene driven by the CmpC promoter in all vegetative organs.

4. Quantitative Enzymatic GUS Assays in Stably Transformed *Arabidopsis* Plants

A. Sample Preparation

Four plants per transgenic line and one leaf per each of these plants are selected for the test. The four leaves are collected in the same eppendorf tube, frozen with liquid nitrogen and ground to fine powder with disposable grinders. This is diluted in 150 µl GUS buffer (0.05M NaPO$_4$, pH 7, 0.01M EDTA, 0.1% Triton-X-100, 0.1% Sarkosyl), incubated 5 min at 37° C. and spun in a microcentrifuge for 5 min at maximum speed. The supernatant is transferred to a new eppendorf tube and these samples are used for the enzymatic test. Protein in these plant extracts is estimated according to the Bradford method (Bradford, M. M. Anal. Biochem. 72: 248–254, 1976) using BSA as a standard. The presence of the promoter and GUS gene in the mutant lines is confirmed by PCR analysis using the extracted samples as a template.

B. Fluorometric GUS Assay

The fluorometric GUS assay is done as described in Example 5. For detection of GUS gene expression samples are diluted in GUS buffer. The reaction is carried out in the presence of an equal amount of GUS-reaction buffer at 37° C. and stopped with 2 M Ammediol. The activity is measured in a Titertek Fluoroskan II.

Fifteen out of the twenty selected lines transformed with pCamBarCmpCG and eight out of nine lines transformed with pCamBarCapG show GUS enzymatic activity in leaves. The level of activity in several CmpCG transformed lines is comparable to CapG. However the results are variable for the different transgenic lines due to the difference in their genotypes (number of loci and number of transgene insertions per locus).

Example 17

Construction of CmpC Promoter Variants

All the PCR reactions are carried out with Pfu polymerase (Stratagene) as described in Example 1.

1. DNA amplification and cloning Two variants, pCmpMG and pCmpMsG, of the pCmpCG plasmid (Example 3) are produced. The former deletes the sequence "GTGGTCCC" in the CmpC promoter and the latter mutates it to the sequence "GTGCTCGC".

To obtain pCmpMG three PCR products are amplified:

CmpM1 using the Cmp1 forward primer (see Example 3, SEQ ID NO:13), the CmpMr reverse primer (CCATCGTGGTATTTGGTATTG, SEQ ID NO:33) and the pCmpCG plasmid as a template.

CmpM2 using the CmpMf forward primer (CAATACCAAATACCACGATGG; SEQ ID NO:34), the CmpC2 reverse primer (see Example 3; SEQ ID NO:14) and the pCmpCG plasmid as a template.

CmpM using the Cmp1 forward primer, the CmpC2 reverse primer and an equimolar mix of CmpM1 and CmpM2 PCR products as a template.

To obtain pCmpMsG three PCR product are amplified:

CmpMs1 using the Cmp1 forward primer, the CmpMrs reverse primer (CGTGGTAGCGAGCACTTTGGT, SEQ ID NO:35) and the pCmpCG plasmid as a template.

CmpMs2 using the CmpMfs forward primer (AAGTGCTCGCTACCACGATGG, SEQ ID NO:36), the Cmp2 reverse primer and the pCmpCG plasmid as a template.

CmpsM using the Cmp1 forward primer, the Cmp2 reverse primer and an equimolar mix of CmpMs1 and CmpMs2 PCR products as a template.

To obtain the pCmpMG and the pCmpMsG plasmids the original pCmpCG plasmid is restricted with XbaI and BamHI endonucleases to eliminate the CmpC fragment and to insert in place of it the CmpM and the CmpMs PCR products.

Example 18

Transient Expression Experiments with pCmpM and pCmpMs Constructs

1. Suspension Cultures and Protoplast Preparation

Suspension cultures and protoplasts are produced as described in Example 4.

2. GUS Assays

Transfection and protein extract preparation are carried out as described in the Example 4, and the GUS assay is carried out as described in Example 5.

GUS assay results are obtained from the average of ten different experiments and normalized to a standard clone value. The deletion of the "GTGGTCCC" sequence in the CmpCG construct reduces expression of the GUS reporter gene to about 50% of the GUS reporter gene expression from CmpC in all protoplast species (see below). The effect induced by the "GTGCTCGC" mutation depends on the plant species. In *O. violaceus* and *O. sativa* protoplasts the level of GUS gene expression is decreased to 65.2% and 73.6%, respectively. In *N. plumbaginifolia* protoplasts the CmpMs promoter activity is similar to the CmpM promoter.

| | *N. plumbaginifolia* | |
|---|---|---|
| CmpCG | 100 | |
| CmpMG | 52 | +/−12% |
| CmpMsG | 53.7 | +/−16% |
| CapG | 28.3 | +/−14% |
| | *O. violaceus* | |
| CmpCG | 100 | |
| CmpMG | 55.2 | +/−12% |
| CmpMsG | 73.6 | +/−10% |
| CapG | 5 | +/−1% |
| | *O. sativa* | |
| CmpCG | 100 | |
| CmpMG | 59.6 | +/−21% |
| CmpMsG | 65.2 | +/−20% |
| CapG | 42.5 | +/−16% |

Example 19

Construction of Plant Transformation Vectors Containing 5'-promoter Fragments Operably Linked to GFP or GUS Reporter Genes

1. Promoter Amplification and Cloning

A chimeric gene is constructed that includes a DNA sequence from the CmYLCV full-length transcript promoter (SEQ ID NO:1) fused to the plant optimized GFP with intron (synGFPI, SEQ ID NO:37) or GUS reporter gene with intron (GIG; SEQ ID NO:38) sequence. The GIG gene contains the ST-LS1 intron from *Solanum tuberosum* at nt 385 to nt 576 of SEQ ID NO: 38 (obtained from Dr. Stanton Gelvin, Purdue University, and described in Narasimhulu, et al 1996, Plant Cell, 8: 873–886.). SynGFPI is a plant optimized GFP gene into which the ST-LS1 intron is introduced (nt 278 to nt 465 of SEQ ID NO:37). For the promoters, the CmYLCV genomic DNA is used as a template for the polymerase chain reaction (PCR). Gene specific primers are designed to amplify the DNA sequence. A gene fragment corresponding to CmpC (SEQ ID NO:2) is isolated using the Cmpf-B forward primer (SEQ ID NO:29) in combination with the 5' to 3' primer CGCGGATTGCTCCCTTAACAATGAGG (SEQ ID NO:39) as reverse primer. A gene fragment corresponding to CmpS (SEQ ID NO:3) is isolated using the Cmpf-B (SEQ ID NO:29) forward primer in combination with the CmpS-B reverse primer (SEQ ID NO:30). All three primers contain the BamHI restriction enzyme recognition site CGCGGA at their 5' end. All PCR reactions are carried out with Pfu polymerase according to manufacturers recommendations (Stratagene). A thermocycler (DNA Engine, MJResearch, Inc. Waltham, Mass. USA) is used to amplify the promoter fragments using the following PCR conditions: [(94° C.:10 s):(94° C.:10 s/56° C.:30 s/72° C.:1 min)×20]: (72° C.:1.5 m)]. digestion with BamHI the promoter fragments are ligated into pUC-based vectors with the GIG gene or synGFPI gene to create the promoter-reporter gene fusions operatively linked with a nos terminator.

2. Produced Promoter-Reporter Cassettes

CmpS promoter fragment+synGFPI gene+nos (SEQ ID NO:40)
CmpS promoter fragment+GIG gene+nos (SEQ ID NO:41)
CmpC promoter fragment+synGFPI gene+nos (SEQ ID NO:42)
CmpC promoter fragment+GIG gene+nos (SEQ ID NO:43)

| SEQ ID NO | Promoter | Gene (synGFPI or GIG) | terminator |
|---|---|---|---|
| 40 | nt 1 to nt 402 | nt 411 to nt 1331 | nt 1343 to nt 1618 |
| 41 | nt 1 to nt 405 | nt 425 to nt 2425 | nt 2479 to nt 2751 |
| 42 | nt 1 to nt 354 | nt 380 to nt 1292 | nt 1304 to nt 1577 |
| 43 | nt 1 to nt 354 | nt 399 to nt 2399 | nt 2453 to nt 2725 |

3. Subcloning into *Agrobacterium* Binary Vector

The promoter-reporter cassettes (SEQ ID NO:40 to 43) containing the promoter fragment, the reporter gene and the nos terminator are inserted into binary vector pNOV2117 for maize and binary vector pNOV4200 for tomato transformation. pNOV2117 (SEQ ID NO:44) is a binary vector with VS1 origin of replication, a copy of the *Agrobacterium* virG gene in the backbone, and a Maize Ubiquitin promoter-PMI gene-nos terminator expression cassette between the left and right borders of T-DNA. PMI (phosphomannose isomerase) is the coding region of the *E. coli* manA gene (Joersbo and Okkels, 1996, Plant Cell Reports 16:219–221, Negrotto et al., 2000, Plant Cell Reports 19:798–803). The nos (nopaline synthase) terminator is obtained from *Agrobacterium tumefaciens* T-DNA (Depicker et al., 1982, J. Mol. Appl. Genet. 1 (6), 561–573). The maize ubiquitin promoter, the phosphomannose isomerase coding region and the nos terminator are located at nt 31 to nt 2012, nt 2109 to nt 3212 and nt 3273 to 3521 respectively, of pNOV2117 (SEQ ID NO:44). The reporter-promoter cassettes are inserted closest to the right border. The selectable marker expression cassette in the binary vectors is closest to the left border.

For tomato transformation, pNOV4200 (SEQ ID NO:45) is used as the binary vector, which contains the VS1 origin of replication, a copy of the *Agrobacterium* virG gene in the backbone, and a hygromycin selectable marker cassette between the left and right border sequences. The hygromycin selectable marker cassette comprises the *Arabidopsis* Ubiquitin 3 promoter (Ubq3(At), Callis et al., J. Biol. Chem. 265:12486–12493 (1990)) operably linked to the gene encoding hygromycin resistance (denoted here as "HYG", synthetic hygromycin B phosphotransferase gene from *E.coli*, Patent: JP 1986085192-A 1 30-APR-1986) and the nos terminator (Depicker et al., J. Mol. Appl. Genet. 1 (6), 561–573 (1982). The *Arabidopsis* ubiquitin promoter, HYG gene and nos terminator are located at nt 162 to nt 11494, nt 1897 to nt 2939 and nt 2939 to nt 3236, respectively of pNOV4200 (SEQ ID NO:45). The reporter-promoter cassettes (SEQ ID NO:40 to 43) are inserted closest to the right border. The selectable marker expression cassette in the binary vectors is closest to the left border.

Shown below are the orientations of the selectable marker and promoter-reporter cassettes in the binary vector constructs.

4. Binary Vector Constructs:

NOV4215 (RB CmpS promoter fragment+synGFPI gene+nos–ZmUbi+PMI gene+nos LB)
NOV4216 (RB nos+synGFPI gene+CmpS promoter fragment–ZmUbi+PMI gene+nos LB)
NOV4217 (RB CmpS promoter fragment+synGFPI gene+nos–Ubq3(At)+HYG gene+nos LB)
NOV4220 (RB CmpS promoter fragment+GIG gene+nos–Ubq3(At)+HYG gene+nos LB)
NOV4224 (RB CmpC promoter fragment+GIG gene+nos–ZmUbi+HYG gene+nos LB)
NOV4226 (RB CmpC promoter fragment+synGFPI gene+nos–ZmUbi+PMI gene+nos LB)

Additional cassettes are constructed with known promoters to be used for comparison. To this end, a promoter cassette, ZmUbi-GFP-35S term (SEQ ID NO:46), comprising the maize Ubiquitin promoter (Christensen et al. Plant Molec. Biol. 12: 619–632 (1989)) operatively linked with synGFP and the 35S terminator (35S term) is constructed and a promoter cassette comprising the maize ubiquitin promoter operatively linked with the GIG gene and the nos terminator (NOV 3612, SEQ ID NO:47) is also constructed The ZmUbi promoter, GFP gene and 35S terminator are located at nt 1 to nt 2019, nt 2020 to nt 2751 and nt 2876 to nt 2949, respectively of SEQ ID NO:46. The ZmUbi promoter, GIG gene and nos terminator are located at nt 1 to nt 1982, nt 2015 to nt 4015 and nt 4069 to nt 4341, respectively of SEQ ID NO:47. The ZmUbi-GIG nos cassette (SEQ ID NO: 47) is cloned into a pUC-based vector. The ZmUbi-GFP-nos cassette (SEQ ID NO:46) is cloned into the pNOV2117 binary vector for maize transformation, as described above. Promoter cassettes comprising the *Arabidopsis* Ubiquitin3 promoter (Ubq3(At)) operatively linked to synGFPI and the nos terminator (SEQ ID NO:48) and the *Arabidopsis* Ubiquitin3 promoter operatively linked to GIG gene and the nos terminator (SEQ ID NO:49) are constructed. The Ubiqutin3 promoter, synGFPI and the nos terminator are located at nt 1 to nt 1332, nt 1738 to nt 2658 and nt 2670 to nt 2943, respectively of SEQ ID NO: 48. The Ubiquitin3 promoter, GIG gene and the nos terminator are located at nt 1 to nt 1335, nt 1746 to nt 3746 and nt 3800 to nt 4072, respectively of SEQ ID NO: 49. As described above, the promoter cassettes are cloned into the pNOV4200 binary vector containing a hygromycin selectable marker cassette for tomato transformation. Shown below are the orientations of the selectable marker and promoter-reporter cassettes in the binary vector constructs.

5. Binary Vector Constructs

NOV2110 (RB ZmUbi Promoter+synGFP gene+35S term–ZmUbi+PMI gene+nos LB)

NOV4209 (RB Ubq3(At) promoter+synGFPI gene+nos–Ubq3(At)+HYG gene+nos LB)

NOV4208 (RB Ubq3(At) promoter+GUS–Intron–GUS gene+nos–Ubq3(At)+HYG gene+nos LB)

Example 20

*Agrobacterium*-mediated Transformation of Maize

Transformation of immature maize embryos is performed essentially as described in Negrotto et al., (2000) Plant Cell Reports 19: 798–803. For this example, all media constituents are as described in Negrotto et al., supra. However, various media constituents described in the literature may be substituted.

1. Transformation Plasmids and Selectable Marker

The genes used for transformation are cloned into a vector suitable for maize transformation as described in Example 19. Vectors used contain the phosphomannose isomerase (PMI) gene (Negrotto et al. (2000) Plant Cell Reports 19: 798–803).

2. Preparation of *Agrobacterium tumefaciens*

*Agrobacterium* strain LBA4404 (pSB1) containing the plant transformation plasmid is grown on YEP (yeast extract (5 g/L), peptone (10 g/L), NaCl (5 g/L), 15 g/l agar, pH 6.8) solid medium for 2 to 4 days at 28° C. Approximately $0.8 \times 10^9$ *Agrobacteria* are suspended in LS-inf media supplemented with 100 μM acetosyringone (As) (Negrotto et al., (2000) Plant Cell Rep 19: 798–803). Bacteria are pre-induced in this medium for 30–60 minutes.

3. Inoculation

Immature embryos from A188 or other suitable maize genotypes are excised from 8–12 day old ears into liquid LS-inf+100 μM As. Embryos are rinsed once with fresh infection medium. *Agrobacterium* solution is then added and embryos are vortexed for 30 seconds and allowed to settle with the bacteria for 5 minutes. The embryos are then transferred scutellum side up to LSAs medium and cultured in the dark for two to three days. Subsequently, between 20 and 25 embryos per petri plate are transferred to LSDc medium supplemented with cefotaxime (250 mg/l) and silver nitrate (1.6 mg/l) and cultured in the dark for 28° C. for 10 days.

4. Selection of Transformed Cells and Regeneration of Transformed Plants

Immature embryos producing embryogenic callus are transferred to LSD1M0.5S medium. The cultures are selected on this medium for 6 weeks with a subculture step at 3 weeks. Surviving calli are transferred either to LSD1M0.5S medium to be bulked-up or to Reg1 medium. Following culturing in the light (16 hour light/8 hour dark regiment), green tissues are then transferred to Reg2 medium without growth regulators and incubated for 1–2 weeks. Plantlets are transferred to Magenta GA-7 boxes (Magenta Corp, Chicago Ill.) containing Reg3 medium and grown in the light. Plants that are PCR positive for the promoter-reporter cassette are transferred to soil and grown in the greenhouse.

Example 21

Stable Transformation of Tomato

Transformation of tomato is performed essentially as described in Meissner et al., The Plant Journal 12:1465–1472, 1997.

1. Transformation Plasmids and Selectable Marker

The genes used for transformation are cloned into a binary vector suitable for tomato transformation as described in Example 19. Vectors contain the hygromycin resistance gene for selection.

2. Preparation of *Agrobacterium tumefaciens*

*Agrobacterium* strain GV3101 containing the plant transformation plasmid is grown on LB (yeast extract (5 g/L), peptone (10 g/L), NaCl (5 g/L), 15 g/l agar, pH 6.8) liquid media for 2 days at 22° C. Approximately $0.8 \times 10^9$ *Agrobacteria* are suspended in KCMS inoculation media (MS salts (4.3 g/l), Myo-Inositol, Thiamine (1.3 ug/ml), 2,4-D (0.2 ug/ml), Kinetin 0.1 ug/ml and 3% Sucrose, pH 5.5) supplemented with 100 μM acetosyringone. Bacteria are pre-induced in this medium for 60 minutes.

3. Seeds Sterilization and Germination.

Seeds of Micro-Tom cultivar of tomato (Meissner et al., The Plant Journal 12: 1465–1472, 1997) and ZTV-840 cultivars are soaked in 20% bleach solution with Tween for 20 min. Seeds are then washed three times with sterile water and plated on TSG media (½ MS saltes, 1% Sucrose, 1% PhytoAgar, pH 5.8) in Magenta boxes (Magenta Corp, Chicago Ill.) for germination. Cotyledons are excised and cotyledon petioles are cut into 5 mm segments 7 to 10 days after germination.

4. Inoculation

Seven to ten day old cotyledons and cotyledonal petioles segments are incubated for 24 hrs on tobacco BY-2 feeder cells plates (MS salts, Myo-inisitol 0.1 mg/ml, Casein Hydrolysate 0.2 mg/ml, Thiamine-HCl 1.3 μg/ml, 3% Sucrose, pH 5.5) prior to inoculation with *Agrobacterium*.

Cotyledons are dipped into liquid KCMS *Agrobacterium* suspension for 5 minutes. Between 20 and 25 cotyledons are then transferred abaxial side upward on the same feeder cell plates and cultured in the dark for two to three days.

5. Selection of Transformed Cotyledons and Petiols and Regeneration of Transformed Plants Cotyledons and petiole fragments are transferred onto selection media TSM-1 (4.3 g/l MS salts, 1× B5 Vitamins, 2% Sucrose, 1% Glucose, 1 μg/ml Zeatin, 0.05 μg/ml IAA, 5 μg/ml Hygromicine and 250 μg/ml Carbenicillin, pH 5.8) two to three days after inoculation with *Agrobacterium* in the light. Cotyledons and petiole segments producing embryogenic callus are transferred to TSM-2 medium (MS Salts 4.3 g/1, 1× MS Vitamins, 2% Sucrose, 1 µg/ml Zeatin, 5 µg/ml Hygromicine and 250 µg/ml Carbenicillin, pH 5.8). Surviving calli forming plantlets are transferred to Magenta GA-7 boxes (Magenta Corp, Chicago Ill.) containing TRM medium (4.3 g/l MS salt, 1× MS Vitamins, 2% Sucrose pH 5.8) and grown in the light. After root formation primary transformants are transferred to soil.

Example 22

Green Fluorescent Protein (GFP) Fluorometric Assay

For detection of synGFP gene expression the fluorometric assay is performed. Leaf discs of stably transformed maize and tomato are frozen on dry ice. Frozen tissue is throughly ground and mixed with 300 µl of GFP Extraction Buffer (10 mM Tris-HCl (pH 7.5), 100 mM NaCl, 1 mM MgCl2, 10 mM DTT and 0.1% Sarcosyl). The extracts are separated from the leaf debris by centrifugation followed by transfer into 96 well black plate with clear bottom (Costar 3615). Relative fluoresence units (RFU) are measured by Spectra Fluor Plus Plate Reader at 465 nm excitation and 512 nm emission. GFP activity is normalized to total protein measured using BCA Assay (according to Pierce).

Example 23

Expression Analysis of Stably Transformed Maize and Tomato Plants

1. Zea mays Transgenic To Plants

GFP expression is 10 to 20 times higher under the control of the CmpS promoter (NOV4215, NOV4216) compared to the ZmUbi promoter (NOV2110). These results are obtained from leaf samples of 42 independent To lines representing a total of 93 To plants.

2. GFP Elisa Assay

A quantitative sandwich immunoassay is carried out for the detection of green fluorescent protein (GFP). Two commercially available polyclonal antibodies are used. The goat anti-GFP IAP (Rockland, #600-1-1-215) is immunoaffinity purified and the rabbit anti-GFP antibody (Torrey Pines Biolabs, #TP401) is protein A purified. The GFP protein in the plant extract is captured onto the solid phase microtiter by the rabbit antibody. Then a "sandwich" is formed between the solid phase rabbit antibody, the GFP protein, and the secondary goat antibody that is in the well. After a wash step, where unbound secondary antibody is removed, the bound antibody is detected using an alkaline phosphatase-labeled antibody. Substrate for the enzyme is added and color development is measured by reading the absorbance of each well. The reading is then fit to a standard curve to plot the GFP concentrations versus the absorbance

| | synGFP reporter gene | |
|---|---|---|
| Binary vector Cassette | GFP Activity (Average) RFU/mf protein | ELISA (Average) ng GFP/mg protein |
| NOV4215 (CmpS) | 4722.3 | 657.1 |
| NOV4216 (CmpS) | 2795.8 | 246.1 |
| NOV2110 (ZmUbi) | 272.0 | 41.4 |

2. Lycopersicon esculentum to Plants

The CmpS fragment of CmYLCV promoter (NOV 4217) results in synGFP expression level that is significantly higher then the expression level of Ubq3 promoter of Arabidopsis (NOV 4209).

synGFP Reporter Gene

The results are obtained from evaluating of intensity of synGFP fluorescence by microscopy in callus and primary shoots of 5 independent stably transformed callus lines transformed with the NOV4217 cassette and 2 independent stably transformed callus lines transformed with the NOV4209 cassette.

| Binary vector Cassette (Promoter) | Callus ID | GFP Fluorescence Intensity |
|---|---|---|
| NOV4217 (CmpS) | NOV4217-1 | +++++ |
| NOV4217 (CmpS) | NOV4217-2 | ++++ |
| NOV4217 (CmpS) | NOV4217-3 | ++++ |
| NOV4217 (CmpS) | NOV4217-4 | +++ |
| NOV4217 (CmpS) | NOV4217-5 | +++ |
| NOV4209 (Ubq3 (At)) | NOV4209-1 | + |
| NOV4209 (Ubq3 (At)) | NOV4209-2 | + |

Gus-Intron-GUS Reporter Gene

The results are obtained from evaluating of intensity of GUS staining in 11 independent stably transformed callus lines containing the CmpS promoter-reporter cassettes (lines NOV4220-1 through NOV4220-11). Two stably transformed callus lines containing CmpC promoter fragment of CmYLCV promoter (NOV4224-1, NOV4224-2) are evaluated. For comparison two stably transformed callus lines containing the Arabidopsis Ubiquitin 3 (Ubq3) promoter (NOV4208-1, NOV4208-2) are evaluated.

| Binary vector cassette (Promoter) | Callus ID | GUS Staining |
|---|---|---|
| NOV4220 (CmpS) | NOV4220-1 | ++++ |
| NOV4220 (CmpS) | NOV4220-2 | +++ |
| NOV4220 (CmpS) | NOV4220-3 | ++++ |
| NOV4220 (CmpS) | NOV4220-4 | +++++ |
| NOV4220 (CmpS) | NOV4220-5 | +++++ |
| NOV4220 (CmpS) | NOV4220-6 | +++ |
| NOV4220 (CmpS) | NOV4220-7 | ++++ |
| NOV4220 (CmpS) | NOV4220-8 | +++++ |
| NOV4220 (CmpS) | NOV4220-9 | ++++ |
| NOV4220 (CmpS) | NOV4220-10 | +++ |
| NOV4220 (CmpS) | NOV4220-11 | ++++ |
| NOV4224 (CmpC) | NOV4224-1 | ++++ |
| NOV4224 (CmpC) | NOV4224-2 | +++ |
| NOV4208 (Ubq3 (At)) | NOV4208-1 | + |
| NOV4208 (Ubq3(At)) | NOV4208-2 | ++ |

Example 24

Transient Expression Experiments in Maize

1. Embryos Preparation

Immature embryos from A188 or other suitable maize genotypes are excised from 8–12 day old ears into liquid 2DG4+0.5d (Duncan's D medium modified to contain 20 mg/l glucose and supplemented with 10 g/l mannose) and cultured for 1 to 2 days.

2. Plasmolysis

Immature embryos were incubated in 12% sucrose solution for 3–4 hour prior bombardment. Embryos are arranged in 8–10 mm circles on a plate.

3. Bombardment

Transfection by Particle Bombardment of Maize embryos is performed in the presence of 5 μg of plasmid DNA at 650 psi as described (Wright et al, 2001, Plant Cell Reports, In Press) In case an 'in press' reference won't do, here are the details lifted from the paper: Fragment DNA is precipitated onto gold microcarriers (<1 um) as described in the DuPont Biolistics Manual. Genes are delivered to the target tissue cells using the PDS-1000He Biolisitcs device. The settings on the device are as follows: 8 mm between the rupture disk and the macrocarrier, 10 mm between the macrocarrier and the stopping screen and 7 cm between the stopping screen and the target. The plates are shot twice with DNA-coated particles using 650 psi-rupture disks. To reduce tissue damage from the shock wave of the helium blast, a stainless steel mesh, 200 openings per lineal inch horizontally and vertically (McMaster-Carr, New Brunswick, N.J.) is placed between the stopping screen and the target tissue. Embryos are cultivated on the plates for 48 hrs in the dark at 25° C. Protein extracts are prepared by lysing cells in GUS lysis buffer and clarified by centrifugation.

Example 25

GUS Assays

For detection of GUS gene expression the histochemical and chemiluminescent assays are performed.

1. Histochemical β-glucuronidase (GUS) Assay

Maize embryos and tomato in vitro callus lines are used in GUS assays. Either whole embryos or small pieces of callus are dipped into GUS staining solution. GUS staining solution contains 1 mM 5-bromo-4-chloro-3-indolyl glucuronide (X-Gluc, Duchefa, 20 mM stock in DMSO), 100 mM Na-phosphate buffer pH 7.0, 10 mM EDTA pH 8.0, and 0.1% Triton X100. Tissue samples are incubated at 37° C. for 1–16 hours. If necessary, samples are cleared with several washes of 70% EtOH to remove chlorophyll

2. β-glucuronidase (GUS) Chemilluminescent Assay

For quantitive analysis of Gus expression the GUS chemilluminescent assay is performed using GUS-Light Kit (Tropix. Inc) according to manufacturer's instructions.

The activity is measured in a Luminometer.

The GUS results with construct pCmpS and pCmpMG (Example 17) are normalized to a comparison clone value (pNOV3612, Example 19). Results obtained from two different experiments show that the 8 bp deletion in CmYLCV promoter (pCmpMG, Example 17) does not significantly affect the expression levels of the GUS reporter as compared to pCmpS.

Transient Expression in *Z. mays* Embryos

GUS Activity at 48 and 72 Hours After Transfection

| Construct ID | GUS Activity RFU/mg protein | |
|---|---|---|
| | 48 hr | 72 hr |
| pCmpS | 103.7 | 51.7 |
| pCmpMG | 81.4 | 70.8 |
| ZmUbi (pNOV3612) | 52.6 | 70.2 |

---

What is claimed is:

1. An isolated DNA sequence capable of driving expression of an associated nucleotide sequence, wherein said DNA sequence comprises a nucleotide sequence characterized by SEQ ID NO:1.

2. The DNA sequence according to claim 1, wherein said DNA sequence further comprises SEQ ID NO:6.

3. An isolated DNA sequence which hybridizes under stringent conditions to a nucleotide sequence characterized by SEQ ID NO:1 or SEQ ID NO:6.

4. A recombinant DNA molecule comprising a full-length transcript promoter region isolated from Cestrum yellow leaf curling virus.

5. A recombinant DNA molecule comprising a DNA sequence according to claim 1 operably linked to a nucleotide sequence of interest.

6. The recombinant DNA molecule of claim 5, wherein the nucleotide sequence of interest comprises a coding sequence.

7. The recombinant DNA molecule of claim 6, wherein the coding sequence encodes a desirable phenotypic trait.

8. The recombinant DNA molecule of claim 7, wherein the coding sequence encodes a protein which confers a positive selective advantage to cells that have been transformed with said coding sequence.

9. The recombinant DNA molecule of claim 7, wherein the coding sequence encodes a protein involved in cellular metabolism of a compound, wherein said compound comprises mannose or xylose.

10. The recombinant DNA molecule of claim 9, wherein said protein comprises one of a xyloisomerase, a phosphomanno-isomerase, a mannose-6-phosphate isomerase, a mannose-1-phosphate isomerase, a phosphomanno mutase, a mannose epimerase, a mannose phosphatase, a xylose phosphatase, a mannose-6-phosphatase, a mannose-1-phosphatase, a mannose permease, and a xylose permease.

11. The recombinant DNA molecule of claim 10, wherein said protein comprises a phosphomanno isomerase.

12. The recombinant DNA molecule of claim 6, wherein said coding sequence is in an antisense orientation.

13. A DNA expression vector comprising the DNA sequence according to claim 1.

14. A DNA expression vector comprising the DNA sequence according to claim 1 operably linked to a nucleotide sequence of interest.

15. The DNA expression vector according to claim 14, wherein said DNA expression vector is capable of altering expression of a viral genome present in a cell.

16. A transgenic host cell comprising the DNA sequence according to claim 1.

17. The host cell of claim 16, wherein said host cell is a plant cell.

18. A transgenic plant or any progeny thereof comprising the DNA sequence according to claim 1.

19. The plant of claim 18, wherein said plant is selected from the group consisting of maize, wheat, sorghum, rye, oats, turf grass, rice, barley, soybean, cotton, tobacco, sugar beet and oilseed rape.

20. An isolated DNA sequence comprising a DNA element, which element has at least about 90% sequence identity with a consecutive stretch from about 200 to about 400 nucleotides of SEQ ID NO:1, wherein said DNA sequence is capable of driving expression of an associated nucleotide sequence.

21. An isolated DNA sequence of claim 20 wherein said DNA element is a consecutive stretch from about 200 to about 400 nucleotides of SEQ ID NO:1.

* * * * *